(12) United States Patent
Yeung et al.

(10) Patent No.: US 10,136,799 B2
(45) Date of Patent: Nov. 27, 2018

(54) ENDOSCOPIC SYSTEMS, DEVICES, AND METHODS

(71) Applicant: Bio-Medical Engineering (HK) Limited, Hong Kong SAR (CN)

(72) Inventors: Chung-Kwong Yeung, Hong Kong SAR (CN); Steven Chu, Menlo Park, CA (US); Wing Fai Lam, Hong Kong SAR (CN)

(73) Assignee: Bio-Medical Engineering (HK) Limited, Hong Kong SAR (CN)

( * ) Notice: Subject to any disclaimer, the term of this patent is extended or adjusted under 35 U.S.C. 154(b) by 0 days.

(21) Appl. No.: 15/710,555

(22) Filed: Sep. 20, 2017

(65) Prior Publication Data

US 2018/0070800 A1 Mar. 15, 2018

Related U.S. Application Data

(63) Continuation-in-part of application No. 15/368,430, filed on Dec. 2, 2016, which is a continuation of
(Continued)

(51) Int. Cl.
*A61B 1/00* (2006.01)
*A61B 1/005* (2006.01)
(Continued)

(52) U.S. Cl.
CPC .......... *A61B 1/00156* (2013.01); *A61B 1/008* (2013.01); *A61B 1/0051* (2013.01);
(Continued)

(58) Field of Classification Search
CPC ............ A61B 1/00082; A61B 1/00094; A61B 1/00135; A61B 1/00142; A61B 1/00154;
(Continued)

(56) References Cited

U.S. PATENT DOCUMENTS 5,619,993 A 4/1997 Lee
7,935,047 B2 5/2011 Yoshida et al.
(Continued)

FOREIGN PATENT DOCUMENTS

CN 1051125 A 5/1991
CN 1933765 A 3/2007
(Continued)

OTHER PUBLICATIONS

International Search Report of PCT/CN2017/102964 dated Dec. 25, 2017, 5 pgs.
(Continued)

*Primary Examiner* — Ryan Henderson
(74) *Attorney, Agent, or Firm* — Baker & McKenzie LLP

(57) ABSTRACT

Example embodiments relate to endoscopic systems. The system includes an elongated main body having a first end. The system may further comprise an anchor assembly attached to the main body near the first end of the main body. The anchor assembly may comprise a first expandable member. The first expandable member may be configurable to expand radially away from the main body. The anchor assembly may further comprise a second expandable member provided between the first expandable member and the first end of the main body. The second expandable member may be configurable to expand radially away from the main body. The anchor assembly may be operable to secure the main body with respect to an interior wall forming the cavity of the patient.

15 Claims, 33 Drawing Sheets

Related U.S. Application Data application No. 14/985,587, filed on Dec. 31, 2015, application No. 15/710,555, which is a continuation-in-part of application No. 14/985,587, filed on Dec. 31, 2015.

(60) Provisional application No. 62/233,828, filed on Sep. 28, 2015.

(51) Int. Cl.
*A61B 1/31* (2006.01)
*A61M 25/10* (2013.01)
*A61B 1/015* (2006.01)
*A61B 1/008* (2006.01)
*A61B 17/00* (2006.01)
*A61B 17/22* (2006.01)

(52) U.S. Cl.
CPC ........ *A61B 1/0057* (2013.01); *A61B 1/00082* (2013.01); *A61B 1/00087* (2013.01); *A61B 1/00094* (2013.01); *A61B 1/00147* (2013.01); *A61B 1/00154* (2013.01); *A61B 1/015* (2013.01); *A61B 1/31* (2013.01); *A61M 25/1002* (2013.01); *A61M 25/1011* (2013.01); *A61B 2017/00296* (2013.01); *A61B 2017/22055* (2013.01); *A61B 2017/22069* (2013.01); *A61M 2025/1013* (2013.01); *A61M 2025/1015* (2013.01); *A61M 2025/1047* (2013.01); *A61M 2025/1086* (2013.01)

(58) Field of Classification Search
CPC ..... A61B 1/005; A61B 1/0055; A61B 1/0057; A61B 1/015; A61B 1/31; A61M 25/1011; A61M 25/1009; A61M 25/1006
USPC ................ 600/114–116, 121–125, 104, 106; 604/95.01–95.05, 96.01, 101.01–101.05, 604/102.01–102.03
See application file for complete search history.

(56) References Cited

U.S. PATENT DOCUMENTS

| | | | |
|---|---|---|---|
| 2001/0007917 A1 | 7/2001 | Hayakawa et al. | |
| 2004/0186349 A1 | 9/2004 | Ewers et al. | |
| 2005/0137457 A1* | 6/2005 | MacHida | A61B 1/00082 600/115 |
| 2005/0222500 A1 | 10/2005 | Itoi | |
| 2007/0015965 A1 | 1/2007 | Cox et al. | |
| 2007/0244361 A1* | 10/2007 | Ikeda | A61B 1/00082 600/116 |
| 2008/0091068 A1 | 4/2008 | Terliuc | |
| 2009/0062611 A1* | 3/2009 | Toyama | A61B 1/00082 600/118 |
| 2009/0118582 A1 | 5/2009 | Tsumaru et al. | |
| 2009/0227835 A1 | 9/2009 | Terliuc | |
| 2011/0190583 A1 | 8/2011 | Ashida et al. | |
| 2012/0077920 A1 | 3/2012 | Hirano et al. | |
| 2013/0261544 A1 | 10/2013 | Hardin | |
| 2014/0086772 A1 | 3/2014 | Olsen | |
| 2014/0318118 A1 | 10/2014 | Mazzeo et al. | |
| 2015/0070904 A1 | 3/2015 | Martinez et al. | |
| 2015/0283699 A1 | 10/2015 | Morin et al. | |

FOREIGN PATENT DOCUMENTS

| | | |
|---|---|---|
| CN | 101313839 A | 12/2008 |
| CN | 101378691 A | 3/2009 |
| CN | 201222163 Y | 4/2009 |
| CN | 101632572 A | 1/2010 |
| CN | 103142199 A | 6/2013 |
| CN | 103462583 A | 12/2013 |
| CN | 204182562 U | 3/2015 |
| CN | 204379366 U | 6/2015 |
| CN | 105832279 A | 8/2016 |
| JP | 2008237812 A | 10/2008 |
| WO | 2016/051952 A1 | 4/2016 |

OTHER PUBLICATIONS

Written Opinion of PCT/CN2017/102964 dated Dec. 25, 2017, 4 pgs.
First Office Action with Search Report issued by the PRC State Intellectual Property Office in related PRC application No. CN 201610147810.9, dated Jan. 4, 2017.
International Search Report and Written Opinion, PCT/CN2016/070906, dated Jun. 22, 2016, 13 pages.
Endotics: Painless and Safer Colonscope, http://www.endotics.com, downloaded Mar. 15, 2016, 6 pages.
GIVIEW: Colonscopy Solution: Safe and Easy-to-Use Colonoscopy, http://www.giview.com, downloaded Mar. 15, 2016, 17 pages.
Third Eye Panoramic: Avantis Medical Systems, http://www.thirdeyepanoramic.com, downloaded Mar. 15, 2016, 15 pages.
Dogangil, G., et al., "A review of medical robotics for minimally invasive soft tissue surgery," Proceedings of the Institution of Mechanical Engineers, Part H: Journal of Engineering in Medicine, vol. 224, (2010), pp. 653-679.
Tumino, E., et al., "Endotics system vs colonoscopy for the detection of polyps," WJG: World Journal of Gastroenterology, (Nov. 21, 2010), vol. 16, No. 43, pp. 5452-5456.
Elsayed, Y., et al., "Finite Element Analysis and Design Optimization of a Pneumatically Actuating Silicone Module for Robotic Surgery Applications," Soft Robotics, vol. 2, No. 00, (2014), pp. 255-262.
Patel, N., et al. "Flexible platforms for natural orifice transluminal and endoluminal surgery," Endoscopy International Open, (2014), vol. 02, pp. E117-E123.
Patel, N., et al., "The endoscopy evolution: the superscope era," Frontline Gastroenterology, (2014), Published online May 13, 2014, http://fg.bmj.com, vol. 0, pp. 1-7.

\* cited by examiner

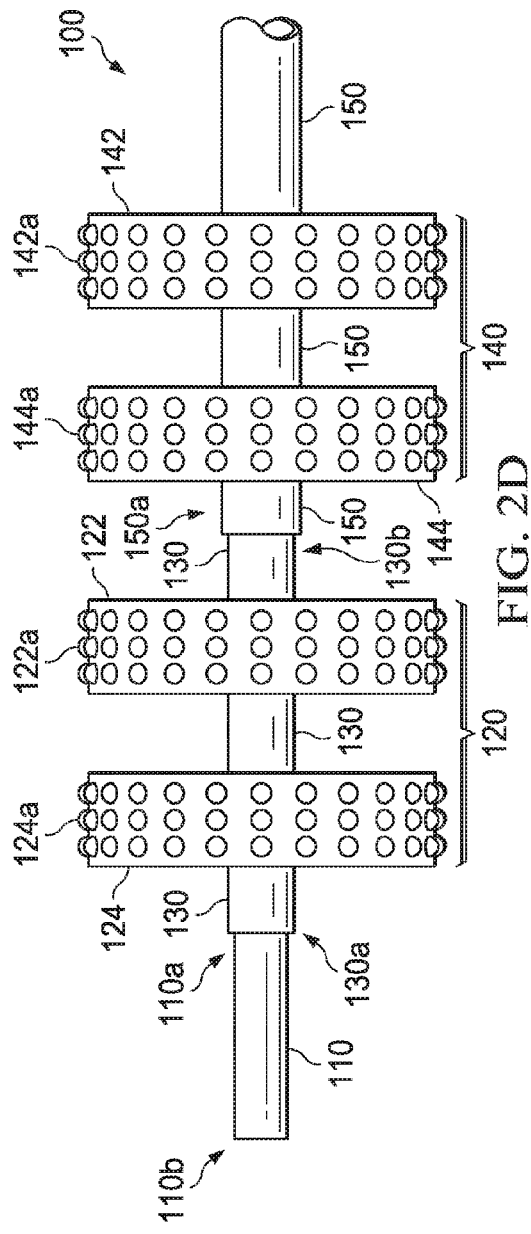
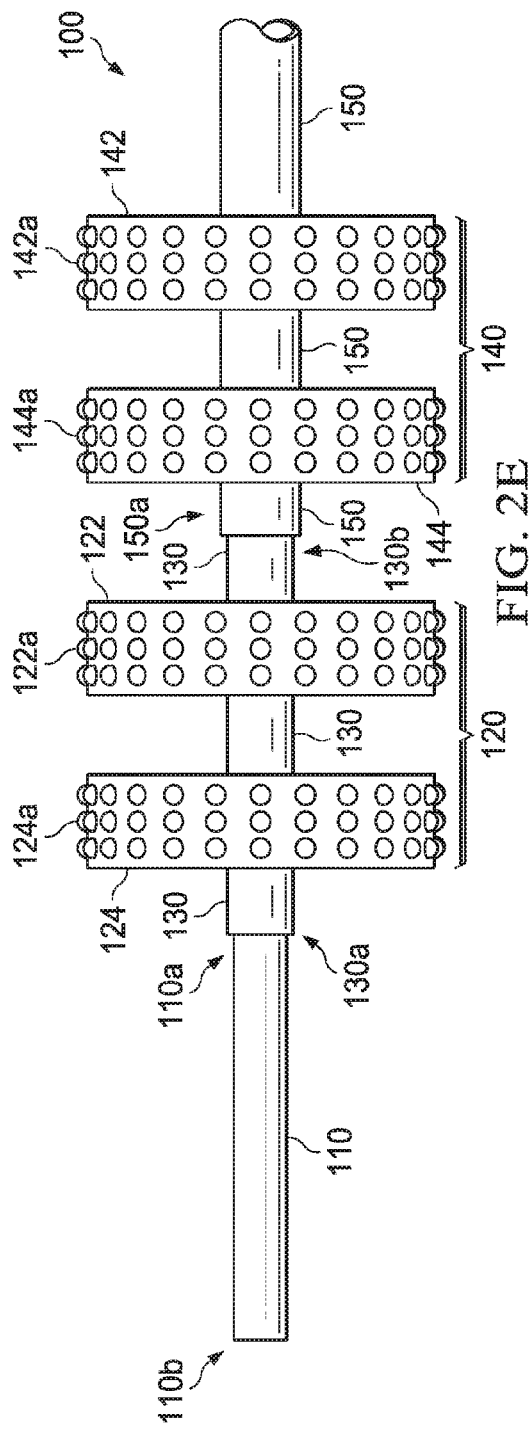

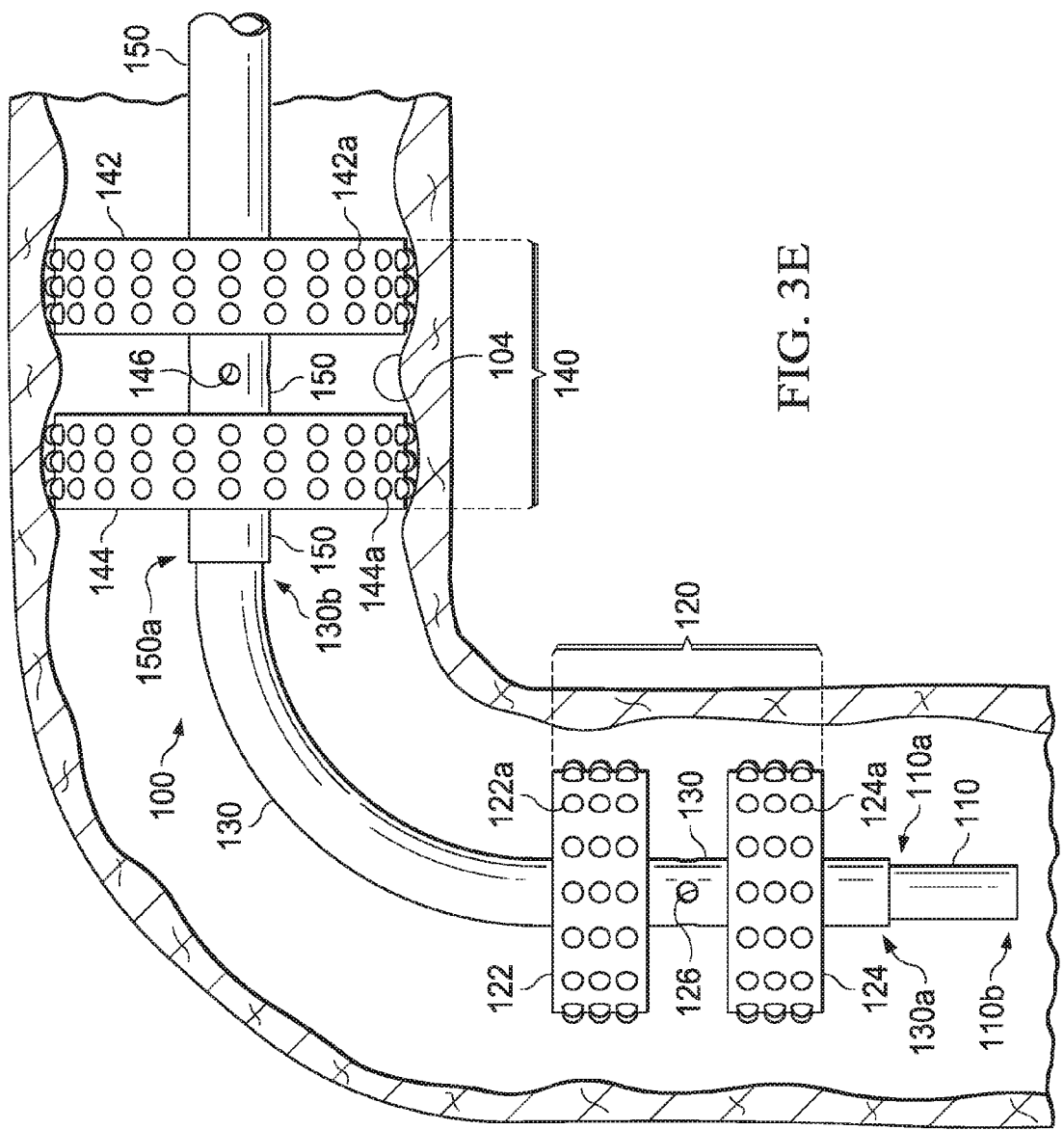

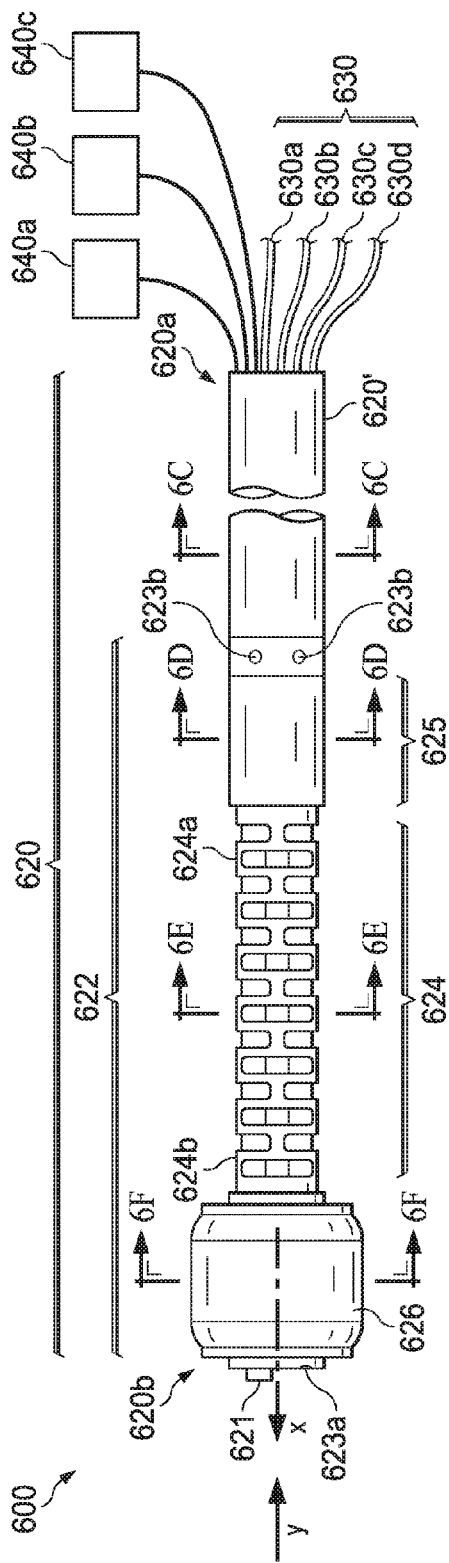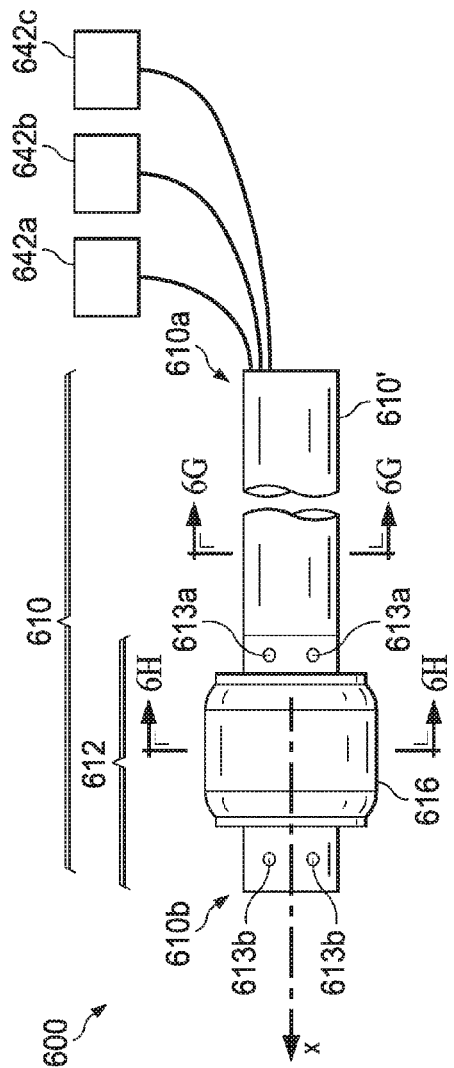
FIG. 6A
FIG. 6B

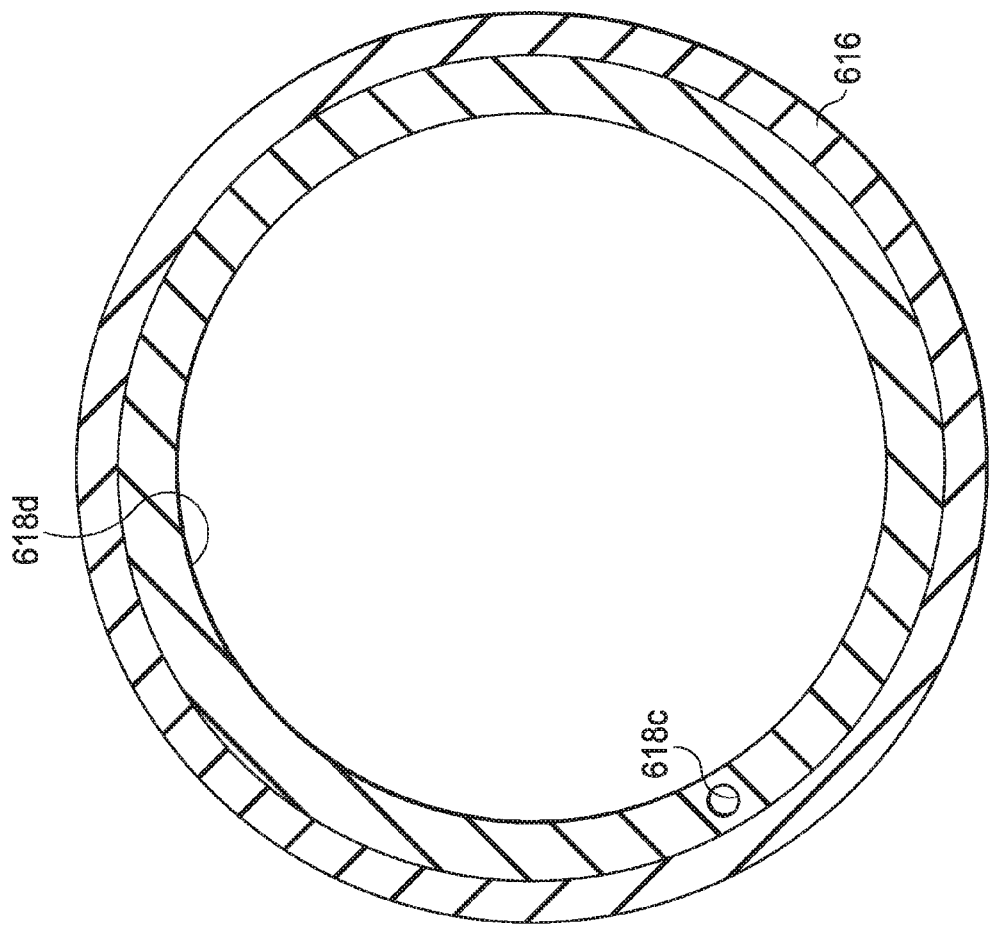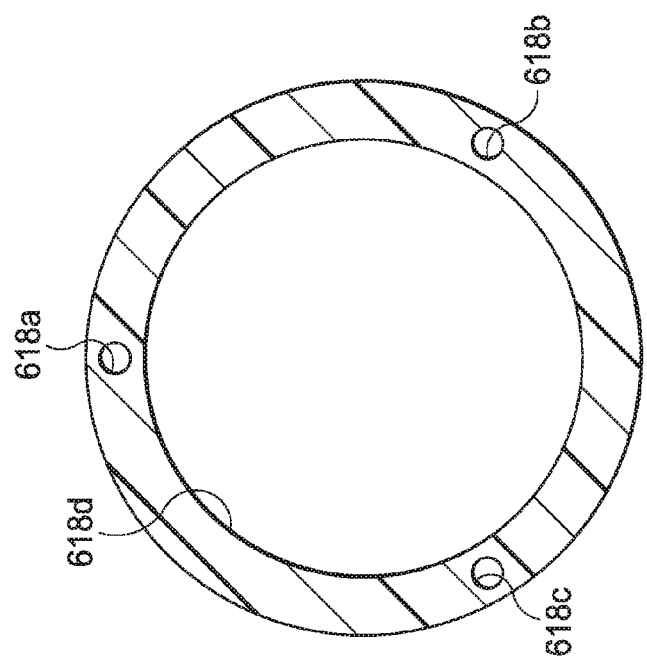

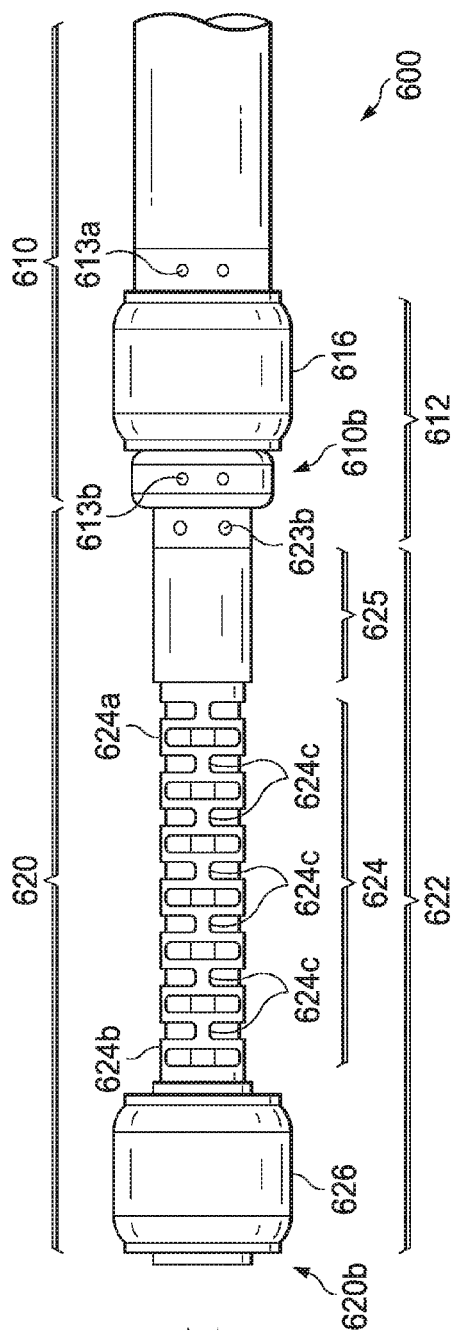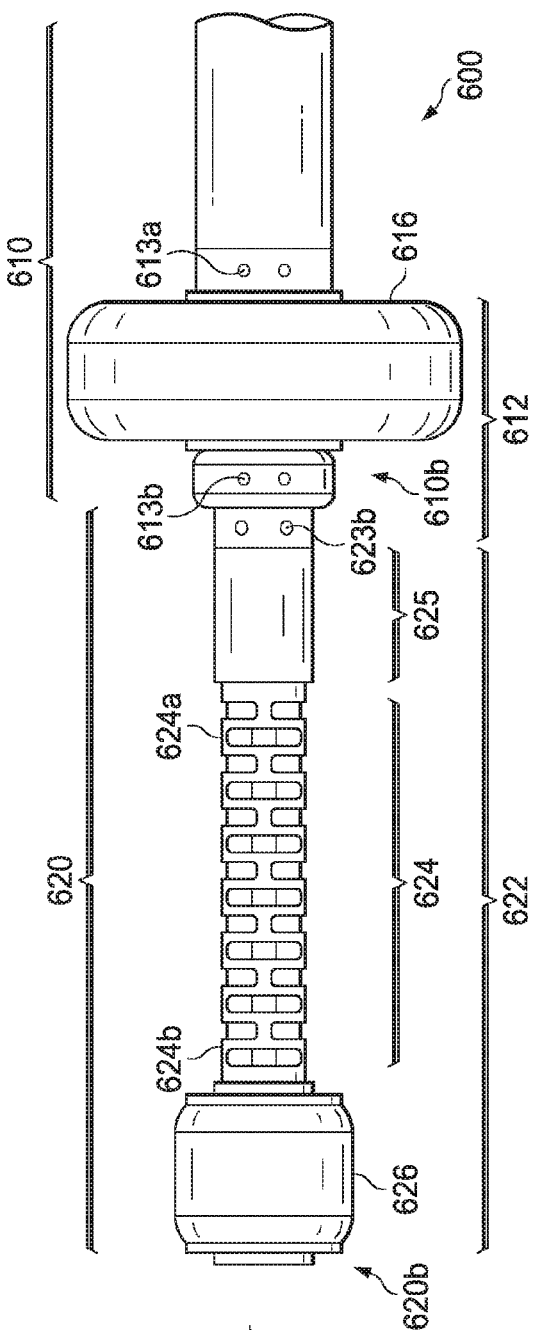

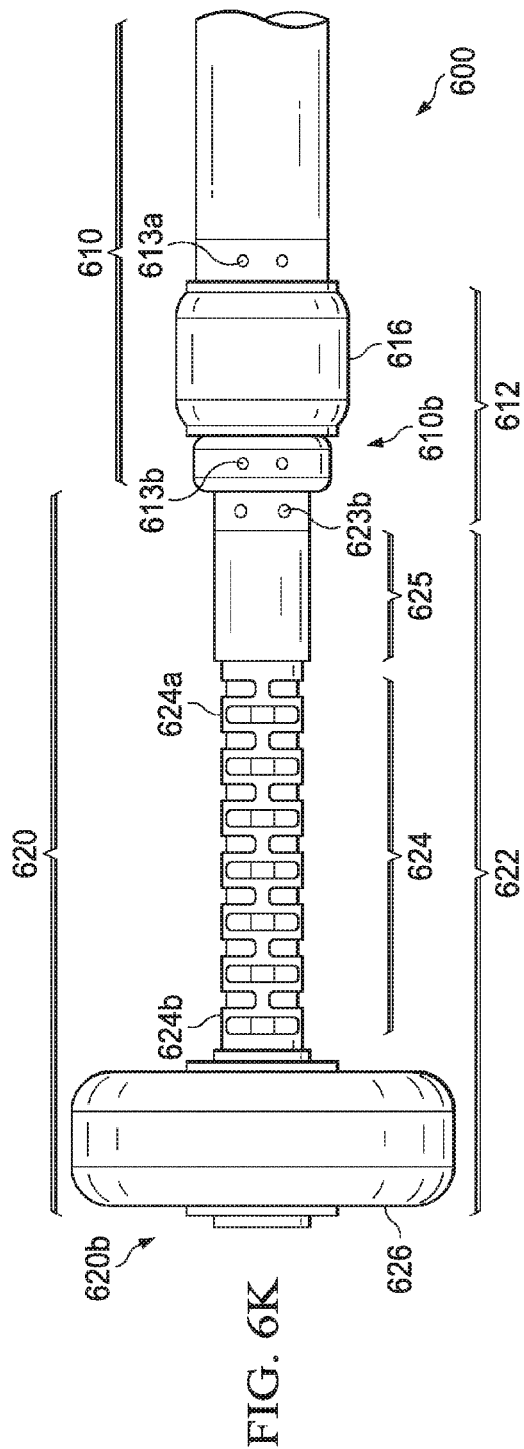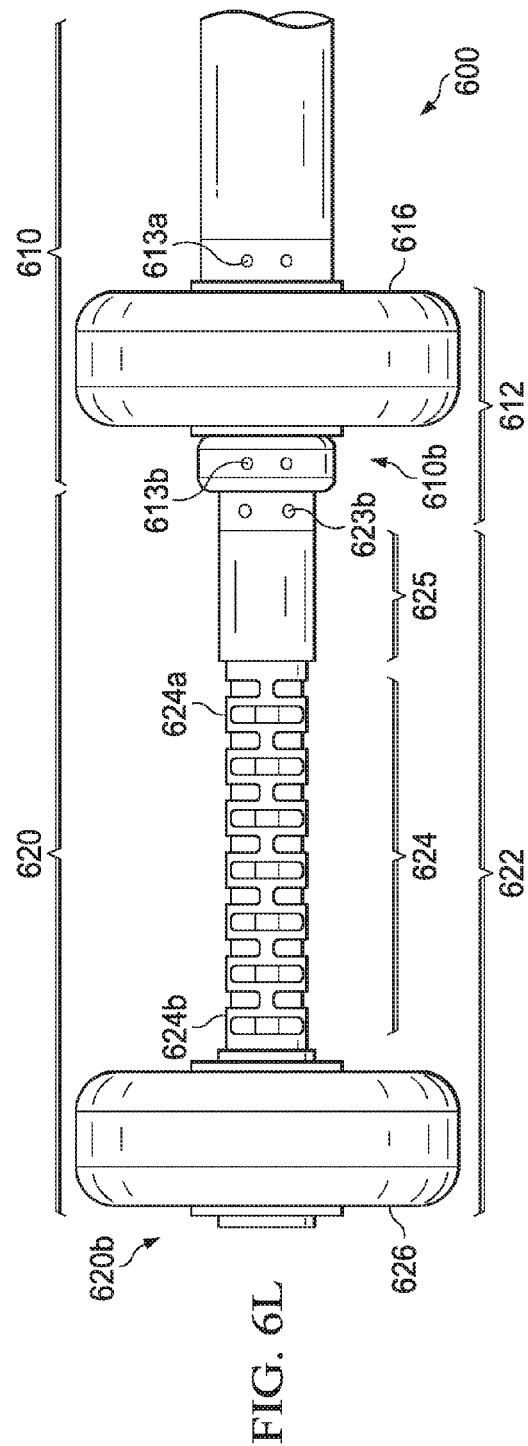

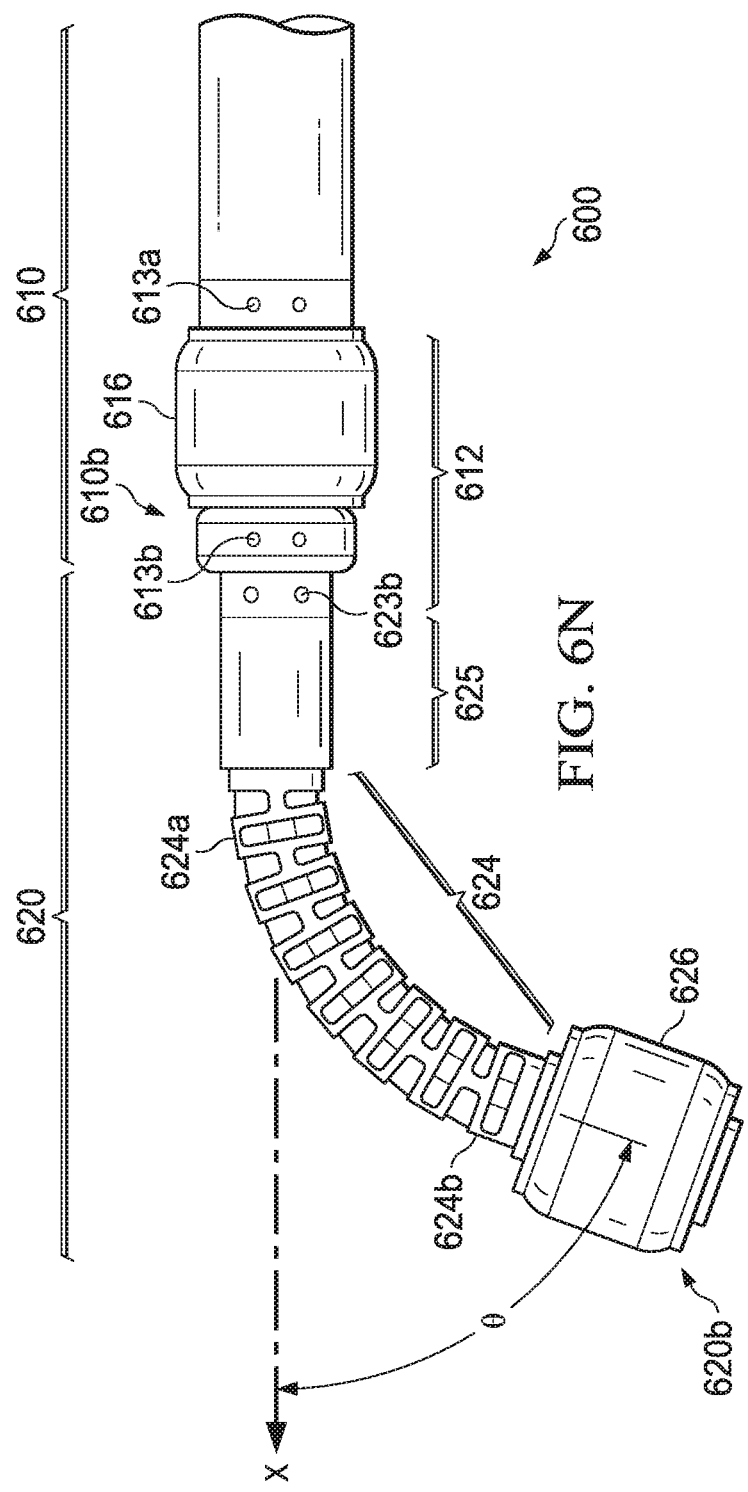

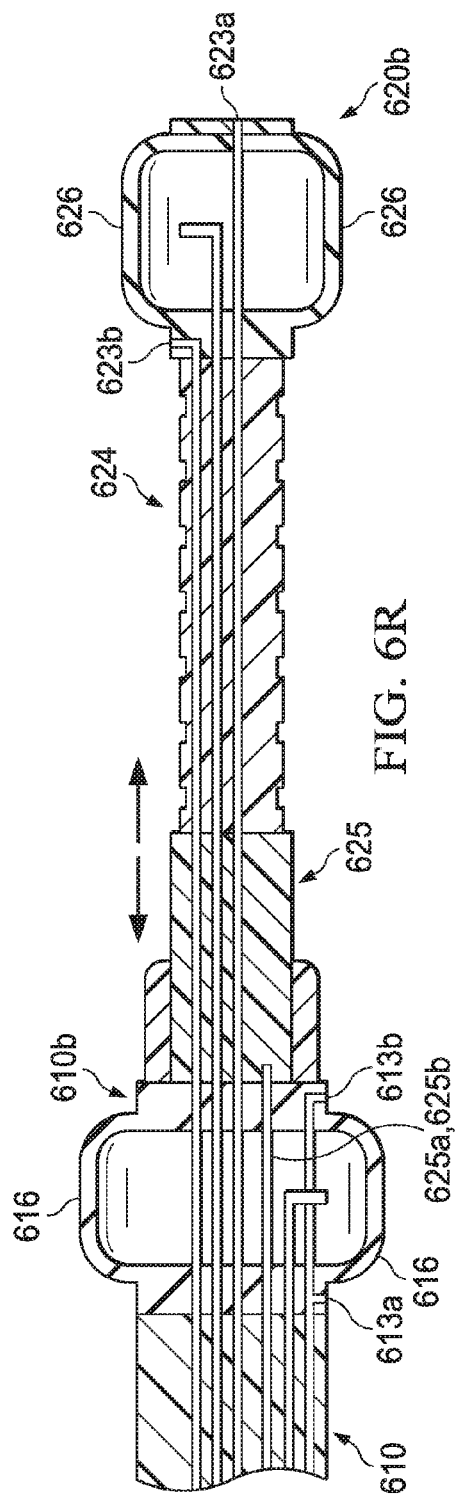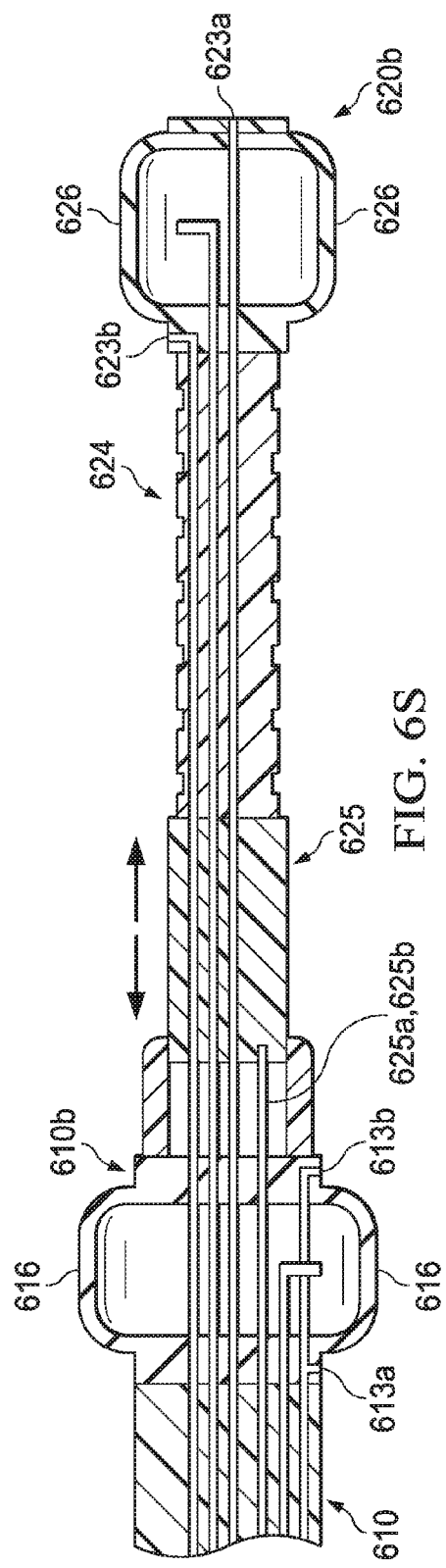

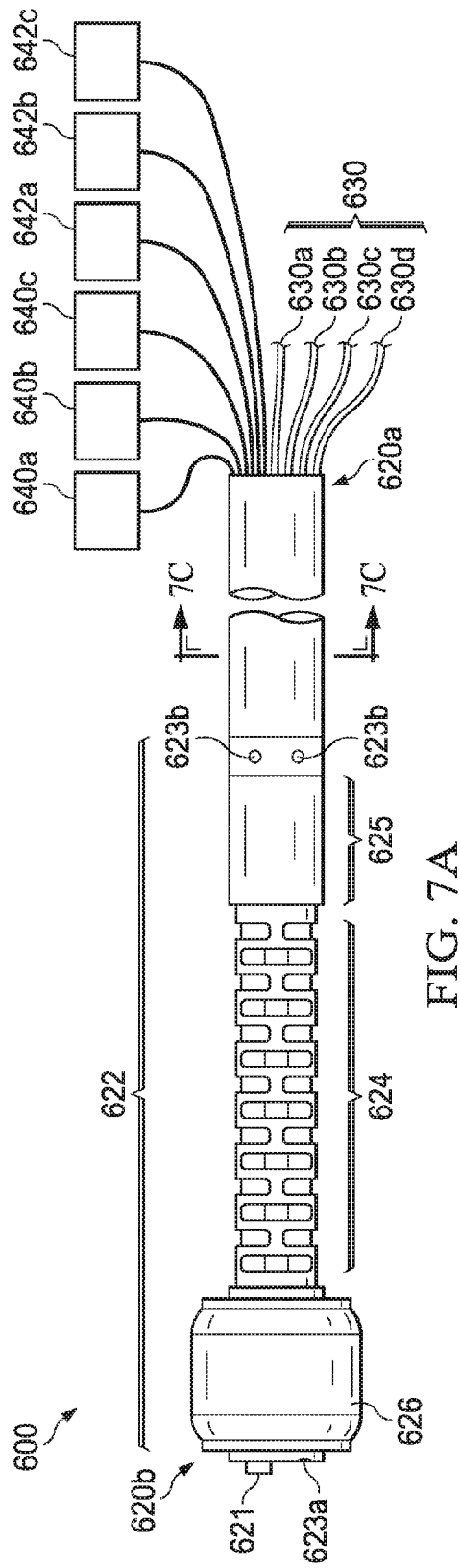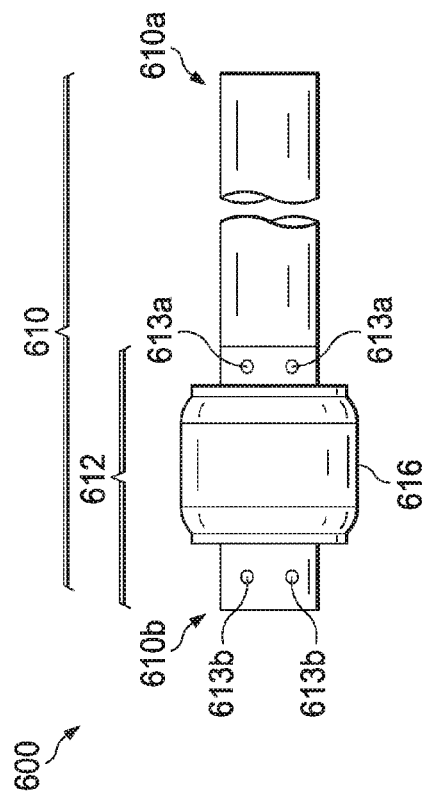
FIG. 7A
FIG. 7B

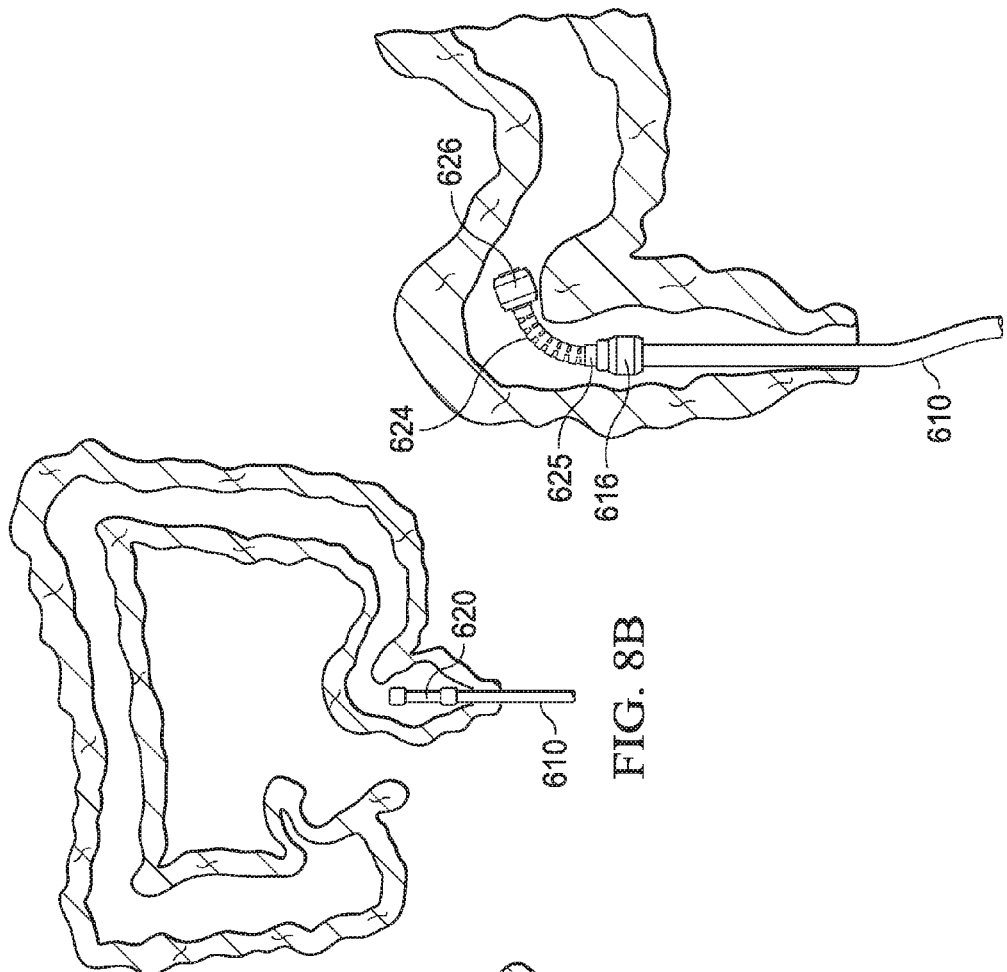
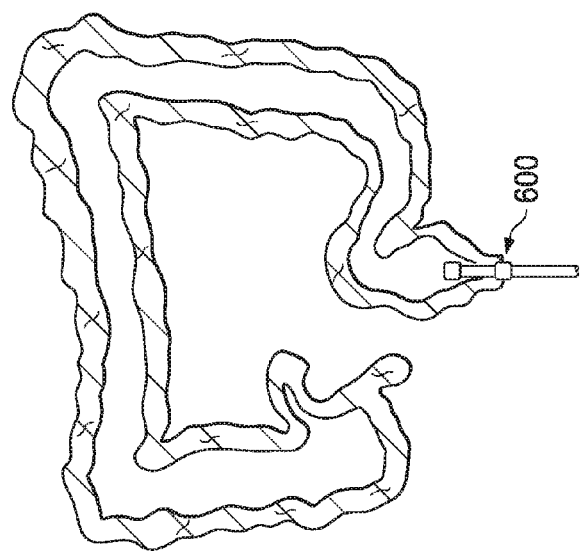
FIG. 8A
FIG. 8B
FIG. 8C

ENDOSCOPIC SYSTEMS, DEVICES, AND METHODS

CROSS-REFERENCE TO RELATED APPLICATIONS

This application is a continuation-in-part of U.S. application Ser. No. 15/368,430 (filed on Dec. 2, 2016, which is a continuation of U.S. application Ser. No. 14/985,587, filed on Dec. 31, 2015, which claims priority to U.S. Provisional Application No. 61/233,828, filed on Sep. 28, 2015) and U.S. application Ser. No. 14/985,587 (filed on Dec. 31, 2015, which claims priority to U.S. Provisional Application No. 61/233,828, filed on Sep. 28, 2015), the contents of all of which are hereby expressly incorporated by reference in their entirety, including the contents and teachings of any references contained therein.

BACKGROUND

The present disclosure relates generally to endoscopic systems, devices, and methods, and more specifically, relates to systems and devices for use in performing endoluminal procedures, including diagnostic and therapeutic procedures, and methods of configuring and using such systems and devices.

Presently, colorectal cancer is the third most commonly diagnosed cancer and also the third leading cause of cancer-related deaths worldwide. If diagnosed at a sufficiently early stage, however, the survival rate of patients suffering from colorectal cancer may reach upwards of ninety percent.

Conventional optical colonoscopy is the most widely accepted and used procedure for colorectal screening. In general, conventional optical colonoscopy involves the insertion of a colonoscope through the colon of a patient, and requires forceful manual pushing of the colonoscope against the luminal wall at flexural or looping/bending sections of the colon during insertion, which generally results in severe discomfort and pain to the patient. The retracting and/or removal of the colonoscope from the flexural and/or looping/bending sections of the colon of the patient may also cause significant discomfort and/or pain to the patient.

BRIEF SUMMARY

Despite recent developments in modern medical science and technology, it is recognized in the present disclosure that one or more problems are encountered in colonoscopy-related diagnostic and therapeutic technologies and methodologies, including those described above and in the present disclosure.

Present example embodiments relate generally to systems, devices, and methods for addressing one or more problems in diagnostic and therapeutic systems, devices, and methods, including those described above and herein.

In an exemplary embodiment, an endoscopic system is described. The endoscopic system may include an outer assembly and a main assembly. The outer assembly may formed as an elongated body. The outer assembly may include a proximal end, a distal end, a first outer pressure cavity provided through the outer assembly between the proximal and distal ends of the outer assembly, a second outer pressure cavity provided through the outer assembly between the proximal and distal ends of the outer assembly, a main cavity provided through the outer assembly between the proximal and distal ends of the outer assembly, and an outer anchor assembly provided at the distal end of the outer assembly. The outer anchor assembly may include a first expandable member and a first outer pressure opening. The first expandable member may be connected to the first outer pressure cavity. The first expandable member may be configurable to expand radially outwards upon receiving a positive pressure from the first outer pressure cavity. The first outer pressure opening may be connected to the second outer pressure cavity. The first outer pressure opening may be provided adjacent to the first expandable member. The first outer pressure opening may be selectively configurable to apply a negative pressure (e.g., a suction force inwards from an exterior of the outer assembly towards the first suction opening) and/or a positive pressure. The main assembly may be formed as an elongated body having at least a portion of its elongated body housed in the main cavity of the outer assembly. The main assembly may include a proximal end, a distal end, a first main pressure cavity provided through the main assembly between the proximal and distal ends of the main assembly, a second main pressure cavity provided through the main assembly between the proximal and distal ends of the main assembly, a plurality of movement cavities, a navigation section, and a plurality of tendon members. The plurality of movement cavities may include a first movement cavity, a second movement cavity, and a third movement cavity. The plurality of movement cavities may be provided through the main assembly between the proximal and distal ends of the main assembly in such a way that the plurality of movement cavities are spaced around a center line axis formed by the elongated body of the main assembly. The navigation section may be formed at the distal end of the main assembly. The navigation section may include an instrument, a first main pressure opening, a bendable section, an extendible section, and a main anchor assembly. The first main pressure opening may be connected to the second main pressure cavity. The first main pressure opening may be selectively configurable to apply a negative pressure (e.g., a suction force inwards from an exterior of the navigation section towards the main suction opening) and/or a positive pressure. The bendable section may include a plurality of subsections, including a most distal subsection and a most proximal subsection. The plurality of subsections may be connected in a linear arrangement. Each subsection may be pivotally moveable relative to an adjacent subsection. Each subsection may include a plurality of openings provided around its center. Each of the most distal subsection and most proximal subsection may include at least a first subsection opening aligned to the first movement cavity, a second subsection opening aligned to the second movement cavity, and a third subsection opening aligned to the third movement cavity. The extendible section may be connected to the most proximal subsection. The extendible section may be configurable to extend in length (e.g., extend in such a way as to move the instrument, the main suction opening, and the bendable section away from the distal end of the outer assembly). The main anchor assembly may be provided between the instrument and the most distal subsection of the bendable section. The main anchor assembly may include a second expandable member connected to the first main pressure cavity. The second expandable member may be configurable to expand radially outwards upon receiving a positive pressure from the first main pressure cavity. The plurality of tendon members may include a first tendon member, a second tendon member, and a third tendon member. At least a portion of each tendon member may be housed in one of the movement cavities. Each tendon member may have a length greater than a length of the outer assembly. The first tendon member may be housed in the first movement cavity. The first tendon member may extend through the first subsection opening of the most proximal subsection. A distal end of the first tendon member may be in communication with (e.g., connect to or pass through) a location of the most distal subsection that is aligned to the first subsection opening and the first movement cavity. At least a distal end of the bendable section may be configurable to bend in a first direction when a force is applied to the first tendon member. The second tendon member may be housed in the second movement cavity. The second tendon member may extend through the second subsection opening of the most proximal subsection. A distal end of the second tendon member may be in communication with (e.g., connect to or pass through) a location of the most distal subsection that is aligned to the second subsection opening and the second movement cavity. At least a distal end of the bendable section may be configurable to bend in a second direction opposite to the first direction when a force is applied to the second tendon member. The third tendon member may be housed in the third movement cavity. The third tendon member may extend through the third subsection opening of the most proximal subsection. A distal end of the third tendon member may be in communication with (e.g., connect to or pass through) a location of the most distal subsection that is aligned to the third subsection opening and the third movement cavity. At least a distal end of the bendable section may be configurable to bend in a third direction orthogonal to the first direction when a force is applied to the third tendon member.

In another exemplary embodiment, an endoscopic system is described. The endoscopic system may include an outer assembly and a main assembly. The outer assembly may be formed as an elongated body. The outer assembly may include a proximal end, a distal end, a first outer pressure cavity provided through the outer assembly between the proximal and distal ends of the outer assembly, a second outer pressure cavity provided through the outer assembly between the proximal and distal ends of the outer assembly, a main cavity provided through the outer assembly between the proximal and distal ends of the outer assembly, and an outer anchor assembly. The outer anchor assembly may be provided at the distal end of the outer assembly. The outer anchor assembly may include a first expandable member and a first outer pressure opening. The first expandable member may be connected to the first outer pressure cavity. The first expandable member may be configurable to expand radially outwards upon receiving a positive pressure from the first outer pressure cavity. The first outer pressure opening may be connected to the second outer pressure cavity. The first outer pressure opening may be provided adjacent to the first expandable member. The first outer pressure opening may be selectively configurable to apply a negative pressure (e.g., a suction force inwards from an exterior of the outer assembly towards the first suction opening) and/or a positive pressure. The main assembly may be formed as an elongated body having at least a portion of its elongated body housed in the main cavity of the outer assembly. The main assembly may include a proximal end, a distal end, a first main pressure cavity provided through the main assembly between the proximal and distal ends of the main assembly, a second main pressure cavity provided through the main assembly between the proximal and distal ends of the main assembly, a plurality of movement cavities, a navigation section, and a plurality of tendon members. The plurality of movement cavities may be provided through the main assembly between the proximal and distal ends of the main assembly in such a way that the plurality of movement cavities are spaced around a center line axis formed by the elongated body of the main assembly. The navigation section may be formed at the distal end of the main assembly. The navigation section may include an instrument, a first main pressure opening, a bendable section, and a main anchor assembly. The first main pressure opening may be connected to the second main pressure cavity. The first main pressure opening may be selectively configurable to apply a negative pressure (e.g., a suction force inwards from an exterior of the navigation section towards the main suction opening) and/or a positive pressure. The bendable section may include a plurality of subsections, including a most distal subsection and a most proximal subsection. The plurality of subsections may be connected in a linear arrangement. Each subsection may be pivotally moveable relative to an adjacent subsection. Each subsection may include a plurality of openings provided around its center. The main anchor assembly may be provided between the instrument and the most distal subsection of the bendable section. The main anchor assembly may include a second expandable member. The second expandable member may be connected to the first main pressure cavity and configurable to expand radially outwards upon receiving a positive pressure from the first main pressure cavity. Regarding the plurality of tendon members, each tendon member may be housed in one of the movement cavities. Each tendon member may have a length greater than a length of the outer assembly. Each tendon member may extend through one of the subsection openings of the most proximal subsection. A distal end of each tendon member may be in communication with (e.g., connect to or pass through) a location of the most distal subsection that is aligned to the subsection opening of the most proximal subsection that received the tendon member. At least a distal end of the bendable section may be configurable to bend when a force is applied to one of the tendon members.

In another exemplary embodiment, an endoscopic system is described. The endoscopic system may include a main assembly and an outer assembly. The main assembly include a proximal end, a distal end, first outer pressure cavity provided through the main assembly between the proximal and distal ends of the main assembly, and a first main pressure cavity provided through the main assembly between the proximal and distal ends of the main assembly. The main assembly may also include second outer pressure cavity provided through the main assembly between the proximal and distal ends of the main assembly. The main assembly may also include a second main pressure cavity provided through the main assembly between the proximal and distal ends of the main assembly. The main assembly may also include a plurality of movement cavities provided through the main assembly between the proximal and distal ends of the main assembly in such a way that the plurality of movement cavities are spaced around a center line axis formed by the elongated body of the main assembly. The main assembly may also include a navigation section and a plurality of tendon members. The navigation section may be formed at the distal end of the main assembly. The navigation section may include an instrument, a first main pressure opening, a bendable section, and a main anchor assembly. The main suction opening may be connected to the second main pressure cavity. The first main pressure opening may be selectively configurable to apply a negative pressure (e.g., a suction force inwards from an exterior of the navigation section towards the main suction opening) and/or a positive pressure. The bendable section may include a plurality of subsections, including a most distal subsection and a most proximal subsection. The plurality of subsections may be connected in a linear arrangement. Each subsection may be pivotally moveable relative to an adjacent subsection. Each subsection may include a plurality of openings provided around its center. The main anchor assembly may be provided between the instrument and the most distal subsection of the bendable section. The main anchor assembly may include a main expandable member connected to the first main pressure cavity. The main expandable member maybe configurable to expand radially outwards upon receiving a positive pressure from the first main pressure cavity. Regarding the plurality of tendon members, each tendon member may be housed in one of the movement cavities. A distal end of each tendon member may be in communication with (e.g., connected to or passed through) at least one of the subsections of the bendable section in such a way that a distal end of the bendable section is configurable to bend when a force is applied to one of the tendon members. The outer assembly may house a portion of the main assembly. The outer assembly may include a proximal end, a distal end, and an outer anchor assembly. The outer anchor assembly may be provided at the distal end of the outer assembly. The outer anchor assembly may include an outer expandable member and a first outer pressure opening. The outer expandable member may be connected to the first outer pressure cavity. The outer expandable member may be configurable to expand radially outwards upon receiving a positive pressure from the first outer pressure cavity. The first outer pressure opening may be connected to the second outer pressure cavity. The first outer pressure opening may be provided adjacent to the outer expandable member. The first outer pressure opening may be selectively configurable to apply a negative pressure (e.g., a suction force inwards from an exterior of the outer assembly towards the outer suction opening) and/or a positive pressure. Each tendon member may extend through one of the subsection openings of the most proximal subsection. A distal end of each tendon member may be in communication with (e.g., connect to or pass through) a location of the most distal subsection that is aligned to the subsection opening of the most proximal subsection that received the tendon member. At least a distal end of the bendable section may be configurable to bend when a force is applied to one of the tendon members.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 2D is an illustration of a side view of an example embodiment of the endoscopic system;

FIG. 2E is an illustration of a side view of an example embodiment of the endoscopic system;

FIG. 3E is an illustration of a side view of an example embodiment of the endoscopic system, and the first main body bending based on the bend in the cavity of the patient;

FIG. 6A is an illustration of a side view of an example embodiment of a main assembly of an endoscopic system;

FIG. 6B is an illustration of a side view of an example embodiment of an outer assembly of an endoscopic system;

FIG. 6G is a cross-sectional view of an example embodiment of an outer assembly of an endoscopic system;

FIG. 6H is a cross-sectional view of an example embodiment of an outer assembly of an endoscopic system;

FIG. 6I is a side view of an example embodiment of an endoscopic system having expandable members in the non-expanded state;

FIG. 6J is a side view of an example embodiment of an endoscopic system having an expandable member of the outer assembly in the expanded state;

FIG. 6K is a side view of an example embodiment of an endoscopic system having an expandable member of the main assembly in an expanded state;

FIG. 6L is a side view of an example embodiment of an endoscopic system having two expandable members in an expanded state;

FIG. 6N is a side view of an example embodiment of an endoscopic system having its bendable section configured in a bended position;

FIG. 6R is a cross-sectional view of another example embodiment of a main assembly of an endoscopic system having an extendible section configured in a normal or un-extended configuration;

FIG. 6S is a cross-sectional view of another example embodiment of a main assembly of an endoscopic system having an extendible section configured in an extended configuration;

FIG. 7A is an illustration of a side view of another example embodiment of a main assembly of an endoscopic system;

FIG. 7B is an illustration of a side view of another example embodiment of an outer assembly of an endoscopic system;

FIG. 8A is an illustration of an example embodiment of a surgical system inserted into a cavity of a patient;

FIG. 8B is an illustration of an example embodiment of a surgical system further inserted into the cavity of the patient;

FIG. 8C is an illustration of an example embodiment of a surgical system inserted into the cavity of the patient and having its bendable section configured in a bended position to advance around a flexural, looping, and/or bending sections of the cavity of the patient;

Although similar reference numbers may be used to refer to similar elements in the figures for convenience, it can be appreciated that each of the various example embodiments may be considered to be distinct variations.

Figure 1:
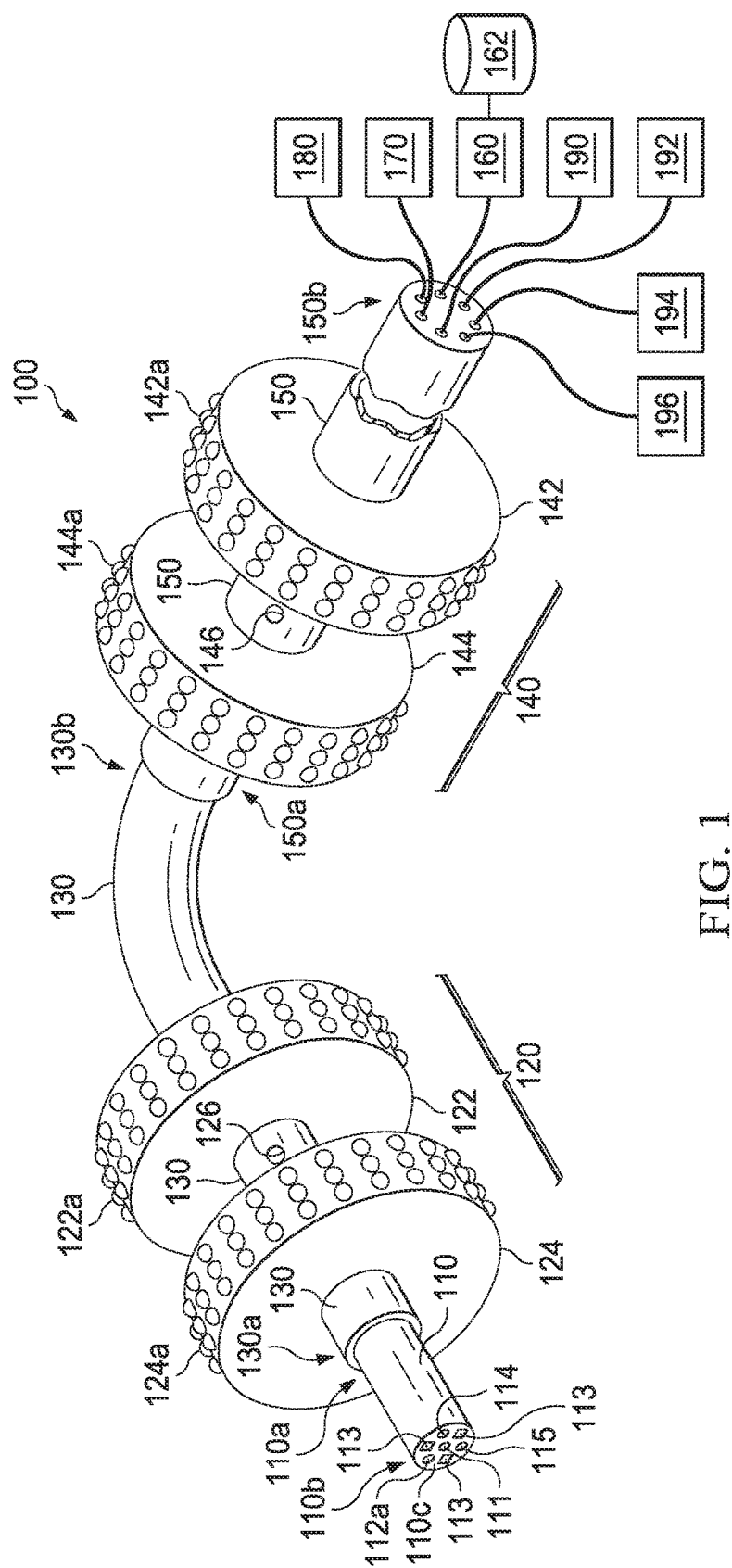
FIG. 1 is an illustration of a perspective view of an example embodiment of an endoscopic system.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

It is recognized in the present disclosure that one or more problems are encountered in colonoscopy-related diagnostic and therapeutic technologies and methodologies, including those described above and in the present disclosure. For example, conventional optical colonoscopy generally involves an insertion of a colonoscope through a colon of a patient, and requires forceful manual pushing of the colonoscope against the interior luminal walls forming the colon cavity at flexural or looping/bending sections of the colon during insertion, which generally results in severe discomfort and/or pain to the patient. Furthermore, the retracting and/or removal of the colonoscope, including the traversing of the colonoscope through the flexural and/or looping/bending sections of the colon of the patient, may also give rise to discomfort and/or pain to the patient.

Recent developments in diagnostic procedures and devices have attempted to address the aforementioned problem through the use of a miniaturized wireless capsule having an integrated camera. To perform the diagnostic procedure, the miniaturized capsule is orally introduced into a patient, and the miniaturized capsule passively navigates via peristalsis along the gastrointestinal tract in a painless manner. It is recognized in the present disclosure, however, that while such recent developments address the issue of discomfort and pain to patients, such recent developments are not without its own problems and limitations. For example, the in vivo monitoring of the gastrointestinal tract by such miniaturized capsules is in fact performed in a non-controlled and very slow manner since locomotion of the miniaturized capsule through the gastrointestinal tract occurs via peristalsis. Furthermore, while a miniaturized capsule generally takes between about 20 to 36 hours to travel through an entire gastrointestinal tract, current power capacity and consumption of such miniaturized capsules are only capable of roughly about eight hours of operation. Accordingly, not all of the gastrointestinal tract can be imaged and/or monitored using such technology. Furthermore, such miniaturized capsules are merely capable of performing imaging/diagnosing procedures, and not capable of performing therapeutic/surgical procedures, such as a removing of polyps, obtaining biopsy samples, and/or the like.

Systems, devices, and methods, including those for use in endoscopy and colonoscopy, are described in the present disclosure for addressing one or more problems of known systems, devices, and methods, including those described above and in the present disclosure. It is to be understood that the principles described in the present disclosure may be applied outside of the context of endoscopy and colonoscopy, such as performing diagnostic procedures, surgical or therapeutic procedures, scientific experiments, and/or other procedures in the same and/or other environments, cavities, and/or organs not described in the present disclosure without departing from the teachings of the present disclosure.

The Endoscopic System (e.g., Endoscopic System 100)

FIG. 1 illustrates a perspective view of an example embodiment of an endoscopic system 100. The endoscopic system 100 may comprise a head assembly 110. The endoscopic system 100 may further comprise a main body 130. The main body 130 may be attachable to the head assembly 110. For example, a first end 130a of the main body 130 may be fixedly attached to a first end portion 110a of the head assembly 110. The endoscopic system 100 may further comprise an anchor assembly 120. The anchor assembly 120 may be attachable to the main body 130. For example, the anchor assembly 120 may be fixedly attached to the main body 130 near the first end 130a of the main body 130. The endoscopic system 100 may further comprise a second main body 150. The second main body 150 may house at least a portion of the main body 130, and the main body 130 and the second main body 150 may be slidable with respect to one another. In this regard, the second main body 150 may comprise a main cavity, and the main cavity may perform the said housing of the main body 130. The endoscopic system 100 may further comprise a second anchor assembly 140. The second anchor assembly 140 may be attachable to the second main body 150. For example, the second anchor assembly 140 may be fixedly attached to the second main body 150 near the first end 150a of the second main body 150. These and other elements of the endoscopic system 100 will now be described with reference to FIGS. 1 to 5.

The Head Assembly (e.g., Head Assembly 110)

FIG. 1 and FIGS. 2A-C illustrate an example embodiment of the head assembly 110 of the endoscopic system 100. The head assembly 110 may comprise first end portion 110a and second end portion 110b opposite to the first end portion 110a. The first end portion 110a of the head assembly 110 may be attachable to the first end 130a of the main body 130 in example embodiments. During diagnostic and/or therapeutic/surgical procedures, the first end portion 110a may be fixedly attached to the first end 130a of the main body 130, as illustrated in at least FIGS. 1 to 3. It is to be understood in the present disclosure that example embodiments of the endoscopic system 100 may comprise one or more other head assemblies, such as head assembly 110' illustrated in FIG. 2B, fixedly attached to one or more other portions of the endoscopic system 100 in addition to or in replacement of the head system 110 attached to the first end 130a of the main body 130.

Figure 2A:
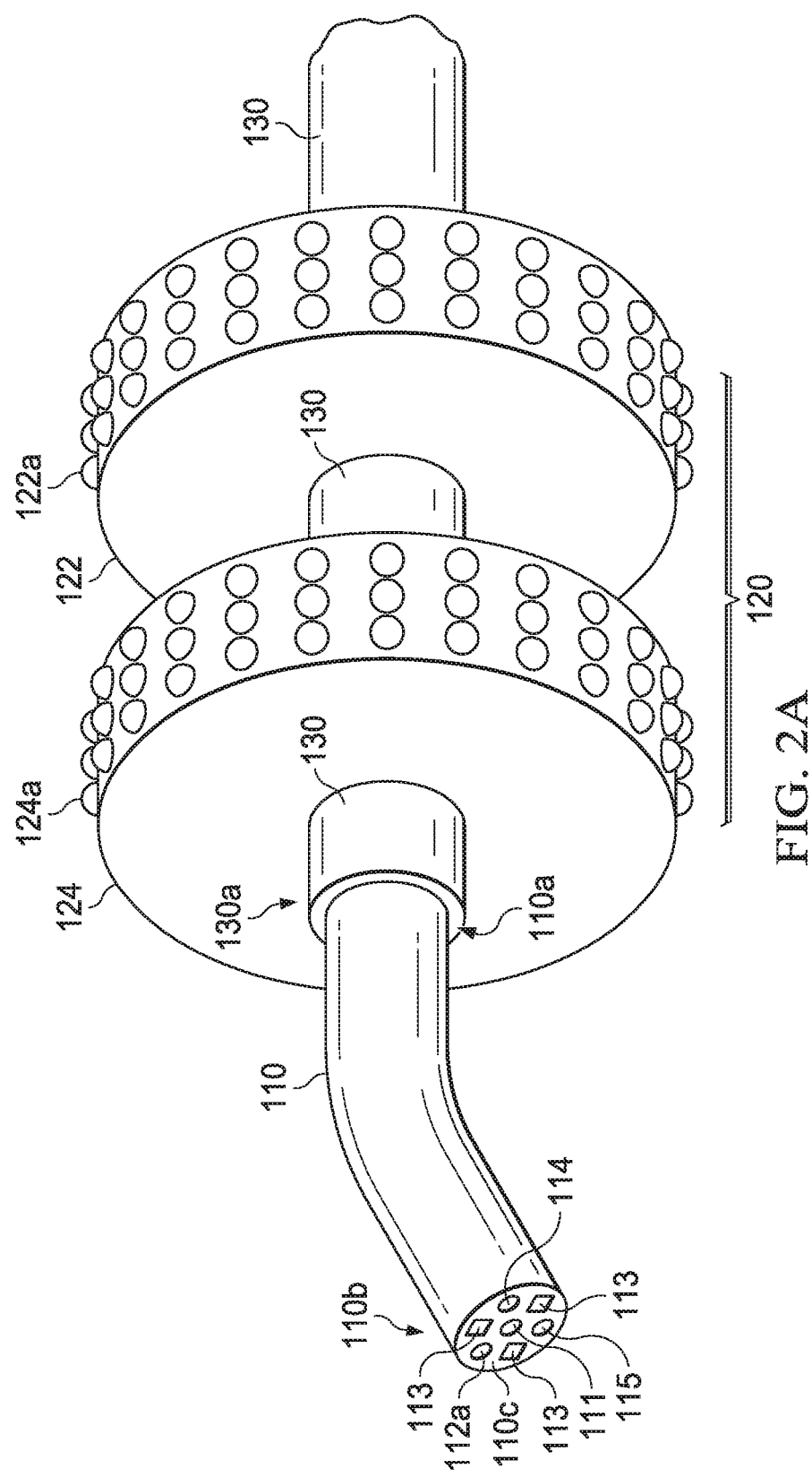
FIG. 2A is an illustration of a perspective view of an example embodiment of the head assembly.

The head assembly 110 may comprise one or more image capturing assemblies 111, as illustrated in at least FIGS. 1 and 2A. Each image capturing assembly 111 may be any image capturing device, such as a digital and/or analog camera, digital and/or analog video camera, three dimensional (3-D) digital and/or analog camera, 3-D digital and/or analog video camera, holographic camera, x-ray based device, infrared-based device, and/or the like. Each image capturing assembly 111 may comprise one or more lenses, or the like, and may be configurable to zoom in and/or out either optically and/or digitally. Furthermore, each image capturing assembly 111 may be configurable to move in one or more directions and/or positions with respect to the head assembly 110, and may also protrude outwardly and/or retract inwardly with respect to the head assembly 110. In an example embodiment, the image capturing assembly 111 may be housed, either in part or in whole, in one or more portions of the endoscopic system 100, such as the head assembly 110.

Each image capturing assembly 111 may further comprise one or more illumination or light sources, such as an LED light source, optical fiber, and/or the like. It is to be understood in the present disclosure that each illumination source may be located together with and/or separate from the image capturing assembly 111 in example embodiments so as to improve illumination of the interior cavity of the patient. For example, in example embodiments, each illumination source may be provided as one or more illumination sources on the face 110c of the head assembly 110, one or more illumination sources distributed and/or continuously shaped around the perimeter of the face 110c of the head assembly 110 (such as a ring-shaped illumination source when the face 110c of the head assembly 110 has a circular shape), etc.

Each image capturing assembly 111 and/or each light source may receive power from a power source (not shown), and/or the like, and such power may be received via wires and/or wirelessly. In an example embodiment, the power source may be housed, either in part or in whole, in one or more portions of the endoscopic system 100, such as the head assembly 110, the main body 130, and/or the second main body 150, and/or provided outside of the patient (such as separate power source 180 and/or power obtained from controller 160).

Each image capturing assembly 111 may be configurable to provide captured/recorded images (such as still images and/or video images, hereinafter "captured images") to a controller 160, computer-readable medium 162, and/or the like, and such captured images may be received by the controller 160 and/or computer-readable medium 162 via wires and/or wirelessly. An operator/surgeon performing a diagnostic, therapeutic, and/or surgical procedure using the endoscopic system 100 may be operable to receive and view the captured images in real-time and/or near real-time via the controller 160, and such captured images may also be stored in the computer-readable medium 162 for viewing at a later time as well. In example embodiments, the operator/surgeon may perform, among other things, one or more of the following using the captured images of the image capturing assembly 111: one or more insertions of a portion of the endoscopic system 100 into the cavity of the patient; one or more anchoring of the anchor assembly 120 and/or second anchor assembly 140; one or more advancing of the main body 130 and/or second main body 150; a straightening of one or more flexural or looping/bending sections of the cavity of the patient; illumination of one or more portions of the cavity of the patient via the light source of the head assembly 110; one or more diagnostic, therapeutic, and/or surgical procedures using one or more of the instruments 112; one or more other procedures and operations of the endoscopic system 100, or parts thereof; etc.

In an example embodiment, the controller 160 and/or computer-readable medium 162 may be housed, either in part or in whole, in one or more portions of the endoscopic system 100, such as the head assembly 110, the main body 130, and/or the second main body 150, and/or provided outside of the patient (as illustrated in at least FIG. 1). The controller 160 may be any device operable to communicate with one or more elements of endoscopic system 100, and may include a computing device, communication device, processor, virtual machine, computer, node, instance, host, server, client, chip/microchip, and/or machine, including combinations thereof and/or those in a networked computing environment. The controller 160 may comprise logic stored in non-transitory computer readable medium, such as computer readable medium 162, which, when executed by the controller 160 and/or a processor of or associated with the controller 160, is operable to perform one or more actions, operations, configurations, and/or communications with one or more elements of the endoscopic system 100, including those described above and in the present disclosure. For example, the controller 160 may be operable to, among other things, communicate with and/or configure one or more of: the computer-readable medium 162, the image capturing assembly 111, instrument 112, movement control cavity 113, irrigation cavity 114, insufflation cavity 115, second end portion 110b, first end portion 110a, head assembly 110, first end 130a, main body 130, movement control cavity 133, irrigation cavity 134, insufflation cavity 135, anchor cavities 136, first end 150a, second main body 150, anchor cavities 154, first expandable member 124, second expandable member 122, first anchor assembly 120, third expandable member 144, fourth expandable member 142, second anchor assembly 140, first suction opening 126, second suction opening 146, pressure control subsystem 170, etc.

Figure 2B:
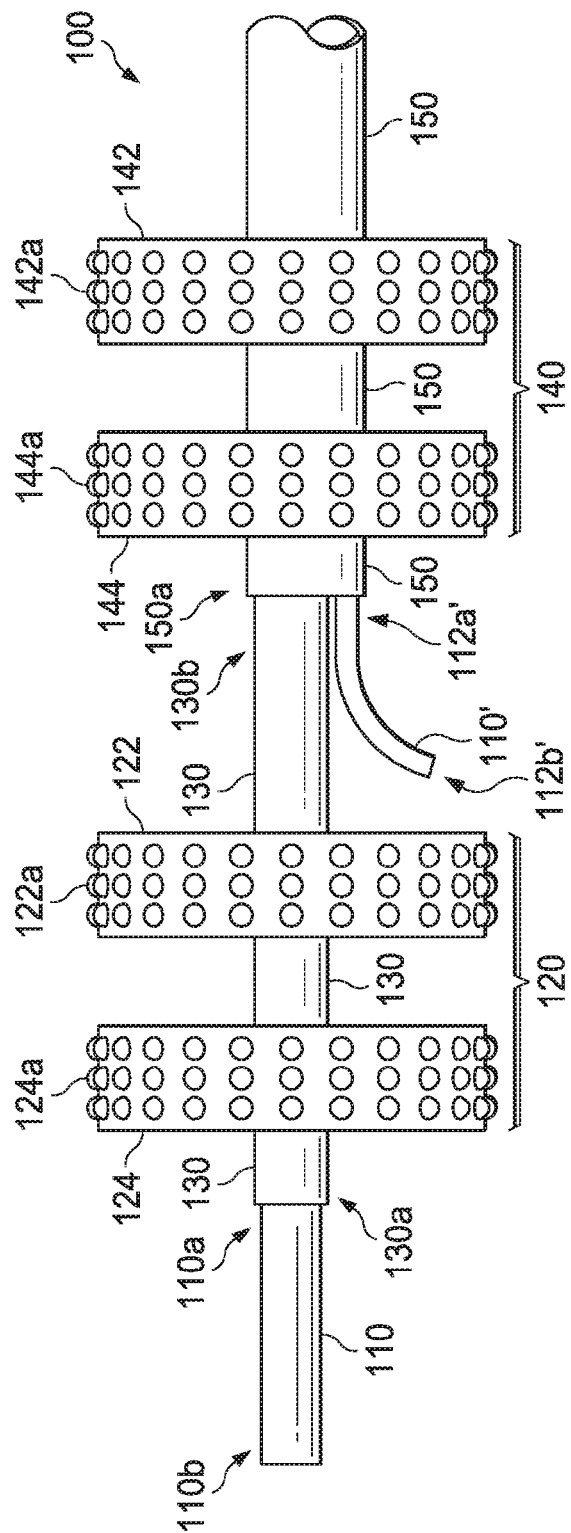
FIG. 2B is an illustration of a side view of an example embodiment of the endoscopic system.
Figure 2C:
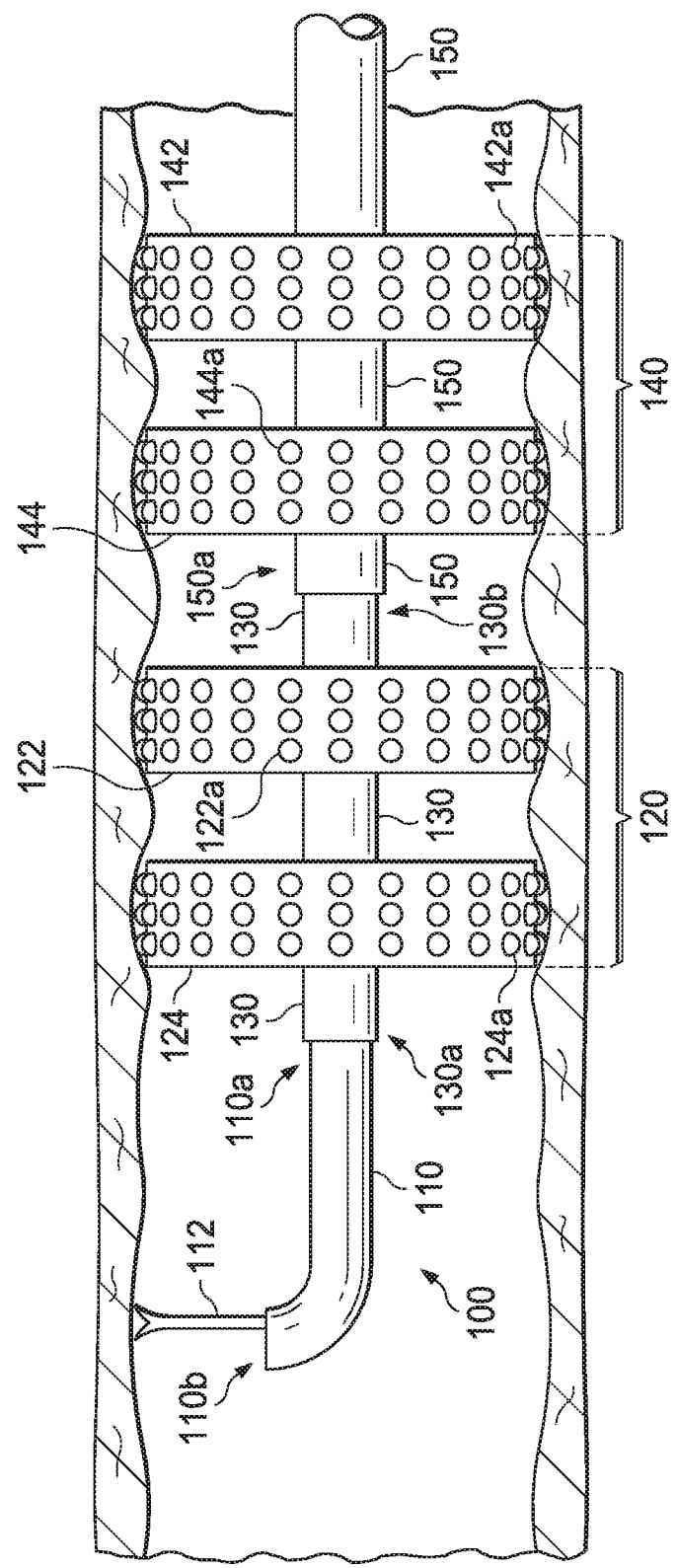
FIG. 2C is an illustration of a side view of an example embodiment of the endoscopic system in a cavity, such as a colonic lumen, of a patient.

As illustrated in at least FIG. 2C, the head assembly 110 may further comprise one or more instruments 112. Each instrument 112 may be any one or more surgical instruments, or the like, for use in performing a diagnostic, therapeutic, and/or surgical procedure, and/or obtaining samples. For example, each instrument 112 may include one or more biopsy forceps, miniaturized manipulator, snare, and/or the like. In example embodiments, the one or more instruments 112 may be housed in one or more portions of the endoscopic system 100, such as in the head assembly 110, the main body 130, the second main body 150, and/or outside of the cavity of the patient. When needed, the one or more instruments 112 may be provided through an instrument cavity or channel 112a (see FIGS. 1 and 2A), and may also be provided outwardly (as illustrated in at least FIG. 2C) and/or retracted inwardly with respect to the head assembly 110. In example embodiments, the instrument 112 may be configurable to have one or more degrees of freedom (DOF) of movement. The one or more instruments 112 may be configured and/or controlled by the controller 160 and/or an operator/surgeon, either manually and/or via the controller 160, in example embodiments. Furthermore, one or more movements and/or positions of the instrument(s) 112 may be stored in the computer-readable medium 162.

At least a portion of the head assembly 110, such as the second end portion 110b, may be selectively configurable to actuate (including bending, turning, pivoting, twisting, moving, etc., hereinafter "actuate") in one or more of a plurality of directions (and/or positions, locations, and/or the like) with respect to one or more points/areas, such as the first end portion 110a and/or other portions of the head assembly 110 and/or endoscopic system 100. For example, the second end portion 110b may be selectively configured and/or controlled to actuate (bend) in a plurality of directions, such as the bending illustrated in at least FIG. 3D FIGS. 2A and 2C. The second end portion 110b may also be selectively configured and/or controlled to actuate (extend outwardly and/or retract inwardly) with respect to one or more points/areas, such as the first end portion 110a of the head assembly 110 and/or other portions of the head assembly 110 and/or endoscopic system 100, as illustrated in at least FIG. 2D and FIG. 2E. Furthermore, the head assembly 110 may be capable of at least two degrees of freedom (DOF) of movement, including a pitch and yaw movement. In example embodiments, each degree of freedom may have a bending angle of at least 110 degrees.

It is recognized in the present disclosure that actuating of at least a portion of the head assembly 110 may assist in enabling the endoscopic system 100 to advance around flexural and/or looping/bending sections of the cavity of the patient without forceful manual pushing against the interior wall forming the cavity, such as the colonic lumen, of the patient. It is further recognized in the present disclosure that actuating of at least a portion of the head assembly 110, including those described above and in the present disclosure, may enable the one or more image capturing assemblies 111 to improve image capturing capabilities. Furthermore, actuating of at least a portion of the head assembly 110, including those described above and in the present disclosure, may enable the one or more illumination sources to provide improved illumination to specific areas within the cavity of the patient. Furthermore, actuating of at least a portion of the head assembly 110, including those described above and in the present disclosure, may enable the one or more instruments 112 to more readily access and/or perform diagnostic, therapeutic, and/or surgical procedures, including obtaining samples, within the cavity of the patient and/or an interior wall forming the cavity of the patient.

The at least one portion of the head assembly 110 may be selectively configurable to actuate in one or more of a plurality of directions using one or more elements of the endoscopic system 100 and/or one or more methods described below and in the present disclosure. In an example embodiment, the head assembly 110 may comprise one or more movement control cavities 113, or the like. Each movement control cavity 113 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the head assembly 110, such as the second end portion 110b of the head assembly 110, in a specific desired direction and/or position, a predetermined selection and/or combination of one or more of the movement control cavities 113 may be selectively configured and controlled. For example, one or more of the movement control cavities 113 may house one or more types of fillers, and such fillers may be manipulated, manually by operator/surgeon and/or via controller 160, to actuate the portion of the head assembly 110. As another example, one or more of the movement control cavities 113 may be provided with a predetermined quantity of one or more types of fillers when actuating of the portion of the head assembly 110 is required. As another example, the properties of the filler material housed in one or more of the movement control cavities 113 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, the one or more fillers may be a material (or combination of materials) selected in such a way that an introduction, application, and/or removal of an application, each as applicable, of an electric current, voltage potential, resistance, pressure, temperature, magnetic field, and/or the like, causes and/or controls one or more of the above-mentioned changes in properties. For example, the filler may be a memory-shaped metal or other material, or the like.

In example embodiments, the actuating of the head assembly 110, including the second end portion 110b of the head assembly 110, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 113 may be stored in the computer-readable medium 162.

It is to be understood in the present disclosure that very small/minute, precise/accurate, quick, and firm movements of the second end portion 110b of the head assembly 110, as well as the instrument(s) 112, image capturing assembly 111, and/or other portions of the endoscopic system 100, may be achievable using the aforementioned elements of the endoscopic system 100 and/or methods. It is also to be understood in the present disclosure that other elements and/or methods for actuating a movement, control, and/or position of a portion of the head assembly 110, such as one or more sensors (such as motion sensors, proximity sensors, distance sensors, etc.), are contemplated without departing from the teachings of the present disclosure. Furthermore, it is recognized in the present disclosure that movement, positioning, and/or controlling of other elements of the endoscopic system, including one or more of the instrument 112, main body 130, second main body 150, head assembly 110', and/or other elements of the endoscopic system 100 may also be based on, performed, and/or controlled in a similar and/or substantially the same manner as described above for the head assembly 110 in example embodiments.

As illustrated in at least FIGS. 1 and 2A, the head assembly 110 may further comprise one or more irrigation cavities 114. Each irrigation cavity 114 may be configurable to provide movement of fluid and/or solids into and/or out of the cavity of the patient via an irrigation subsystem 190. For example, each irrigation cavity 114 in communication with the irrigation subsystem 190 may be operable to introduce a liquid into the cavity of the patient, and each irrigation cavity 114 in communication with the irrigation subsystem 190 may be operable to remove a liquid, such as water, and/or solid, such as polyps, from the cavity of the patient. In example embodiments, the movement of fluid and/or solids into and/or out of the cavity of the patient via the one or more irrigation cavities 114 may be performed and/or controlled by the controller 160 and/or an operator/surgeon, either manually and/or via the controller 160. Furthermore, the amount of such movements of liquid and/or solids into and/or out of the cavity of the patient via the one or more irrigation cavities 114 may be stored in the computer-readable medium 162.

The head assembly 110 may further comprise one or more insufflation cavities 115. Each insufflation cavity 115 may be configurable to provide a gas for use in performing insufflation of the cavity of the patient via an insufflation subsystem 192. In example embodiments, the insufflation of the cavity of the patient via the one or more insufflation cavities 115 may be performed and/or controlled by the controller 160 and/or an operator/surgeon either manually and/or via the controller 160. Furthermore, the amount of such insufflation via the one or more insufflation cavities 115 may be stored in the computer-readable medium 162.

It is to be understood in the present disclosure that the head assembly 110, including one or more of the image capturing assembly 111, illumination source, instrument 112, movement control cavities 113, irrigation cavity 114, irrigation subsystem 190, insufflation cavity 115, and/or insufflation subsystem 192 may be provided in a configuration that is the same as, similar to, based on, or different from that illustrated in the example embodiment of FIGS. 1 and 2A without departing from the teachings of the present disclosure. Furthermore, one or more of the image capturing assembly 111, illumination source, instrument 112, movement control cavities 113, irrigation cavity 114, and insufflation cavity 115 may be provided, or not provided, in the head assembly 110 without departing from the teachings of the present disclosure.

The head assembly 110, and/or cross-section thereof, may be formed in any one of a plurality of shapes, sizes, and/or dimensions. For example, the head assembly 110 may be an elongated cylindrical body, as illustrated in FIGS. 1 and 2A. The cross-sectional shape of the head assembly 110 may also be one or more of a rectangle, square, pentagon, hexagon, etc., or combination of one or more geometric shapes, without departing from the teachings of the present disclosure.

In an example embodiment wherein the shape of the head assembly 110 is cylindrical in shape with a circular cross-section, an outer diameter of the cross-section of the head assembly 110 may be between about 5 to 30 mm. The length of the head assembly 110 may be between about 10 to 100 mm. It is to be understood in the present disclosure that the above dimensions are merely an illustration of example embodiments, and as such the dimensions may be smaller or larger than those recited above without departing from the teachings of the present disclosure.

The head assembly 110 may be formed using any one or more of a plurality of materials, such as surgical-grade plastics, rubbers, etc. The instrument 112 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Main Body (e.g., Main Body 130)

FIG. 1, FIGS. 2A-C, and FIGS. 3A-H illustrate an example embodiment of the main body 130 of the endoscopic system 100. As used in the present disclosure, the main body 130 may also be referred to as the first main body 130, inner body 130, first tube 130, inner tube 130, and/or the like. The main body 130 may comprise a first end 130a and an exposed end portion 130b. The first end 130a of the main body 130 may be attachable to the first end portion 110a of the head assembly 110 in example embodiments. During diagnostic and/or therapeutic/surgical procedures, the first end 130a may be fixedly attached to the first end portion 110a of the head assembly 110, as illustrated in at least FIGS. 1 to 3.

Figure 3A:
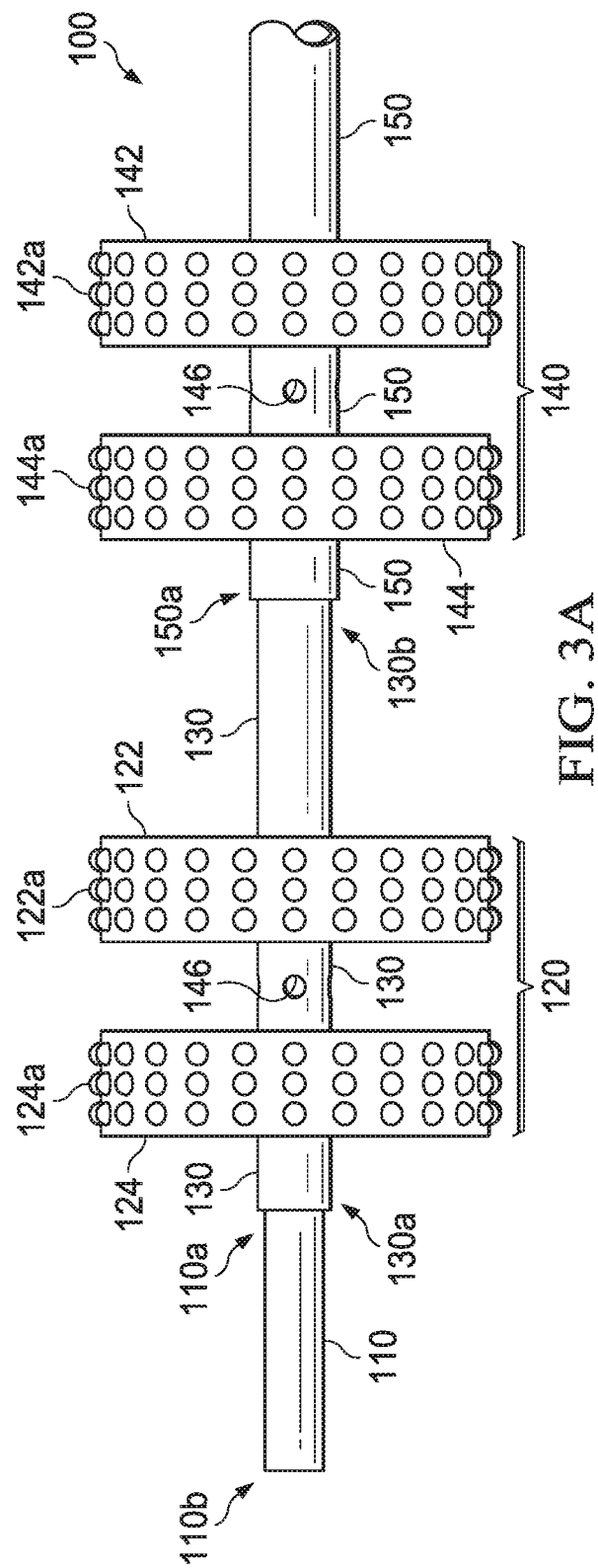
FIG. 3A is an illustration of a side view of an example embodiment of the endoscopic system.
Figure 3B:
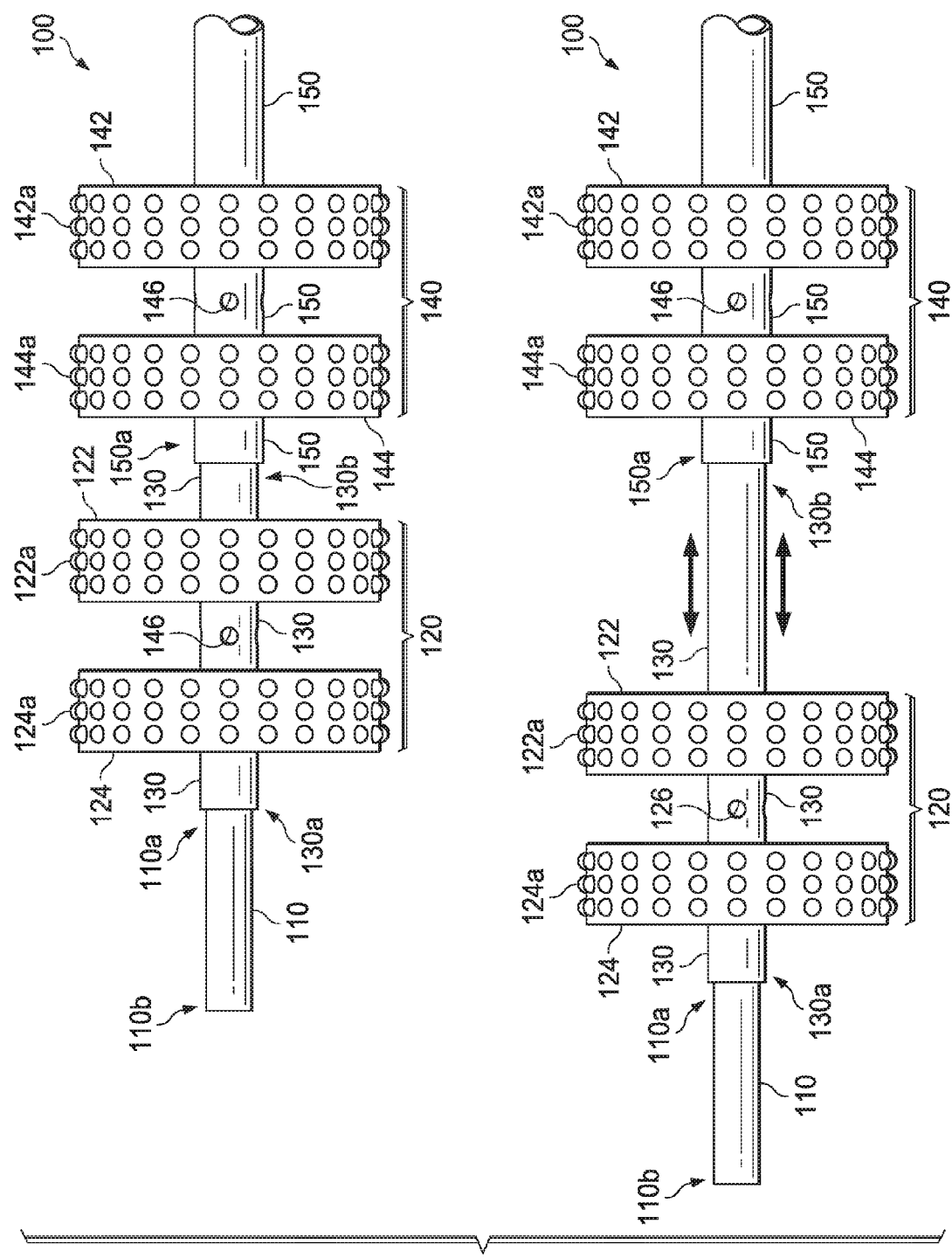
FIG. 3B is an illustration of a side view of an example embodiment of the endoscopic system.

At least a portion of the main body 130 may be selectively configurable to actuate (and/or bend, turn, pivot, twist, move, and/or the like) in one or more of a plurality of directions (and/or positions, locations, and/or the like) with respect to the second main body 150 and/or other portions of the main body 130 and/or endoscopic system 100. Such actuating of a portion of the main body 130 may be similar to, the same as, based on, or different from the actuating described above for the head assembly 110. For example, a portion of the main body 130 closer to the first end 130a may be selectively configured and/or controlled to bend in a plurality of directions, as illustrated in at least FIG. 3E and FIG. 1. The said portion of the main body 130 closer to the first end 130a may also be selectively configured and/or controlled to slide, that is, extend outwardly and/or retract inwardly, with respect to the second main body 150 in example embodiments, as illustrated in FIG. 3B. It is recognized in the present disclosure that sliding and/or actuating of at least a portion of the main body 130 may enable the endoscopic system 100 to advance around flexural and/or looping/bending sections of the cavity of the patient without forceful manual pushing against the interior wall forming the cavity of the patient. Furthermore, actuating of at least a portion of the main body 130 may enable the one or more illumination sources of the head assembly 110 to provide improved illumination to specific areas within the cavity of the patient. Furthermore, actuating of at least a portion of the main body 130 may enable the one or more instruments 112 of the head assembly 110 to more readily access and perform diagnostic, therapeutic and/or surgical procedures, including obtaining samples, within the cavity of the patient.

Figure 3C:
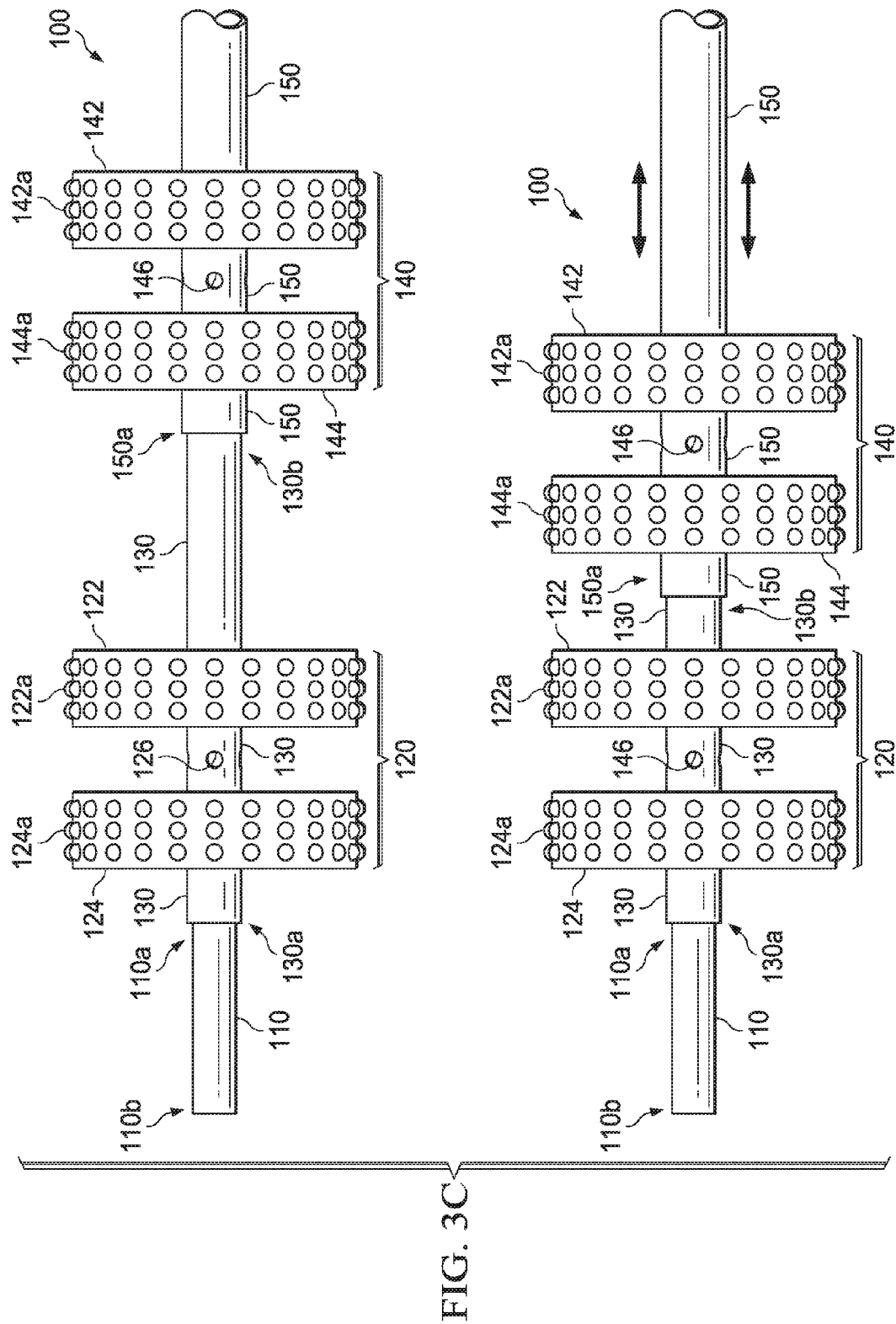
FIG. 3C is an illustration of a side view of an example embodiment of the endoscopic system.

At least one portion of the main body 130 may be selectively configurable to slide with respect to the second main body 150 (as illustrated in FIGS. 3B-C) and/or actuate in one or more of a plurality of directions using one or more elements of the endoscopic system 100 and/or one or more methods, as described below and in the present disclosure. In an example embodiment illustrated in FIG. 3H, the main body 130 may comprise one or more movement control cavities 133, or the like. Each movement control cavity 133 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the main body 130, such as the portion of the main body 130 closer to the first end 130a, in a specific desired direction and/or position, a predetermined selection and/or combination of one or more of the movement control cavities 133 may be selectively configured and controlled. For example, one or more of the movement control cavities 133 may house one or more types of fillers, and such fillers may be manipulated, manually by operator/surgeon and/or via controller 160, to actuate the portion of the main body 130. As another example, one or more of the movement control cavities 133 may be provided with a predetermined quantity of one or more types of fillers when actuating of the portion of the main body 130 is required. As another example, the properties of the filler material housed in one or more of the movement control cavities 133 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape/size, change in tensile strength, etc. To effect one or more such changes, the one or more fillers may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, the filler may be a memory-shaped metal, other material, spring-based or spring-like material, or the like.

In example embodiments, the actuating of the main body 130, including the portion of the main body 130 closer to the first end 130a, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 133 may be stored in the computer-readable medium 162.

It is to be understood in the present disclosure that very small/minute, precise/accurate, quick, and firm movements of the portion of the main body 130 closer to the first end 130a, may be achievable using the aforementioned elements of the endoscopic system 100 and/or methods. It is also to be understood in the present disclosure that other elements and/or methods for actuating a movement, control, and/or position of a portion of the main body 130 and/or other elements of the endoscopic system 100 are contemplated without departing from the teachings of the present disclosure. Furthermore, it is recognized in the present disclosure that movement, positioning, and/or controlling of other elements of the endoscopic system, including one or more of the instrument 112, head assembly 110, second main body 150, and/or other elements of the endoscopic system 100 may also be based on, performed, and/or controlled in a similar and/or substantially the same manner as described above for the main body 130 in example embodiments.

Figure 3D:
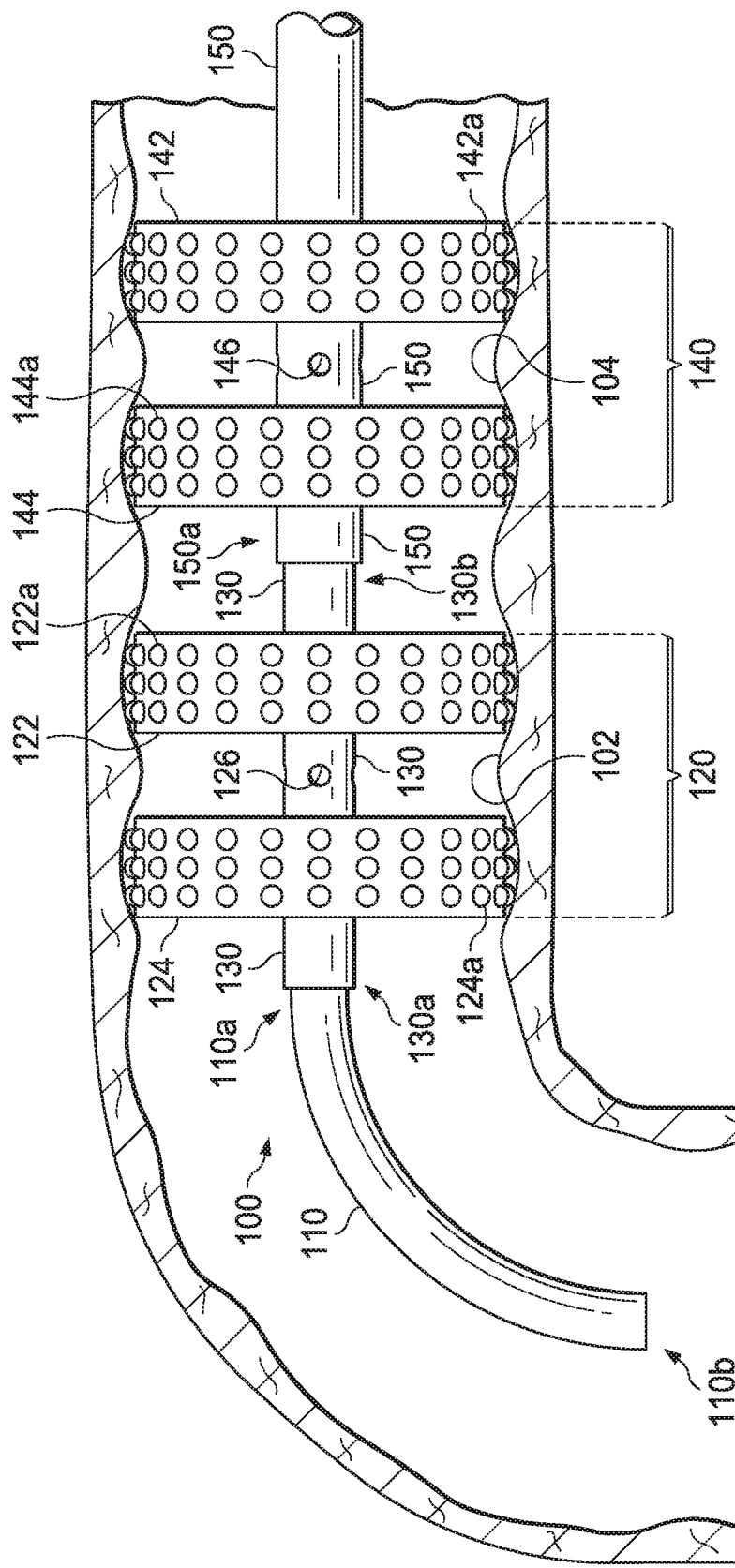
FIG. 3D is an illustration of a side view of an example embodiment of the endoscopic system in a cavity of a patient, and the head assembly bending based on a bend in the cavity of the patient.
Figure 3F:
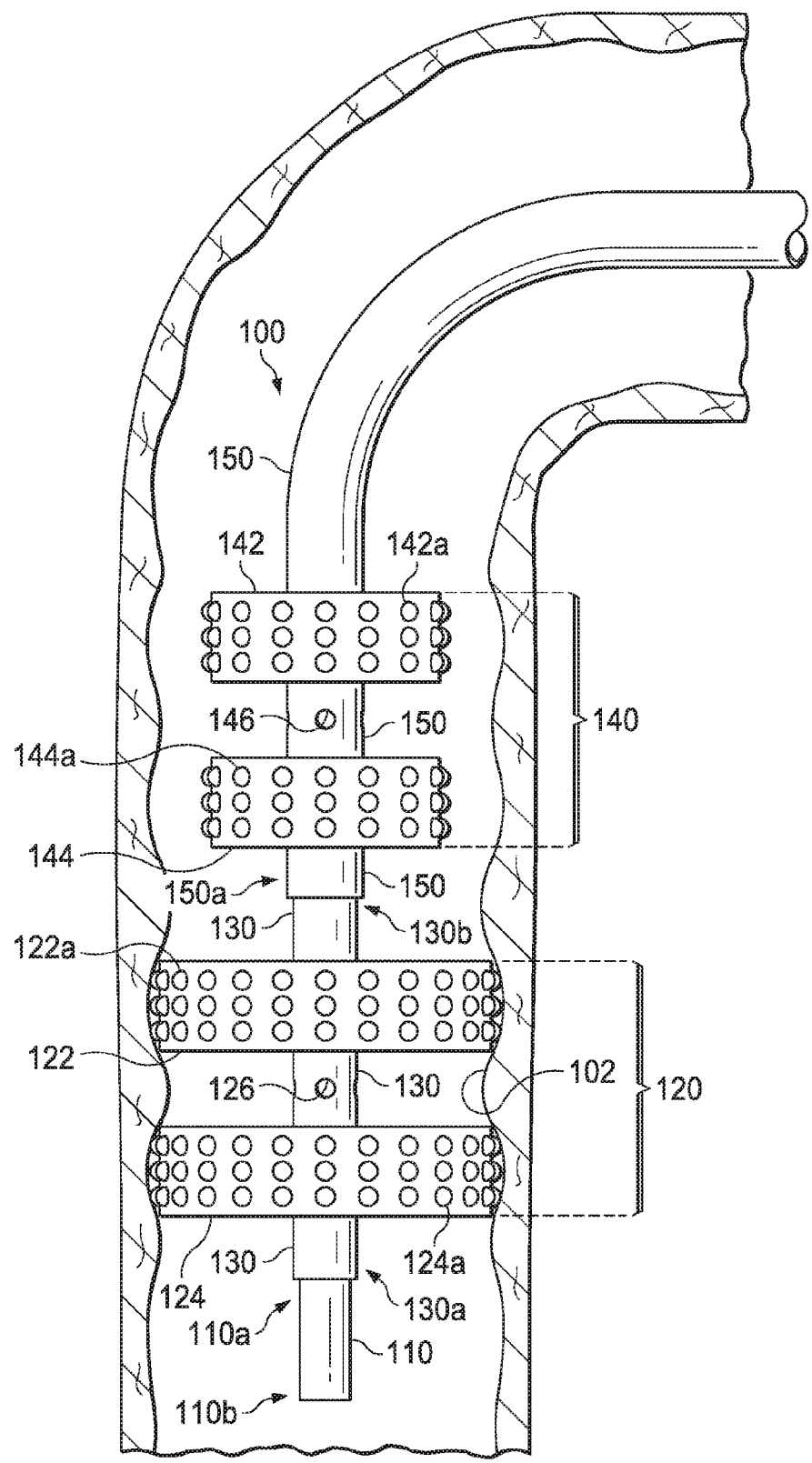
FIG. 3F is an illustration of a side view of an example embodiment of the endoscopic system, and the second main body bending based on the bend in the cavity of the patient.
Figure 3G:
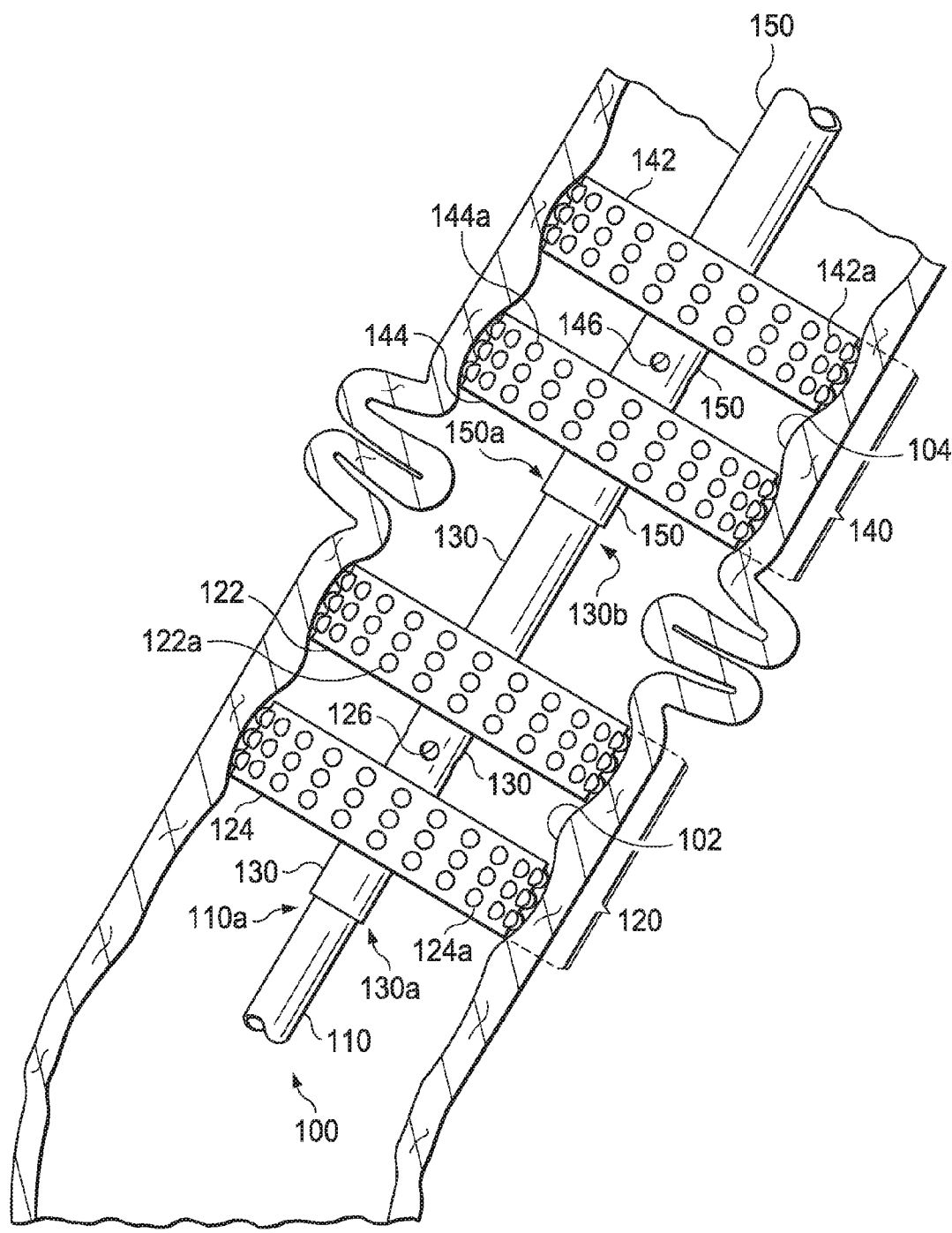
FIG. 3G is an illustration of a side view of an example embodiment of the endoscopic system, and the straightening of the flexural and/or looping/bending section in the cavity of the patient.
Figure 3H:
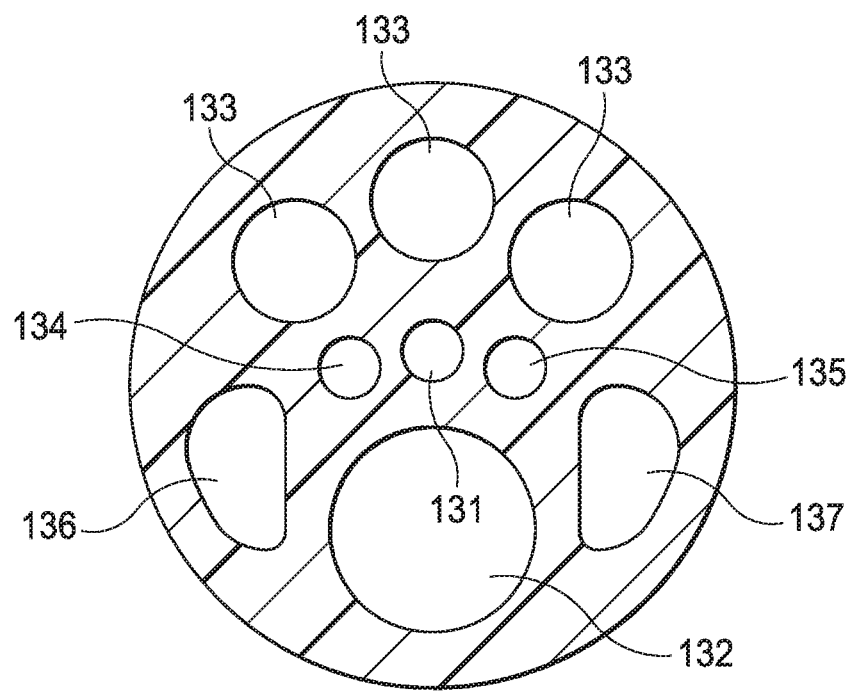
FIG. 3H is an illustration of a cross-sectional view of an example embodiment of the first main body.

As illustrated in at least FIG. 3H, in example embodiments, the main body 130 may further comprise one or more image capturing cavities 131. The image capturing cavity 131 may be operable to enable the image capturing assembly 111 and/or other image capturing assemblies (such as those in head assembly 110') to move with respect to the head assembly 110, and/or enable cables (if any) of the image capturing assembly 111 and/or other image capturing assemblies (such as those in head assembly 110') to be connected to the controller 160 and/or computer-readable medium 162.

As illustrated in at least FIG. 3H, in example embodiments, the main body 130 may further comprise one or more instrument cavities 132. The instrument cavity 132 may be operable to enable the instrument 112 and/or other instruments (not shown) to move with respect to the head assembly (i.e., connected to the instrument cavity 112a), and/or enable cables (if any) and/or connections (if any) of the instrument 112 to be accessible by the operator/surgeon and/or connected to the controller 160 and/or computer-readable medium 162.

As illustrated in at least FIG. 3H, in example embodiments, the main body 130 may further comprise one or more irrigation cavities 134. The irrigation cavity 134 may be operable to enable the movement of fluid and/or solids into and/or out of the cavity of the patient. The irrigation cavity 134 may be connected to the irrigation cavity 114 and/or other irrigation cavities and/or openings (not shown). The irrigation cavity 134 may also be connected to the irrigation subsystem 190 in example embodiments.

As illustrated in at least FIG. 3H, in example embodiments, the main body 130 may further comprise one or more insufflation cavities 135. The insufflation cavity 135 may be operable to provide a gas for use in performing insufflation of the cavity of the patient. The insufflation cavity 135 may or may not be connected to the insufflation cavity 115. The insufflation cavity 135 may also be connected to the insufflation subsystem 192 or a different subsystem in example embodiments.

As illustrated in at least FIG. 3H, in example embodiments, the main body 130 may further comprise one or more anchor cavities 136 operable to configure, control, and/or assist in configuring and/or controlling the anchor assembly 120. The anchor cavity 136 may be operable to provide a gas, liquid, and/or solid, and/or combination thereof, for use in expanding (such as expanding radially from the main body 130) one or more of the first expandable member 122 and the second expandable member 124. The anchor cavity 136 may be connected to one or more of the first expandable member 122 and the second expandable member 124. The anchor cavity 136 may also be connected to an expansion source subsystem 194 in example embodiments. The anchor assembly 120 will be further described below.

As illustrated in at least FIG. 3H, in example embodiments, the main body 130 may further comprise one or more suction cavities 137. The suction cavity 137 may be operable to provide a negative pressure (or perform a removal of gas). For example, the suction cavity 137 may be operable to apply a negative pressure to a region between the first expandable member 122 (when expanded), the second expandable member 124 (when expanded), the interior wall forming the cavity of the patient 102, and the main body 130. The suction cavity 137 may be connected to the suction opening 126. The suction cavity 137 may also be connected to the pressure control subsystem 196 in example embodiments. The suction opening 126 will be further described below.

It is to be understood in the present disclosure that the main body 130, including one or more of the image capturing cavities 131, instrument cavities 132, movement control cavities 133, irrigation cavity 134, irrigation subsystem 190, insufflation cavity 135, insufflation subsystem 192, anchor cavities 136, expansion source subsystem 194, suction cavities 137, and pressure control subsystem 196 may be provided in a configuration that is the same as, similar to, based on, or different from that illustrated in the example embodiment of FIG. 3H without departing from the teachings of the present disclosure. Furthermore, one or more of the image capturing cavities 131, instrument cavities 132, movement control cavities 133, irrigation cavity 134, insufflation cavity 135, anchor cavities 136, and suction cavities 137 may be provided, or not provided, in the main body 130 without departing from the teachings of the present disclosure. It is also to be understood in the present disclosure that one or more of the irrigation subsystem 190, insufflation subsystem 192, expansion source subsystem 194, and pressure control subsystem 196 may be the same or different subsystems in example embodiments.

The main body 130, and cross-section thereof, may be formed in any one of a plurality of shapes, sizes, and/or dimensions. For example, the main body 130 may be an elongated cylindrical body, as illustrated in FIGS. 1 to 3. A cross sectional shape of the main body 130 may also be one or more of a rectangle, square, pentagon, hexagon, etc., or combination of one or more geometric shapes, without departing from the teachings of the present disclosure.

In an example embodiment wherein the cross-sectional shape of the main body 130 is cylindrical in shape with a circular cross-section, an outer diameter of the main body 130 may be between about 5 to 30 mm. The length of the main body 130 may be expanded/contracted between about 50 to 200 cm. It is to be understood in the present disclosure that the above dimensions are merely an illustration of example embodiments, and as such the dimensions may be smaller or larger than those recited above without departing from the teachings of the present disclosure.

The main body 130 may be formed using any one or more of a plurality of materials, such as surgical-grade plastics, rubbers, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Anchor Assembly (e.g., Anchor Assembly 120)

A perspective view of an example embodiment of an expanded anchor assembly 120 (e.g., anchor assembly 120 expanded radially from the main body 130) is illustrated in at least FIG. 1 and FIG. 2A; a side view of an example embodiment of an expanded anchor assembly 120 (e.g., anchor assembly 120 expanded radially from the main body 130) is illustrated in at least FIGS. 2B-C, FIG. 3A, FIG. 3D, and FIGS. 3F-G; and a side view of an example embodiment of an un-expanded anchor assembly 120 (e.g., anchor assembly 120 not expanded radially from the main body 130) is illustrated in at least FIGS. 3B-C. The anchor assembly 120 may be attachable to the main body 130. During diagnostic and/or therapeutic/surgical procedures, the anchor assembly 120 may be fixedly attached to the main body 130 near the first end 130a of the main body 130.

The anchor assembly 120 may be configurable to perform, among other things, a securing of a position and/or location of the main body 130. In an example embodiment, when the endoscopic system 100 is inserted into the cavity of the patient, as illustrated in at least FIG. 2C, FIG. 3D, and FIGS. 3F-G, the anchor assembly 120 may be configurable to secure the main body 130 with respect to the interior wall forming the cavity of the patient. The anchor assembly 120 may secure the main body 130 with respect to the interior wall forming the cavity of the patient in one or more of a plurality of ways. In an example embodiment, one or more expandable members 122, 124 may be expanded to contact the interior walls forming the cavity of the patient. The anchor assembly 120 may also secure the main body 130 with respect to the interior wall forming the cavity of the patient by applying a negative pressure via one or more suction openings 126. The anchor assembly 120 may also secure the main body 130 with respect to the interior wall forming the cavity of the patient via one or more surface patterns, roughness, protrusions, and/or the like formed on a surface, or portion(s) thereof, of one or more expandable members 122, 124. The anchor assembly 120 may also secure the main body 130 with respect to the interior wall forming the cavity of the patient using a magnetic element and corresponding external magnetic element provided outside of the patient. The securing, by the anchor assembly 120, of the main body 130 with respect to the interior wall forming the cavity of the patient will now be further described below.

The anchor assembly 120 may comprise one or more expandable members 122, 124. During diagnostic and/or therapeutic/surgical procedures, the one or more expandable members 122, 124 may be fixedly attached to the main body 130 near the first end 130a of the main body 130. In an example embodiment, the anchor assembly 120 may comprise expandable member 122. As used in the present disclosure, the expandable member 122 may also be referred to as the first expandable member 122, first balloon 122, and/or the like. The anchor assembly 120 may further comprise second expandable member 124. The second expandable member 124 may be provided between the first expandable member 122 and the first end 130a of the main body 130. As used in the present disclosure, the second expandable member 124 may also be referred to as the expandable member 124, second balloon 124, and/or the like. It is to be understood in the present disclosure that the anchor assembly 120 may comprise other quantities of expandable members, such as one or more additional expandable members, without departing from the teachings of the present disclosure.

Each expandable member 122, 124 may be configurable to change its volume/size to be a minimum volume/size, a maximum volume/size, and a volume/size between the minimum and maximum volumes/sizes. For example, each expandable member 122, 124 may be configurable to expand radially away from the main body 130.

In an example embodiment, each expandable member 122, 124 may be a hollow member resembling a balloon, tire, or the like. In this regard, each expandable member 122, 124 may be operable to expand (i.e., secure the main body 130) by receiving a gas (or positive pressure), liquid, solid, and/or combination thereof. The expanding of the expandable member 122, 124 may occur partially, substantially, or completely in a direction away from the main body 130 (i.e., radially away from the main body 130). Furthermore, each expandable member 122, 124 may be operable to reduce in size (or contract or un-secure the main body 130) by removing the gas (or removing the positive pressure or applying a negative pressure), liquid, solid, and/or combination thereof, received in the expandable member 122, 124. To secure the main body 130 with respect to the interior wall forming the cavity of the patient, the one or more expandable members 122, 124 may be expanded to contact the interior wall forming the cavity of the patient. It is recognized in the present disclosure that the expanding and contacting of the one or more expandable members 122, 124 with the interior wall forming the cavity of the patient may provide for a sufficient securing or anchoring of the main body 130 so as to withstand a force of at least 0.1 to 20 N.

One or more of the expandable members 122, 124 may comprise one or more surface patterns, roughness, protrusions, and/or the like formed on a surface, or portion(s) thereof, of the one or more expandable members 122, 124. During diagnostic and/or therapeutic/surgical procedures wherein a securing or anchoring of the main body 130 with respect to the interior wall forming the cavity of the patient is desired or required, such surface patterns, roughness, protrusions, and/or the like formed on the surface of one or more expandable members 122, 124 that are in contact with the interior wall forming the cavity of the patient may further improve the securing or anchoring of the main body 130. For example, the surface pattern, roughness, protrusions, and/or the like may provide, or contribute in providing, resistance of a movement of one or more of the expandable members 122, 124 contacting the interior wall forming the cavity of the patient with respect to the interior wall forming the cavity of the patient. It is recognized in the present disclosure that such securing or anchoring of the main body 130 may be operable to withstand a force of at least 0.1 to 30 N.

It is to be understood in the present disclosure that the anchor assembly 120, including one or more of the first and second expandable members 122, 124, may or may not be a hollow member resembling a balloon, tire, or the like. For example, one or more of the first and second expandable members 122, 124 may only be partially hollow. As another example, one or more of the first and second expandable members 122, 124 may be formed partially, substantially, and/or entirely of an expandable solid and/or liquid. In this regard, the properties of such material forming one or more of the first and second expandable members 122, 124 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, such material forming one or more of the first and second expandable members 122, 124 may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, such material may be a memory-shaped metal, other material, spring-based or spring-like material, or the like.

Figure 4A:
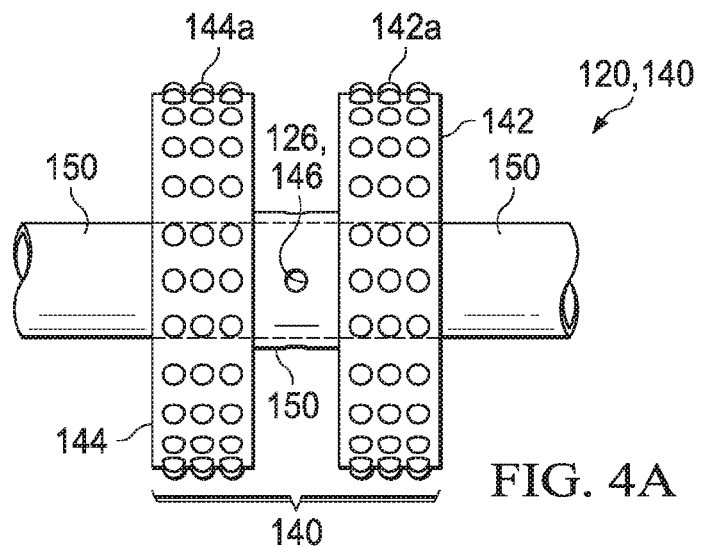
FIG. 4A is an illustration of a side view of an example embodiment of a first and/or second anchor assembly.
Figure 4B:
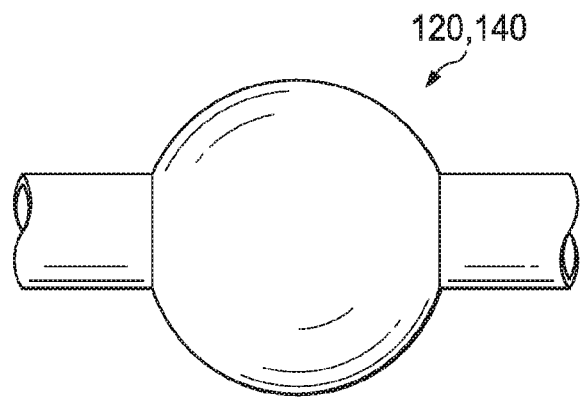
FIG. 4B is an illustration of a side view of another example embodiment of the first and/or second anchor assembly.
Figure 4C:
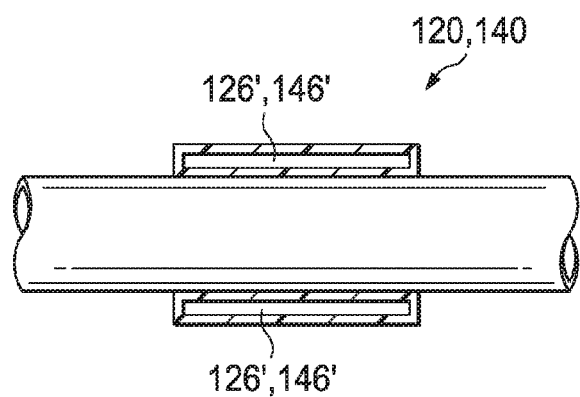
FIG. 4C is an illustration of a side view of another example embodiment of the first and/or second anchor assembly.

In some example embodiments, the anchor assembly 120 may comprise one or more expandable members that expand in one or more other directions in addition to expanding radially away from the main body 130, such as the example illustrated in FIG. 4B. In other example embodiments, such as the example illustrated in FIG. 4A, the anchor assembly 120 may comprise an integrated first and second expandable members 122, 124, or the like. In other example embodiments, such as the example illustrated in FIG. 4C, the anchor assembly 120 may comprise a magnetic element 126', or the like, operable to secure to a corresponding magnetic element provided outside of the patient.

Figure 4D:
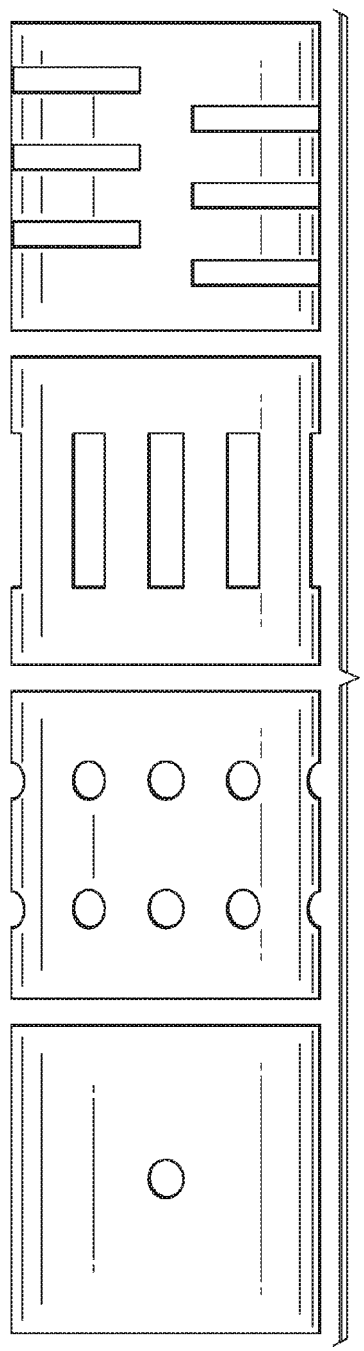
FIG. 4D is an illustration of example embodiments of suction openings.

The anchor assembly 120 may further comprise one or more suction openings 126. As used in the present disclosure, the suction opening 126 may also be referred to as the first suction opening 126. The suction opening 126 may be formed in one or more of a plurality of shapes and provided in one or more quantities. FIG. 4D illustrates example embodiments of the one or more suction openings 126. During diagnostic and/or therapeutic/surgical procedures wherein a securing or anchoring of the main body 130 with respect to the interior wall forming the cavity of the patient is desired or required, the one or more suction openings 126 may further improve the securing or anchoring of the main body 130. For example, the suction opening 126 may be operable to apply a negative pressure to a region between the first expandable member 122 (when expanded), the second expandable member 124 (when expanded), the interior wall forming the cavity of the patient 102 (as illustrated in at least FIG. 3F), and the main body 130. In example embodiments, the suction opening 126 may be configurable to apply a negative pressure and vary the applied negative pressure between about −10 kPa to vacuum. It is recognized in the present disclosure that such securing or anchoring of the main body 130 with the use of the expanded first and second expandable members 122, 124 and the one or more suction openings 126 may provide improved securing or anchoring, and may be operable to withstand a force of at least 0.1 to 40 N.

In example embodiments, the applying of the negative pressure by the suction opening 126 (i.e., the suctioning or removal of gas from the region between the first expandable member 122 (when expanded), the second expandable member 124 (when expanded), the interior wall forming the cavity of the patient 102, and the main body 130) may be performed prior to, at the same time as (or correspond with), and/or after the expansion of the expandable members 122, 124. Furthermore, in example embodiments, the applying of the negative pressure by the suction opening 126 (i.e., the suctioning or removal of gas from the region between the first expandable member 122 (when expanded), the second expandable member 124 (when expanded), the interior wall forming the cavity of the patient 102, and the main body 130) may be operable to provide, or contribute in providing, the expanding of one or more of the expandable members 122, 124. For example, as the gas in the region between the first expandable member 122 (when expanded), the second expandable member 124 (when expanded), the interior wall forming the cavity of the patient 102, and the main body 130 is being suctioned or removed, the said suctioned or removed gas may be provided into one or more of the expandable members 122, 124. In such an example, a filter, or the like, may be provided to remove unwanted particles, liquid, and/or gas from entering and/or exiting the expandable members 122, 124.

It is to be understood in the present disclosure that, in example embodiments wherein the anchor assembly 120 comprises more than two expandable members, the suction openings 126 may be provided between some or all of the expandable members. For example, if the anchor assembly 120 comprises three expandable members, then suction openings 126 may be provided between each of the three expandable members.

Each expandable member 122, 124, and cross-section thereof, may be formed in any one of a plurality of shapes, sizes, and/or dimensions. For example, the expandable members 122, 124 may resemble a tablet or donut shape with a circular cross-section. A cross sectional shape of the expandable members 122, 124 may also be one or more of a rectangle, square, pentagon, hexagon, etc., or combination of one or more geometric shapes, without departing from the teachings of the present disclosure.

In an example embodiment wherein the cross-sectional shape of the expandable members 122, 124 is circular, an outer diameter of the expandable members 122, 124 may be between about 3 to 100 mm. The distance that the expandable members 122, 124 may be expanded radially away from and contracted towards the main body 130 may be between about 0.05 to 50 mm. It is to be understood in the present disclosure that the above dimensions are merely an illustration of example embodiments, and as such the dimensions may be smaller or larger than those recited above without departing from the teachings of the present disclosure.

The expandable members 122, 124 may be formed using any one or more of a plurality of materials, such as surgical-grade plastics, rubbers, etc. It is to be understood in the present disclosure that the material forming the surface pattern, roughness, and/or protrusion of the surface of the expandable members 122, 124 may be the same as, or different from, the material of the rest of the expandable members 122, 124. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Main Body (e.g., Second Main Body 150)

FIG. 1, FIGS. 2B-C, FIGS. 3A-G, and FIG. 3I illustrate an example embodiment of the second main body 150 of the endoscopic system 100. As used in the present disclosure, the second main body 150 may also be referred to as the outer body 150, second tube 150, outer tube 150, and/or the like. The second main body 150 may comprise a first end 150a and an exposed end portion 150b.

A portion of the main body 130 near the first end 150a may, or may not, be selectively configurable to actuate (and/or bend, turn, pivot, twist, move, and/or the like) in one or more of a plurality of directions (and/or positions, locations, and/or the like) with respect to the other portions of the second main body 150. Such actuating of a portion of the second main body 150 may be similar to, the same as, based on, or different from the actuating described above for the main body 130. The second main body 150 may be selectively configured and/or controlled to slide, that is, extend outwardly and/or retract inwardly, with respect to the main body 130 in example embodiments, as illustrated in FIG. 3C. It is recognized in the present disclosure that sliding and/or actuating of at least a portion of the second main body 150 with respect to the main body 130 may enable the endoscopic system 100 to advance around flexural and/or looping/bending sections of the cavity, such as the colonic lumen, of the patient without forceful manual pushing against the interior wall forming the cavity of the patient.

Figure 3I:
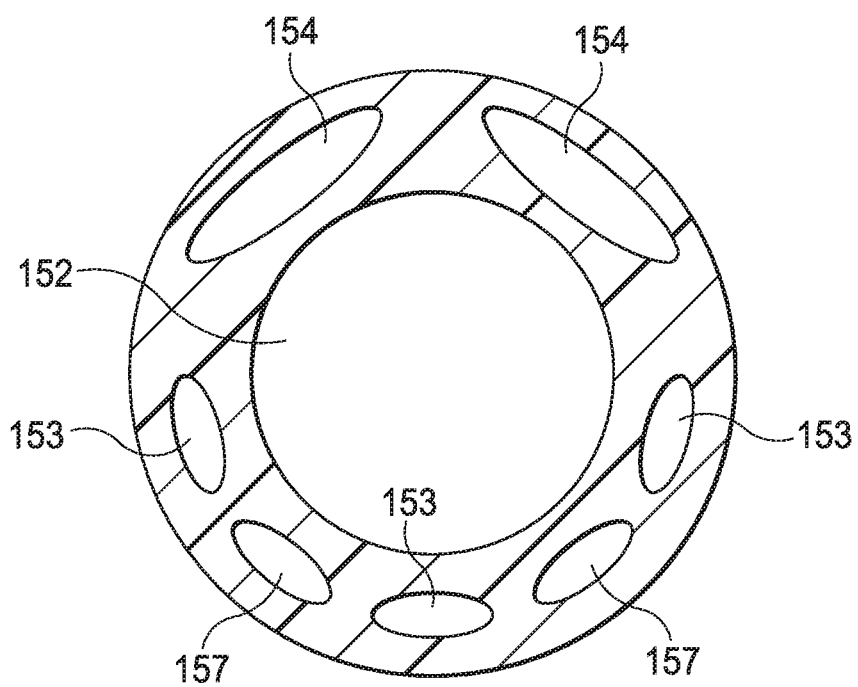
FIG. 3I is an illustration of a cross-sectional view of an example embodiment of the second main body.

In an example embodiment illustrated in FIG. 3I, the second main body 150 may comprise one or more movement control cavities 153, or the like. Each movement control cavity 153 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the second main body 150, such as the portion of the second main body 150 closer to the first end 150a, in a specific desired direction and/or position, a predetermined selection and/or combination of one or more of the movement control cavities 153 may be selectively configured and controlled. For example, one or more of the movement control cavities 153 may house one or more types of fillers, and such fillers may be manipulated, manually by operator/surgeon and/or via controller 160, to actuate the portion of the second main body 150. As another example, one or more of the movement control cavities 153 may be provided with a predetermined quantity of one or more types of fillers when actuating of the portion of the second main body 150 is required. As another example, the properties of the filler material housed in one or more of the movement control cavities 153 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape/size, change in tensile strength, etc. To effect one or more such changes, the one or more fillers may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, the filler may be a memory-shaped metal, other material, spring-based or spring-like material, or the like.

In example embodiments, the actuating of the second main body 150, including the portion of the second main body 150 closer to the first end 150*a*, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 153 may be stored in the computer-readable medium 162.

It is to be understood in the present disclosure that other elements and/or methods for actuating a movement, control, and/or position of a portion of the second main body 150 and/or other elements of the endoscopic system 100 are contemplated without departing from the teachings of the present disclosure.

As illustrated in at least FIG. 3I, in example embodiments, the second main body 150 may further comprise one or more main cavities 152. The main cavity 152 may be operable to enable the main body 130 to move with respect to the second main body 150, and vice versa. Other main cavities 152 may be provided in example embodiments having other main bodies, such as one or more intermediate bodies (not shown) between or adjacent to the main body 130 and the second main body 130. Furthermore, other main cavities 152 may be provided in example embodiments having one or more head assemblies 110', as illustrated in FIG. 2B.

In example embodiments, the second main body 150 may further comprise one or more instrument cavities (not shown). Such instrument cavities of the second main body 150 may be operable to enable instruments, such as instrument 112 and/or other instruments (not shown), to move with respect to the second main body 150, and/or enable cables (if any) and/or connections (if any) of such instruments to be accessible by the operator/surgeon and/or connected to the controller 160 and/or computer-readable medium 162. For example, such instrument cavities of the second main body 150 may be operable to enable an instrument to perform a therapeutic/surgical procedure on a portion of an interior wall forming the cavity of the patient that is between the first anchor assembly 120 and the second anchor assembly 140.

The second main body 150 may further comprise one or more irrigation cavities (not shown). Such irrigation cavity of the second main body 150 may be operable to enable the movement of liquid and/or solids into and/or out of the cavity of the patient. Such irrigation cavity of the second main body 150 may be connected to the irrigation cavity 114, 134 and/or other irrigation cavities and/or openings (not shown). Furthermore, such irrigation cavity of the second main body 150 may also be connected to the irrigation subsystem 190 in example embodiments. In an example embodiment, such irrigation cavity of the second main body 150 may be operable to enable movement of liquid and/or solids into and/or out of the cavity of the patient in an region that is between the first anchor assembly 120 and the second anchor assembly 140.

In example embodiments, the second main body 150 may further comprise one or more insufflation/suction cavities (not shown). Such insufflation/suction cavity of the second main body 150 may be operable to provide and/or remove a gas (i.e., provide a positive pressure and/or a negative pressure, respectively) for use in performing insufflation or suction of the cavity of the patient. Such insufflation/suction cavity of the second main body 150 may or may not be connected to the insufflation cavity 115, 135. Furthermore, such insufflation/suction cavity of the second main body 150 may also be connected to the insufflation subsystem 192, pressure control subsystem, and/or a different subsystem in example embodiments. In an example embodiment, such insufflation/suction cavity of the second main body 150 may be operable to provide insufflation and/or suction in an region that is between the first anchor assembly 120 and the second anchor assembly 140.

As illustrated in at least FIG. 3I, in example embodiments, the second main body 150 may further comprise one or more anchor cavities 154 operable to configure, control, and/or assist in configuring and/or controlling the second anchor assembly 140. The anchor cavity 154 may be operable to provide a gas, liquid, and/or solid, and/or combination thereof, for use in expanding (such as expanding radially from the main body 130) one or more of the third expandable member 142 and the fourth expandable member 144. The anchor cavity 154 may be connected to one or more of the third expandable member 142 and the fourth expandable member 144. The anchor cavity 154 may also be connected to an expansion source subsystem 194 in example embodiments. The second anchor assembly 140 will be further described below.

As illustrated in at least FIG. 3H, in example embodiments, the second main body 150 may further comprise one or more suction cavities 157. The suction cavity 157 may be operable to provide a negative pressure (or perform a removal of gas). For example, the suction cavity 157 may be operable to apply a negative pressure to a region between the third expandable member 142 (when expanded), the fourth expandable member 144 (when expanded), the interior wall forming the cavity of the patient 102, and the second main body 150. The suction cavity 157 may be connected to the suction opening 146. The suction cavity 157 may also be connected to the pressure control subsystem 196 in example embodiments. The suction opening 146 will be further described below.

It is to be understood in the present disclosure that the second main body 150, including one or more of the instrument cavities (not shown), movement control cavities 153, irrigation cavity (not shown), irrigation subsystem 190, insufflation/suction cavity (not shown), insufflation subsystem 192, anchor cavities 154, expansion source subsystem 194, suction cavities 157, and pressure control subsystem 196 may be provided in a configuration that is the same as, similar to, based on, or different from that illustrated in the example embodiment of FIG. 3I without departing from the teachings of the present disclosure. Furthermore, one or more of the instrument cavities (not shown), movement control cavities 153, irrigation cavity (not shown), irrigation subsystem 190, insufflation/suction cavity (not shown), insufflation subsystem 192, anchor cavities 154, expansion source subsystem 194, suction cavities 157, and pressure control subsystem 196 may be provided, or not provided, in the second main body 150 without departing from the teachings of the present disclosure.

The second main body 150, and cross-section thereof, may be formed in any one of a plurality of shapes, sizes, and/or dimensions. For example, the second main body 150 may be an elongated cylindrical body, as illustrated in FIGS. 1 to 3. A cross sectional shape of the second main body 150 may also be one or more of a rectangle, square, pentagon, hexagon, etc., or combination of one or more geometric shapes, without departing from the teachings of the present disclosure.

In an example embodiment wherein the cross-sectional shape of the second main body 150 is cylindrical in shape with a circular cross-section, an outer diameter of the second main body 150 may be between about 6 to 35 mm. The length of the second main body 150 may be expanded/contracted between about 50 to 200 cm. It is to be understood in the present disclosure that the above dimensions are merely an illustration of example embodiments, and as such the dimensions may be smaller or larger than those recited above without departing from the teachings of the present disclosure.

The second main body 150 may be formed using any one or more of a plurality of materials, such as surgical-grade plastics, rubbers, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Anchor Assembly (e.g., Second Anchor Assembly 140)

A perspective view of an example embodiment of an expanded second anchor assembly 140 (e.g., second anchor assembly 140 expanded radially from the second main body 150) is illustrated in at least FIG. 1; a side view of an example embodiment of an expanded second anchor assembly 140 (e.g., second anchor assembly 140 expanded radially from the second main body 150) is illustrated in at least FIGS. 2B-C, FIG. 3A, FIGS. 3D-E, and FIG. 3G; and a side view of an example embodiment of an un-expanded second anchor assembly 140 (e.g., second anchor assembly 140 not expanded radially from the second main body 150) is illustrated in at least FIGS. 3B-C. The second anchor assembly 140 may be attachable to the second main body 150. During diagnostic and/or therapeutic/surgical procedures, the second anchor assembly 140 may be fixedly attached to the second main body 150 near the first end 150*a* of the second main body 150.

The second anchor assembly 140 may be configurable to perform, among other things, a securing of a position and/or location of the second main body 150. In an example embodiment, when the endoscopic system 100 is inserted into the cavity of the patient, as illustrated in at least FIG. 2C, FIGS. 3D-E, and FIG. 3G, the second anchor assembly 140 may be configurable to secure the second main body 150 with respect to the interior wall forming the cavity of the patient. The second anchor assembly 140 may secure the second main body 150 with respect to the interior wall forming the cavity of the patient in one or more of a plurality of ways. In an example embodiment, one or more expandable members 142, 144 may be expanded to contact the interior walls forming the cavity of the patient. The second anchor assembly 140 may also secure the second main body 150 with respect to the interior wall forming the cavity of the patient by applying a negative pressure via one or more second suction openings 146. The second anchor assembly 140 may also secure the second main body 150 with respect to the interior wall forming the cavity of the patient via one or more surface patterns, roughness, protrusions, and/or the like formed on a surface, or portion(s) thereof, of one or more expandable members 142, 144. The second anchor assembly 140 may also secure the second main body 150 with respect to the interior wall forming the cavity of the patient using a magnetic element and corresponding external magnetic element provided outside of the patient. The securing, by the second anchor assembly 140, of the second main body 150 with respect to the interior wall forming the cavity of the patient will now be further described below.

The second anchor assembly 140 may comprise one or more expandable members 142, 144. During diagnostic and/or therapeutic/surgical procedures, the one or more expandable members 142, 144 may be fixedly attached to the second main body 150 near the first end 150*a* of the second main body 150. In an example embodiment, the second anchor assembly 140 may comprise third expandable member 142. As used in the present disclosure, the third expandable member 142 may also be referred to as the expandable member 142, third balloon 142, and/or the like. The second anchor assembly 140 may further comprise fourth expandable member 144. The fourth expandable member 144 may be provided between the third expandable member 142 and the first end 150*a* of the second main body 150. As used in the present disclosure, the fourth expandable member 144 may also be referred to as the expandable member 144, fourth balloon 144, and/or the like. It is to be understood in the present disclosure that the second anchor assembly 140 may comprise other quantities of expandable members, such as one or more additional expandable members, without departing from the teachings of the present disclosure.

Each expandable member 142, 144 may be configurable to change its volume/size to be a minimum volume/size, a maximum volume/size, and a volume/size between the minimum and maximum volumes/sizes. For example, each expandable member 142, 144 may be configurable to expand radially away from the second main body 150.

In an example embodiment, each expandable member 142, 144 may be a hollow member resembling a balloon, or the like. In this regard, each expandable member 142, 144 may be operable to expand (i.e., secure the second main body 150) by receiving a gas (or positive pressure), liquid, solid, and/or combination thereof. The expanding of the expandable member 142, 144 may occur partially, substantially, or completely in a direction away from the second main body 150 (i.e., radially away from the second main body 150). Furthermore, each expandable member 142, 144 may be operable to reduce in size (or contract or un-secure the main body 130) by removing the gas (or removing the positive pressure or applying a negative pressure), liquid, solid, and/or combination thereof, received in the expandable member 142, 144. To secure the second main body 150 with respect to the interior wall forming the cavity of the patient, the one or more expandable members 142, 144 may be expanded to contact the interior wall forming the cavity of the patient. It is recognized in the present disclosure that the expanding and contacting of the one or more expandable members 142, 144 with the interior wall forming the cavity, such as the colonic lumen, of the patient may provide for a sufficient securing or anchoring of the second main body 150 so as to withstand a force of at least 0.1 to 20 N.

One or more of the expandable members 142, 144 may comprise one or more surface patterns, roughness, protrusions, and/or the like formed on a surface, or portion(s) thereof, of the one or more expandable members 142, 144. During diagnostic and/or therapeutic/surgical procedures wherein a securing or anchoring of the second main body 150 with respect to the interior wall forming the cavity of the patient is desired or required, such surface patterns, roughness, protrusions, and/or the like formed on the surface of one or more expandable members 142, 144 that are in contact with the interior wall forming the cavity of the patient may further improve the securing or anchoring of the second main body 150. For example, the surface pattern, roughness, protrusions, and/or the like may provide, or contribute in providing, resistance of a movement of one or more of the expandable members 142, 144 contacting the interior wall forming the cavity of the patient with respect to the interior wall forming the cavity of the patient. It is recognized in the present disclosure that such securing or anchoring of the second main body 150 may be operable to withstand a force of at least 0.10 to 30 N.

It is to be understood in the present disclosure that the second anchor assembly 140, including one or more of the third and fourth expandable members 142, 144, may or may not be a hollow member resembling a balloon, tire, or the like. For example, one or more of the third and fourth expandable members 142, 144 may only be partially hollow. As another example, one or more of the third and fourth expandable members 142, 144 may be formed partially, substantially, and/or entirely of an expandable solid and/or liquid. In this regard, the properties of such material forming one or more of the third and fourth expandable members 142, 144 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, such material forming one or more of the third and fourth expandable members 142, 144 may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, such material may be a memory-shaped metal, other material, spring-based or spring-like material, or the like.

In some example embodiments, the second anchor assembly 140 may comprise one or more expandable members that expand radially away from the second main body 150 and in other directions, such as the example illustrated in FIG. 4B. In other example embodiments, such as the example illustrated in FIG. 4A, the second anchor assembly 140 may comprise an integrated third and fourth expandable members 142, 144, or the like. In other example embodiments, such as the example illustrated in FIG. 4C, the second anchor assembly 140 may comprise a magnetic element 146', or the like, operable to secure to a corresponding magnetic element provided outside of the patient.

The second anchor assembly 140 may further comprise one or more second suction openings 146. As used in the present disclosure, the second suction opening 146 may also be referred to as the suction opening 146. The second suction opening 146 may be formed in one or more of a plurality of shapes and provided in one or more quantities. FIG. 4D illustrates example embodiments of the one or more second suction openings 146. During diagnostic and/or therapeutic/surgical procedures wherein a securing or anchoring of the second main body 150 with respect to the interior wall forming the cavity of the patient is desired or required, the one or more second suction openings 146 may further improve the securing or anchoring of the second main body 150. For example, the second suction opening 146 may be operable to apply a negative pressure to a region between the third expandable member 142 (when expanded), the fourth expandable member 144 (when expanded), the interior wall forming the cavity of the patient 104 (as illustrated in at least FIG. 3E), and the second main body 150. In example embodiments, the second suction opening 146 may be configurable to apply a negative pressure and vary the applied negative pressure between about −10 kPa to vacuum. It is recognized in the present disclosure that such securing or anchoring of the second main body 150 with the use of the expanded third and fourth expandable members 142, 144 and the one or more second suction openings 146 may provide improved securing or anchoring, and may be operable to withstand a force of at least 0.1 to 40 N.

In example embodiments, the applying of the negative pressure by the second suction opening 146 (i.e., the suctioning or removal of gas from the region between the third expandable member 142 (when expanded), the fourth expandable member 144 (when expanded), the interior wall forming the cavity of the patient 104, and the second main body 150) may be performed prior to, at the same time as (or correspond with), and/or after the expansion of the expandable members 142, 144. Furthermore, in example embodiments, the applying of the negative pressure by the second suction opening 146 (i.e., the suctioning or removal of gas from the region between the third expandable member 142 (when expanded), the fourth expandable member 144 (when expanded), the interior wall forming the cavity of the patient 104, and the second main body 150) may be operable to provide, or contribute in providing, the expanding of one or more of the expandable members 142, 144. For example, as the gas in the region between the third expandable member 142 (when expanded), the fourth expandable member 144 (when expanded), the interior wall forming the cavity of the patient 104, and the second main body 150 is being suctioned or removed, the said suctioned or removed gas may be provided into one or more of the expandable members 142, 144. In such an example, a filter, or the like, may be provided to remove unwanted particles, fluid, and/or gas from entering and/or exiting the expandable members 142, 144.

It is to be understood in the present disclosure that, in example embodiments wherein the second anchor assembly 140 comprises more than two expandable members, the second suction openings 146 may be provided between some or all of the expandable members. For example, if the second anchor assembly 140 comprises three expandable members, then second suction openings 146 may be provided between each of the three expandable members.

Each expandable member 142, 144, and cross-section thereof, may be formed in any one of a plurality of shapes, sizes, and/or dimensions. For example, the expandable members 142, 144 may resemble a tablet or donut shape with a circular cross-section. A cross sectional shape of the expandable members 142, 144 may also be one or more of a rectangle, square, pentagon, hexagon, etc., or combination of one or more geometric shapes, without departing from the teachings of the present disclosure.

In an example embodiment wherein the cross-sectional shape of the expandable members 142, 144 is circular, an outer diameter of the expandable members 142, 144 may be between about 5 to 100 mm. The distance that the expandable members 142, 144 may be expanded radially away from and contracted towards the second main body 150 may be between about 0.05 to 50 mm. It is to be understood in the present disclosure that the above dimensions are merely an illustration of example embodiments, and as such the dimensions may be smaller or larger than those recited above without departing from the teachings of the present disclosure.

The expandable members 142, 144 may be formed using any one or more of a plurality of materials, such as surgical-grade plastics, rubbers, etc. It is to be understood in the present disclosure that the material forming the surface pattern, roughness, and/or protrusion of the surface of the expandable members 142, 144 may be the same as, or different from, the material of the rest of the expandable member 142, 144. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

Method of Configuring the Endoscopic Device (e.g., Method 500)

Figure 5:
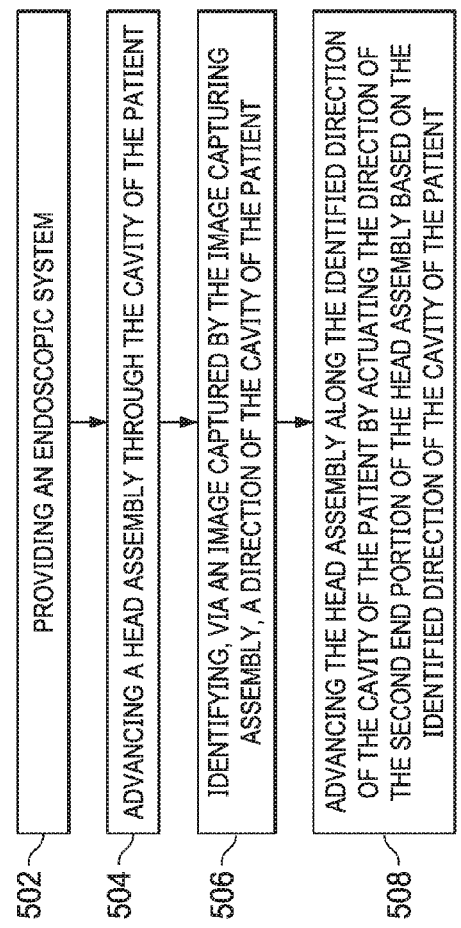
FIG. 5 is an illustration of an example embodiment of a method for performing a diagnostic and/or therapeutic/surgical action and/or procedure in a cavity of a patient.

Example embodiments of the endoscopic device 100 may be configurable to perform diagnostic and/or therapeutic/surgical actions and/or procedures in one of a plurality of ways. In an example embodiment, as illustrated in FIG. 5, a method 500 of performing and/or configuring a endoscopic system 100 to perform a diagnostic and/or therapeutic/surgical action and/or procedure in a cavity of a patient may comprise one or more of the actions described below.

In an example embodiment, the method 500 may comprise providing an endoscopic system (e.g., action 502). The endoscopic device provided may include one or more elements of the endoscopic device 100 described above and in the present disclosure. In an example embodiment, the provided endoscopic device may comprise a first main body. The first main body may be an elongated body having a first end. The provided endoscopic device may further comprise a second main body. The second main body may have a first end and a main cavity. The main cavity may house at least a portion of the first main body. The first main body and second main body may be slidable with respect to each other. The provided endoscopic device may further comprise an anchor assembly attached to the first main body near the first end of the first main body. The anchor assembly may comprise a first expandable member. The first expandable member may be configurable to expand radially away from the first main body. The anchor assembly may further comprise a second expandable member provided between the first expandable member and the first end of the first main body. The second expandable member may be configurable to expand radially away from the first main body. The provided endoscopic device may further comprise a second anchor assembly attached to the second main body near the first end of the second main body. The second anchor assembly may comprise a third expandable member. The third expandable member may be configurable to expand radially away from the second main body. The second anchor assembly may further comprise a fourth expandable member provided between the third expandable member and the first end of the second main body. The fourth expandable member may be configurable to expand radially away from the second main body. The provided endoscopic device may further comprise a head assembly. The head assembly may comprise a first end portion and a second end portion opposite to the first end portion. The first end portion may be attachable to the first end of the first main body. The second end portion may be selectively configurable to actuate in a plurality of directions with respect to the first end portion. The head assembly may further comprise an image capturing assembly provided in the second end portion. The image capturing assembly may be configurable to capture an image. The head assembly may further comprise an instrument section provided in the second end portion. The instrument section may be configurable to provide an instrument. The instrument may comprise at least two degrees of freedom of movement for performing an in vivo procedure in the cavity of the patient.

The method 500 may further comprise advancing a head assembly of the endoscopic system through the cavity of the patient (e.g., action 504). In this regard, the first end portion of the head assembly may be fixedly attached to the first end of the first main body. Furthermore, at least a portion of the first main body may be housed in the main cavity of the second main body.

The method 500 may further comprise identifying, via an image captured by an image capturing assembly of the endoscopic system, a direction of the cavity of the patient (e.g., action 506). For example, as illustrated in FIG. 3D, the image captured by the image capturing assembly may identify that an upcoming section or region of the cavity of the patient includes a bend.

The method 500 may further comprise advancing the head assembly along the identified direction of the cavity of the patient (e.g., action 508). For example, the head assembly may continue to move forward in a straight or relatively straight region of the cavity of the patient.

The method 500 may further comprise, when a bend section (such as a flexural and/or looping/bending section of a colon) in the cavity of the patient is identified, actuating, at the bend section in the cavity of the patient, the direction of a second end portion of the head assembly based on the identified direction of the bend section in the cavity of the patient (e.g., action 508). For example, as illustrated in FIG. 3D, when a bend in the cavity of the patient is identified (e.g., action 506), the second end portion (i.e., tip) of the head assembly may be actuated to move forward (and/or extend outwardly) and also bend based on the identified direction of the bend section in the cavity of the patient.

The method 500 may further comprise, when a bend section in the cavity, such as a colonic lumen, of the patient is identified, advancing the head assembly through the bend section.

The method 500 may further comprise, when a bend section in the cavity of the patient is identified, actuating, after advancing through the bend section, the direction of the second end portion of the head assembly based on a direction of the cavity of the patient identified after the bend section. For example, as illustrated in FIG. 3E, after passing through the bend section of the cavity of the patient, the second end portion of the head assembly may be straightened (or adjusted) based on the direction of the cavity after the bend section (which can be identified based on another image captured by the image capturing assembly).

The method 500 may further comprise, prior to the actuating, at the bend section, of the direction of the second end portion of the head assembly, securing the second main body to an interior wall forming the cavity of the patient by expanding the third expandable member to contact the interior wall forming the cavity of the patient, and expanding the fourth expandable member to contact the interior wall forming the cavity of the patient. For example, as illustrated in FIG. 3D, the second main body may be secured to the interior wall forming the cavity of the patient by expanding the second anchor assembly to secure or anchor to the interior wall forming the cavity of the patient. The securing of the second main body may also be provided using the second suction opening (i.e., applying a negative pressure) and/or the surface pattern, roughness, and/or protrusion (if provided) of the surface of the third and fourth expansion members of the second anchor assembly.

The method 500 may further comprise securing the first main body to an interior wall forming the cavity of the patient by expanding the first expandable member to contact the interior wall forming the cavity of the patient and expanding the second expandable member to contact the interior wall forming the cavity of the patient. For example, as illustrated in FIG. 3D, the main body may be secured to the interior wall forming the cavity of the patient by expanding the anchor assembly to secure or anchor to the interior wall forming the cavity of the patient. The securing of the main body may also be provided using the suction opening (i.e., applying a negative pressure) and/or the surface pattern, roughness, and/or protrusion (if provided) of the surface of the first and second expansion members of the anchor assembly. After the head assembly is advanced through the bend section, the first main body may be unsecured or unanchored from the interior wall forming the cavity of the patient. This may be achieved by un-expanding (or contracting) the first and second expandable members of the first anchor assembly, and may also include not applying a negative pressure by the suction opening. Thereafter, the first main body may also be advanced through the bend section by actuating the direction of the first main body based on the direction of the bend in the cavity of the patient.

The method 500 may further comprise advancing the second main body through the bend section towards the head assembly. Before doing so, as illustrated in FIG. 3F, the main body may be secured to the interior wall (after the bend) forming the cavity of the patient by expanding the anchor assembly to secure or anchor to the interior wall forming the cavity of the patient. The securing of the main body may also be provided using the suction opening (i.e., applying a negative pressure) and/or the surface pattern, roughness, and/or protrusion (if provided) of the surface of the first and second expansion members of the anchor assembly. Thereafter, the second main body may be unsecured or unanchored from the interior wall forming the cavity of the patient. This may be achieved by un-expanding (or contracting) the third and fourth expandable members of the second anchor assembly, and may also include not applying a negative pressure by the second suction opening. Once completed, the second main body may also be advanced through the bend section by actuating the direction of the second main body based on the direction of the bend in the cavity of the patient, as illustrated in FIG. 3F.

In example embodiments, the identified bend section in the cavity of the patient may be straightened (or made less looping/bending) by actuating the direction of the second main body, as illustrated in FIG. 3G. It is recognized in the present disclosure that such straightening of a bend section in the cavity of the patient may enable easier, quicker, and/or more efficient advancing of the endoscopic system into the remaining sections of the cavity of the patient. Furthermore, it is recognized in the present disclosure that such straightening of the bend section in the cavity, such as the colonic lumen, of the patient also enables easier, quicker, and/or more efficient removal, extraction, and/or retracting of the endoscopic system from the cavity of the patient after completing the diagnostic and/or therapeutic/surgical procedure.

The method 500 may further comprise identifying, via the image captured by the image capturing assembly, a location in the cavity of the patient for the instrument to perform the procedure.

The method 500 may further comprise securing the first main body to an interior wall forming the cavity of the patient by expanding the first expandable member to contact the interior wall forming the cavity of the patient and expanding the second expandable member to contact the interior wall forming the cavity of the patient, as illustrated in FIG. 2C. In this regard, the third expandable member and/or the fourth expandable member may also be expanded to contact the interior wall forming the cavity of the patient.

The method 500 may further comprise actuating the instrument to perform the procedure based on the image captured by the image capturing assembly, as illustrated in FIG. 2C.

It is to be understood in the present disclosure that one or more of the aforementioned actions of method 500 may be performed manually, either in whole or in part, by an operator/surgeon and/or assisted, either in whole or in part, by the controller 160 and/or one or more motors (not shown) in example embodiments.

The Endoscopic System (e.g., Endoscopic System 600)

FIGS. 6 to 8 illustrate another example embodiment of an endoscopic system 600. The endoscopic system 600 may include an outer assembly 610. The endoscopic system 600 may also include a main assembly 620. The outer assembly 610 may house at least a portion of the main assembly 620. For example, the outer assembly 610 may not house some or all of the navigation section 622. The endoscopic system 600 may also include a controller (not shown) and/or surgeon/operator console for controlling and/or managing one or more elements of the endoscopic system 600. These and other elements of the endoscopic system 600 will now be described with reference to FIGS. 6 to 8.

Outer Assembly (e.g., Outer Assembly 610)

As illustrated in at least FIG. 6B, FIG. 6G, FIG. 6H, FIG. 6I, FIG. 6J, FIG. 6K, FIG. 6L, FIG. 6N, FIG. 6O, FIG. 6P, FIG. 6Q, FIG. 6R, and FIG. 6S, the endoscopic system 600 may include an outer assembly 610. The outer assembly 610 may include an elongated body 610', a proximal end 610a, and a distal end 610b, as illustrated in at least the side view of FIG. 6B. A length of the outer assembly 610 may be between about 750 to 2500 mm, and a diameter of the elongated body 610' of the outer assembly 610 may be between about 7 to 25 mm in example embodiments. Other dimensions are also contemplated without departing from the teachings of the present disclosure.

The outer assembly 610 may include a plurality of cavities or channels (hereinafter "cavities"), which may include one or more pressure cavities 618a, one or more pressure cavities 618b, one or more pressure cavities 618c, and/or a main cavity 618d. The outer assembly 610 may also include other cavities (not shown), such as cavities for data cables, power cables, insertion/removal of instruments, etc. The outer assembly 610 may also include one or more outer anchor assemblies 612. Each outer anchor assembly 612 may include one or more expandable members 616, one or more pressure openings 613a, and/or one or more pressure openings 613b. Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618b). In example embodiments where the outer assembly 610 does not include any expandable members 616, the outer assembly 610 may also not include corresponding pressure cavity or cavities (e.g., pressure cavity 618b). These elements of the outer assembly 610 will now be described below.

Cavities of the Outer Assembly 610 (e.g., Main Cavity 618d, Pressure Cavity 618a, Pressure Cavity 618b, Pressure Cavity 618c)

In an example embodiment, the outer assembly 610 may include a plurality of cavities, including a main cavity 618d, one or more pressure cavities 618a, one or more pressure cavities 618b, and/or one or more pressure cavities 618c. Each of the cavities of the outer assembly 610 may resemble a channel, tube, or the like.

(i) Main Cavity 618d

As illustrated in at least the cross-sectional view of FIGS. 6G-H, the outer assembly 610 may include a main cavity 618d provided through the outer assembly 610 between the proximal end 610a and distal end 610b of the outer assembly 610. The main cavity 618d may be for use in housing at least a portion of the main assembly 620 (as further described below and in the present disclosure). When the main cavity 618d houses the main assembly 620, the outer assembly 610 and main assembly 620 may (or may not) be slidable relative to one another. For example, when the endoscopic system 600 includes an extendible section 625 (as further described below and in the present disclosure), the outer assembly 610 and main assembly 620 may not be slidable relative to one another since movement of a distal end 620b of the main assembly 620 relative to the outer assembly 610 may be achievable via the extendible section 625. As another example, when the endoscopic system 600 does not include an extendible section 625, the outer assembly 610 and main assembly 620 may be slidable relative to one another. It is to be understood that an endoscopic system 600 having an extendible section 625 may also include the outer assembly 610 and main assembly 620 slidable relative to one another without departing from the teachings of the present disclosure.

(ii) Pressure Cavity 618a

As illustrated in at least the cross-sectional view of FIG. 6G (which is a cross-sectional view of the outer assembly 610, as depicted in FIG. 6B), the outer assembly 610 may also include one or more pressure cavities 618a provided through the outer assembly 610 between the proximal end 610a and distal end 610b of the outer assembly 610. One or more of the pressure cavities 618a may be connected at its proximal end to one or more pressure sources 642a and connected at its distal end to one or more pressure openings 613a.

In an example embodiment, a pressure applied in each of the one or more pressure cavities 618a may be selectively controllable by a surgeon, operator, and/or controller (not shown) via the one or more pressure sources 642a, and such applied pressure may be selectively switched between an applied negative pressure, an applied positive pressure, or no applied pressure.

In another example embodiment, the pressure cavities 618a may include at least a first set and/or a second set of cavities. The first set of one or more pressure cavities 618a may be connected to a positive pressure source 642a, in which case such first set of pressure cavities 618a may be selectively controllable by a surgeon, operator, and/or controller (not shown) via the one or more positive pressure sources 642a to have an applied positive pressure or no applied pressure. Alternatively or in addition, the second set of one or more pressure cavities 618a may be connected to a negative pressure source 642a, in which case such second set of pressure cavities 618a may be selectively controllable by a surgeon, operator, and/or controller (not shown) via the one or more negative pressure sources 642a to have an applied negative pressure or no applied pressure. Although FIG. 6G illustrates a single pressure cavity 618a, it is to be understood that more than one pressure cavity 618a may be provided in the outer assembly 610 without departing from the teachings of the present disclosure.

(iii) Pressure Cavity 618b

As illustrated in at least the cross-sectional view of FIG. 6G (which is a cross-sectional view of the outer assembly 610, as depicted in FIG. 6B), the outer assembly 610 may also include one or more pressure cavities 618b provided through the outer assembly 610. One or more of the pressure cavities 618b may be connected at its proximal end to one or more pressure sources 642b and connected at its distal end to one or more expandable members 616. Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618b). In example embodiments where the outer assembly 610 does not include any expandable members 616, the outer assembly 610 may also not include corresponding pressure cavity or cavities (e.g., pressure cavity 618b).

In an example embodiment, a pressure applied in each of the one or more pressure cavities 618b may be selectively controllable by a surgeon, operator, and/or controller (not shown) via the one or more pressure sources 642b, and such applied pressure may be selectively switched between an applied negative pressure, an applied positive pressure, or no applied pressure.

In another example embodiment, the pressure cavities 618b may include at least a first set and/or a second set of cavities. The first set of one or more pressure cavities 618b may be connected to a positive pressure source 642b, in which case such first set of pressure cavities 618b may be selectively controllable by a surgeon, operator, and/or controller (not shown) via the one or more positive pressure sources 642b to have an applied positive pressure or no applied pressure. Alternatively or in addition, the second set of one or more pressure cavities 618b may be connected to a negative pressure source 642b, in which case such second set of pressure cavities 618b may be selectively controllable by a surgeon, operator, and/or controller (not shown) via the one or more negative pressure sources 642b to have an applied negative pressure or no applied pressure. Although FIGS. 6G-H illustrate a single pressure cavity 618b, it is to be understood that more than one pressure cavity 618b may be provided in the outer assembly 610 without departing from the teachings of the present disclosure.

(iv) Pressure Cavity 618c

As illustrated in at least the cross-sectional view of FIG. 6G and FIG. 6H (which is a cross-sectional view of the outer assembly 610, as depicted in FIG. 6B), the outer assembly 610 may also include one or more pressure cavities 618c provided through the outer assembly 610 in a similar manner as cavities 618a and 618b. The one or more pressure cavities 618c may be connected at its proximal end to one or more pressure sources 642c and connected at its distal end to one or more pressure openings 613b. A pressure applied in each of the one or more pressure cavities 618c may be selectively controllable by a surgeon, operator, and/or controller (not shown) via the one or more pressure sources 642c, and such applied pressure may be selectively switched between an applied negative pressure, an applied positive pressure, or no applied pressure.

In another example embodiment, the pressure cavities 618c may include at least a first set and a second set of cavities. The first set of one or more pressure cavities 618c may be connected to a positive pressure source 642c, in which case such first set of pressure cavities 618c may be selectively controllable by a surgeon, operator, and/or controller (not shown) via the one or more positive pressure sources 642c to have an applied positive pressure or no applied pressure. Alternatively or in addition, the second set of one or more pressure cavities 618c may be connected to a negative pressure source 642c, in which case such second set of pressure cavities 618c may be selectively controllable by a surgeon, operator, and/or controller (not shown) via the one or more negative pressure sources 642c to have an applied negative pressure or no applied pressure. Although FIGS. 6G-H illustrate a single pressure cavity 618c, it is to be understood that more than one pressure cavity 618c may be provided in the outer assembly 610 without departing from the teachings of the present disclosure.

Outer Anchor Assembly (e.g., Outer Anchor Assembly 612)

As illustrated in at least the side views of FIGS. 6B, 6I-L, and 6N-O, an example embodiment of an outer anchor assembly 612 may be provided at the distal end 610b of the outer assembly 610. The outer anchor assembly 612 may include one or more expandable members 616, one or more pressure openings 613a, and/or one or more pressure openings 613b. In an example embodiment, the pressure opening(s) 613a may be selectively configurable to apply a negative pressure and/or positive pressure independently from the pressure opening(s) 613b (if provided) and/or any other pressure openings (if provided) of the outer assembly 610 and/or main assembly 620. Similarly, the pressure opening(s) 613b (if provided) may be selectively configurable to apply a negative pressure and/or positive pressure independently from the pressure opening(s) 613a and/or any other pressure openings (if provided) of the outer assembly 610 and/or main assembly 620.

When inserted into a cavity of a patient, the outer anchor assembly 612 may be configurable to secure or anchor the outer anchor assembly 612 with respect to an interior wall forming the cavity of the patient. Alternatively or in addition, when inserted into a cavity of a patient, the outer anchor assembly 612 may be configurable to increase a volume of the cavity of the patient so as to, among other things, assist or enable the surgeon, operator, and/or controller to move the endoscopic system 600 within the cavity of the patient and/or perform a surgical action. These elements of the outer anchor assembly 612 will now be described below.

(i) Expandable Member 616 (e.g., Expandable Member 616)

As illustrated in at least FIGS. 6B, 6I-L, and 6N-O, an example embodiment of the outer anchor assembly 612 may include one or more expandable members 616. The expandable member 616 may be securable or secured to an exterior of the elongated body 610'. The expandable member 616 may include one or more openings for allowing passage of gas and/or liquid, and/or allowing a manipulation of pressure within the expandable member 616. Each such opening may be connected to one or more of the pressure cavities (e.g., pressure cavity 618b). Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618b). In example embodiments where the outer assembly 610 does not include any expandable members 616, the outer assembly 610 may also not include corresponding pressure cavity or cavities (e.g., pressure cavity 618b).

In an example embodiment, one or more portions of the exterior surface of the expandable member 616 may include protrusions and/or texture so as to improve securing to the interior wall forming the cavity of the patient. Furthermore, a quantity of between about 1 to 3 expandable members 616 may be provided for the outer anchor assembly 612. Other quantities are also contemplated without departing from the teachings of the present disclosure. The expandable member 616 may be provided at a most distal position of the outer assembly 610, before pressure openings 613b, between pressure openings 613a and 613b, and/or before pressure openings 613a.

In an expanded state (or securing or anchoring state), which may be a state in which the one or more pressure sources 642b provide a positive pressure to the expandable member 616 via the one or more pressure cavities 618b, the expandable member 616 may be configurable to expand radially outward from the elongated body 610' (e.g., resembling a balloon, tire, or the like). An overall diameter of the expandable member 616, when in the expanded state, may be between about 7 to 25 mm. Other dimensions are also contemplated without departing from the teachings of the present disclosure. During diagnostic and/or therapeutic/surgical procedures when a securing or anchoring of the outer assembly 610 with respect to an interior wall forming a cavity of a patient (e.g., interior wall of a colon) is desired or required, the expandable member 616 may be expanded to its expanded state. It is recognized in the present disclosure that the securing or anchoring of the outer assembly 610 with respect to the interior wall forming the cavity of the patient may be performed solely by the expandable member 616 (configured in the expanded state), solely by the pressure opening(s) 613a (via applying a negative pressure or suction), or solely by the pressure opening(s) 613b (via applying a negative pressure or suction). Alternatively, the securing or anchoring of the outer assembly 610 may be performed cooperatively by the expandable member 616 (configured in the expanded state), pressure opening(s) 613a (via applying a negative pressure or suction), and/or pressure opening(s) 613b (via applying a negative pressure or suction), as further described below and in the present disclosure.

In a normal or non-expanded state, which may be a state in which the one or more pressure sources 642b do not provide a positive pressure to the expandable member 616 via the one or more pressure cavities 618b (or the pressure source 642b provides a negative pressure to the expandable member 616 via the one or more pressure cavities 618b), the expandable member 616 may not (or may minimally) protrude outward from the elongated body 610'. During diagnostic and/or therapeutic/surgical procedures when an unsecuring or unanchoring of the outer assembly 610 with respect to an interior wall forming a cavity of a patient is desired or required (e.g., when the expandable member 616 is in the expanded state), the expandable member 616 may be un-expanded (or deflated, shrunken, or collapsed) to its normal or non-expanded state. It is recognized in the present disclosure that the unsecuring or unanchoring of the outer assembly 610 with respect to the interior wall forming the cavity of the patient may be performed solely by the expandable member 616 (configured in the non-expanded state), solely by the pressure opening(s) 613*a* (via applying a positive pressure), or solely by the pressure opening(s) 613*b* (via applying a positive pressure). Alternatively, the unsecuring or unanchoring of the outer assembly 610 may be performed cooperatively by the expandable member 616 (configured in the non-expanded state), pressure opening(s) 613*a* (via applying a positive pressure), and/or pressure opening(s) 613*b* (via applying a positive pressure), as further described below and in the present disclosure.

(ii) Pressure Opening (e.g., Pressure Opening 613*a*)

As illustrated in at least FIGS. 6B, 6I-L, and 6N-O, an example embodiment of the outer anchor assembly 612 may include one or more pressure openings 613*a*. The one or more pressure openings 613*a* may be provided adjacent to the expandable member 616. The one or more pressure openings 613*a* may be an opening in the elongated body 610' connected to the one or more pressure cavities 618*a*. In an example embodiment, each of the one or more pressure openings 613*a* may be formed in one or more of a plurality of shapes, such as a circle, oval, triangle, square, rectangle, slit, etc. Furthermore, each of the one or more pressure openings 613*a* may have a diameter of between about 200 to 2000 microns. Furthermore, a quantity of between about 1 to 10 pressure openings 613*a* may be provided. Other dimensions, shapes, and/or quantities are also contemplated without departing from the teachings of the present disclosure. Although the figures illustrate a single row of pressure openings 613*a* aligned perpendicular to axis X, it is to be understood that more than one row of pressure openings 613*a* (which may be aligned perpendicular to axis X and/or at other angles relative to axis X) and/or one or more rows or pressure openings 613*a* aligned parallel to axis X may be provided in the outer anchor assembly 612 without departing from the teachings of the present disclosure.

In a normal state, which may be a state in which the pressure source 642*a* does not provide any negative or positive pressure to the pressure cavity 618*a*, the one or more pressure openings 613*a* may not provide any negative or positive pressure to an exterior of the one or more pressure openings 613*a*.

In a securing/anchoring state, which may be a state in which the one or more pressure sources 642*a* provide a negative pressure to the one or more pressure cavities 618*a*, the one or more pressure openings 613*a* may provide a negative pressure (e.g., suction force inwards) to an exterior of the outer assembly 610 (e.g., an area outside of the one or more pressure openings 613*a*). During diagnostic and/or therapeutic/surgical procedures when a securing or anchoring of the outer assembly 610 with respect to an interior wall forming a cavity of a patient is desired or required, the one or more pressure openings 613*a* may provide a negative pressure (e.g., suction force inwards) so as to secure/anchor or further improve the securing or anchoring of the outer assembly 610 (e.g., in addition to the securing/anchoring provided by the expandable member 616 in its expanded state and/or pressure opening(s) 613*b*). For example, when a sufficient negative pressure is applied by the one or more pressure openings 613*a*, such applied negative pressure may be operable to bring inwards or collapse a surrounding portion of the interior wall forming the cavity of the patient nearby the one or more pressure openings 613*a* towards the outer assembly 610 (e.g., see example illustrated in FIG. 8D). It is recognized in the present disclosure that the securing or anchoring of the outer assembly 610 with respect to the interior wall forming the cavity of the patient may be performed solely by the one or more pressure openings 613*a* (via applying a negative pressure or suction), solely by the expandable member 616 (configured in the expanded state), or solely by the pressure opening(s) 613*b* (via applying a negative pressure or suction). Alternatively, the securing or anchoring of the outer assembly 610 may be performed cooperatively by the one or more pressure openings 613*a* (via applying a negative pressure or suction), the expandable member 616 (configured in the expanded state), and/or pressure opening(s) 613*b* (via applying a negative pressure or suction), as described in the present disclosure. It is recognized in the present disclosure that the expanding and contacting of the expandable member 616 with the interior wall forming the cavity of the patient and the negative pressure applied by the one or more pressure openings 613*a* may provide for improved securing or anchoring of the outer assembly 610. Similarly, the simultaneous application of negative pressure by the one or more pressure openings 613*a* and the one or more pressure openings 613*b* may provide for improved securing or anchoring of the outer assembly 610.

In an un-securing/un-anchoring state, which may be a state in which the pressure source 642*a* provides a positive pressure to the pressure cavity 618*a*, the one or more pressure openings 613*a* may provide positive pressure to an exterior of the outer assembly 610 (e.g., an area outside of the one or more pressure openings 613*a*). During diagnostic and/or therapeutic/surgical procedures when a securing or anchoring of the outer assembly 610 with respect to an interior wall forming a cavity of a patient is no longer desired or required (e.g., a movement of the outer assembly 610 is desired or required) and/or if a surrounding portion of an interior wall forming a cavity of a patient nearby the one or more pressure openings 613*a* needs to be urged or pushed outwards or away from the endoscopic system 600, the one or more pressure openings 613*a* may provide a positive pressure so as to unsecure/unanchor or further improve the unsecuring or unanchoring of the outer assembly 610 (e.g., in addition to the unsecuring/unanchoring provided by the expandable member 616 in its non-expanded state and/or pressure opening(s) 613*b*). For example, when a sufficient positive pressure is applied by the one or more pressure openings 613*a*, such applied positive pressure may be operable to urge/push outwards, expand, or un-collapse a surrounding portion of the interior wall forming the cavity of the patient nearby the one or more pressure openings 613*a* away from the outer assembly 610 (e.g., see example illustrated in FIG. 8H). It is recognized in the present disclosure that the unsecuring or unanchoring of the outer assembly 610 with respect to the interior wall forming the cavity of the patient may be performed solely by the one or more pressure openings 613*a* (via applying a positive pressure), solely by the expandable member 616 (configured in the non-expanded state), or solely by the pressure opening(s) 613*b* (via applying a positive pressure). Alternatively, the unsecuring or unanchoring of the outer assembly 610 may be performed cooperatively by the one or more pressure openings 613*a* (via applying a positive pressure), the expandable member 616 (configured in the non-expanded state), and/or pressure opening(s) 613b (via applying a positive pressure), as described in the present disclosure. It is recognized in the present disclosure that the non-expanding of the expandable member 616 and the positive pressure applied by the one or more pressure openings 613a may provide for improved unsecuring or unanchoring of the outer assembly 610. Similarly, the simultaneous application of positive pressure by the one or more pressure openings 613a and the one or more pressure openings 613b may provide for improved unsecuring or unanchoring of the outer assembly 610.

In an example embodiment, the one or more pressure openings 613a may be oriented at an angle (not shown) relative to a central axis X of the outer assembly 610 so as to provide a more directional application of negative and/or positive pressure. For example, the one or more pressure openings 613a may be oriented in such a way that the applied negative and/or positive pressure is directed backwards (or away from a distal end of the main assembly 620).

(iii) Pressure Opening(s) 613b

As illustrated in at least FIGS. 6B, 6I-L, and 6N-O, an example embodiment of the outer anchor assembly 612 may include one or more pressure openings 613b. The one or more pressure openings 613b may be provided adjacent to the expandable member 616. For example, the expandable member 616 may be provided between the one or more pressure openings 613a and the one or more pressure openings 613b. The one or more pressure openings 613b may be an opening in the elongated body 610' connected to the one or more pressure cavities 618c. In an example embodiment, each of the one or more pressure openings 613b may be formed in one or more of a plurality of shapes, such as a circle, oval, triangle, square, rectangle, slit, etc. Furthermore, each of the one or more pressure openings 613b may have a diameter of between about 200 to 2000 microns. Furthermore, a quantity of between about 1 to 10 pressure openings 613b may be provided. Other dimensions, shapes, and/or quantities are also contemplated without departing from the teachings of the present disclosure. Although the figures illustrate a single row of pressure openings 613b aligned perpendicular to axis X, it is to be understood that more than one row of pressure openings 613b (which may be aligned perpendicular to axis X and/or at other angles relative to axis X) and/or one or more rows or pressure openings 613b aligned parallel to axis X may be provided in the outer anchor assembly 612 without departing from the teachings of the present disclosure.

In a normal state, which may be a state in which the pressure source 642c does not provide any negative or positive pressure to the pressure cavity 618c, the one or more pressure openings 613b may not provide any negative or positive pressure to an exterior of the one or more pressure openings 613b.

In a securing/anchoring state, which may be a state in which the one or more pressure sources 642c provide a negative pressure to the one or more pressure cavities 618c, the one or more pressure openings 613b may provide a negative pressure (e.g., suction force inwards) to an exterior of the outer assembly 610 (e.g., an area outside of the one or more pressure openings 613b). During diagnostic and/or therapeutic/surgical procedures when a securing or anchoring of the outer assembly 610 with respect to an interior wall forming a cavity of a patient is desired or required, the one or more pressure openings 613b may provide a negative pressure (e.g., suction force inwards) so as to secure/anchor or further improve the securing or anchoring of the outer assembly 610 (e.g., in addition to the securing/anchoring provided by the expandable member 616 in its expanded state and/or pressure opening(s) 613a). For example, when a sufficient negative pressure is applied by the one or more pressure openings 613b, such applied negative pressure may be operable to bring inwards or collapse a surrounding portion of the interior wall forming the cavity of the patient nearby the one or more pressure openings 613b towards the outer assembly 610 (e.g., see example illustrated in FIG. 8D). It is recognized in the present disclosure that the securing or anchoring of the outer assembly 610 with respect to the interior wall forming the cavity of the patient may be performed solely by the one or more pressure openings 613b (via applying a negative pressure or suction), solely by the expandable member 616 (configured in the expanded state), or solely by the pressure opening(s) 613a (via applying a negative pressure or suction). Alternatively, the securing or anchoring of the outer assembly 610 may be performed cooperatively by the one or more pressure openings 613b (via applying a negative pressure or suction), the expandable member 616 (configured in the expanded state), and/or pressure opening(s) 613a (via applying a negative pressure or suction), as described in the present disclosure. It is recognized in the present disclosure that the expanding and contacting of the expandable member 616 with the interior wall forming the cavity of the patient and the negative pressure applied by the one or more pressure openings 613b may provide for improved securing or anchoring of the outer assembly 610. Similarly, the simultaneous application of negative pressure by the one or more pressure openings 613b and the one or more pressure openings 613a may provide for improved securing or anchoring of the outer assembly 610.

In an un-securing/un-anchoring state, which may be a state in which the pressure source 642c provides a positive pressure to the pressure cavity 618c, the one or more pressure openings 613b may provide positive pressure to an exterior of the outer assembly 610 (e.g., an area outside of the one or more pressure openings 613b). During diagnostic and/or therapeutic/surgical procedures when a securing or anchoring of the outer assembly 610 with respect to an interior wall forming a cavity of a patient is no longer desired or required (e.g., a movement of the outer assembly 610 is desired or required) and/or if a surrounding portion of an interior wall forming a cavity of a patient nearby the one or more pressure openings 613b needs to be urged or pushed outwards away from the endoscopic system 600, the one or more pressure openings 613b may provide a positive pressure so as to unsecure/unanchor or further improve the unsecuring or unanchoring of the outer assembly 610 (e.g., in addition to the unsecuring/unanchoring provided by the expandable member 616 in its non-expanded state and/or pressure opening(s) 613a). For example, when a sufficient positive pressure is applied by the one or more pressure openings 613b, such applied positive pressure may be operable to urge/push outwards, expand, or un-collapse a surrounding portion of the interior wall forming the cavity of the patient nearby the one or more pressure openings 613b away from the outer assembly 610 (e.g., see example illustrated in FIG. 8H). It is recognized in the present disclosure that the unsecuring or unanchoring of the outer assembly 610 with respect to the interior wall forming the cavity of the patient may be performed solely by the one or more pressure openings 613b (via applying a positive pressure), solely by the expandable member 616 (configured in the non-expanded state), or solely by the pressure opening(s) 613a (via applying a positive pressure). Alternatively, the unsecuring or unanchoring of the outer assembly 610 may be performed cooperatively by the one or more pressure openings 613*b* (via applying a positive pressure), the expandable member 616 (configured in the non-expanded state), and/or pressure opening(s) 613*a* (via applying a positive pressure), as described in the present disclosure. It is recognized in the present disclosure that the non-expanding of the expandable member 616 and the positive pressure applied by the one or more pressure openings 613*b* may provide for improved unsecuring or unanchoring of the outer assembly 610. Similarly, the simultaneous application of positive pressure by the one or more pressure openings 613*b* and the one or more pressure openings 613*a* may provide for improved unsecuring or unanchoring of the outer assembly 610.

In an example embodiment, the one or more pressure openings 613*b* may be oriented at an angle (not shown) relative to a central axis X of the outer assembly 610 so as to provide a more directional application of negative and/or positive pressure. For example, the one or more pressure openings 613*b* may be oriented in such a way that the applied negative and/or positive pressure is directed backwards (or away from a distal end of the main assembly 620).

Figure 7C:
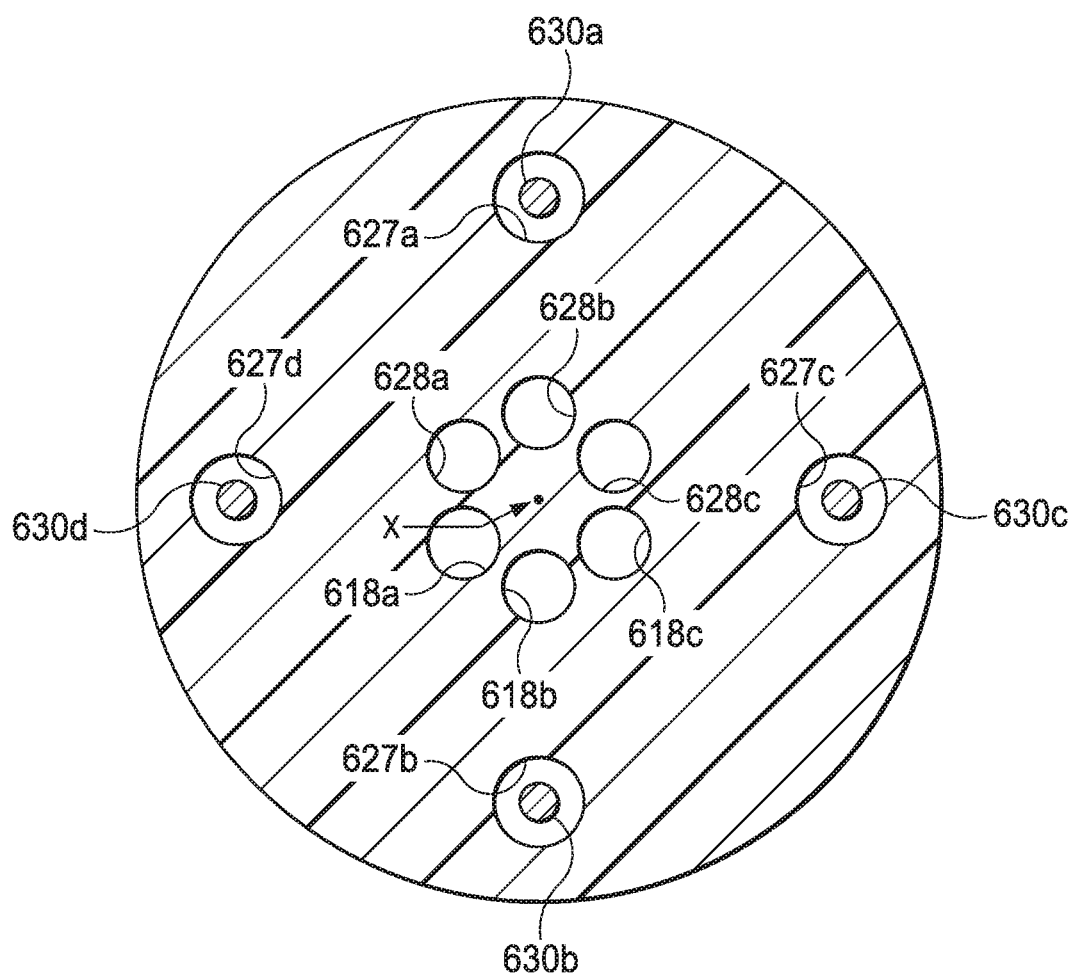
FIG. 7C is a cross-sectional view of an example embodiment of a main assembly of an endoscopic system.

Although example embodiments described above and in the present disclosure provide for pressure cavities 618*a*, 618*b*, and 618*c* to be included in the outer assembly 610, it is recognized (and described in the present disclosure and illustrated in at least FIGS. 7A-C) that the pressure cavity 618*a* (which connects to pressure source 642*a* at one end and connects to pressure opening 613*a* at another end) may be provided in the main assembly 620 instead of the outer assembly 610. Alternatively or in addition, as described in the present disclosure and illustrated in at least FIGS. 7A-C, the pressure cavity 618*b* (which connects to pressure source 642*b* at one end and connects to expandable member 616 at another end) may be provided in the main assembly 620 instead of the outer assembly 610. Alternatively or in addition, as described in the present disclosure and illustrated in at least FIGS. 7A-C, the pressure cavity 618*c* (which connects to pressure source 642*c* at one end and connects to pressure opening 613*b* at another end) may be provided in the main assembly 620 instead of the outer assembly 610.

The Main Assembly (e.g., Main Assembly 620)

As illustrated in at least FIG. 6A, FIG. 6C, FIG. 6D, FIG. 6E, FIG. 6F, FIGS. 6G-L, and FIGS. 6N-O, the endoscopic system 600 may include a main assembly 620. The main assembly 620 may include an elongated body 620', a proximal end 620*a*, and a distal end 620*b*, as illustrated in at least the side view of FIG. 6A. A length of the main assembly 620 may be between about 45 to 100 mm, and a diameter of the main assembly 620 may be between about 7 to 25 mm in example embodiments. Other dimensions are also contemplated without departing from the teachings of the present disclosure.

The main assembly 620 may include a plurality of cavities or channels (hereinafter "cavities"), which may include one or more pressure cavities 628*a*, one or more pressure cavities 628*b*, and/or one or more pressure cavities 628*c*. The main assembly 620 may also include a plurality of tendon members 630. The main assembly 620 may also include one or more navigation sections 622, which may include one or more instruments 621, one or more bendable sections 624, one or more extendible sections 625, and a main anchor assembly. The main anchor assembly may include one or more expandable members 626, one or more pressure openings 623*a*, and/or one or more pressure openings 623*b*.

Although the figures may illustrate example embodiments of the main assembly 620 having an expandable member 626, it is to be understood that example embodiments of the main assembly 620 may include more than one expandable member 626 or not include any expandable members 626. In example embodiments where the main assembly 620 includes more than one expandable member 626, the main assembly 620 may also include more than one corresponding pressure cavities (e.g., pressure cavity 628*b*). In example embodiments where the main assembly 620 does not include any expandable members 626, the main assembly 620 may also not include corresponding pressure cavity or cavities (e.g., pressure cavity 628*b*). These elements of the outer assembly 610 will now be described below.

Cavities of the Main Assembly 620 (e.g., Pressure Cavity 628*a*, Pressure Cavity 628*b*, Pressure Cavity 628*c*, Movement Cavity 627*a*, Movement Cavity 627*b*, Movement Cavity 627*c*, Movement Cavity 627*d*)

In an example embodiment, the main assembly 620 may include a plurality of pressure cavities (e.g., pressure cavity 628*a*, pressure cavity 628*b*, pressure cavity 628*c*) and a plurality of movement cavities (e.g., movement cavity 627*a*, movement cavity 627*b*, movement cavity 627*c*, movement cavity 627*d*).

(i) Pressure Cavities (e.g., Pressure Cavities 628*a*, 628*b*, 628*c*)

Figure 6C:
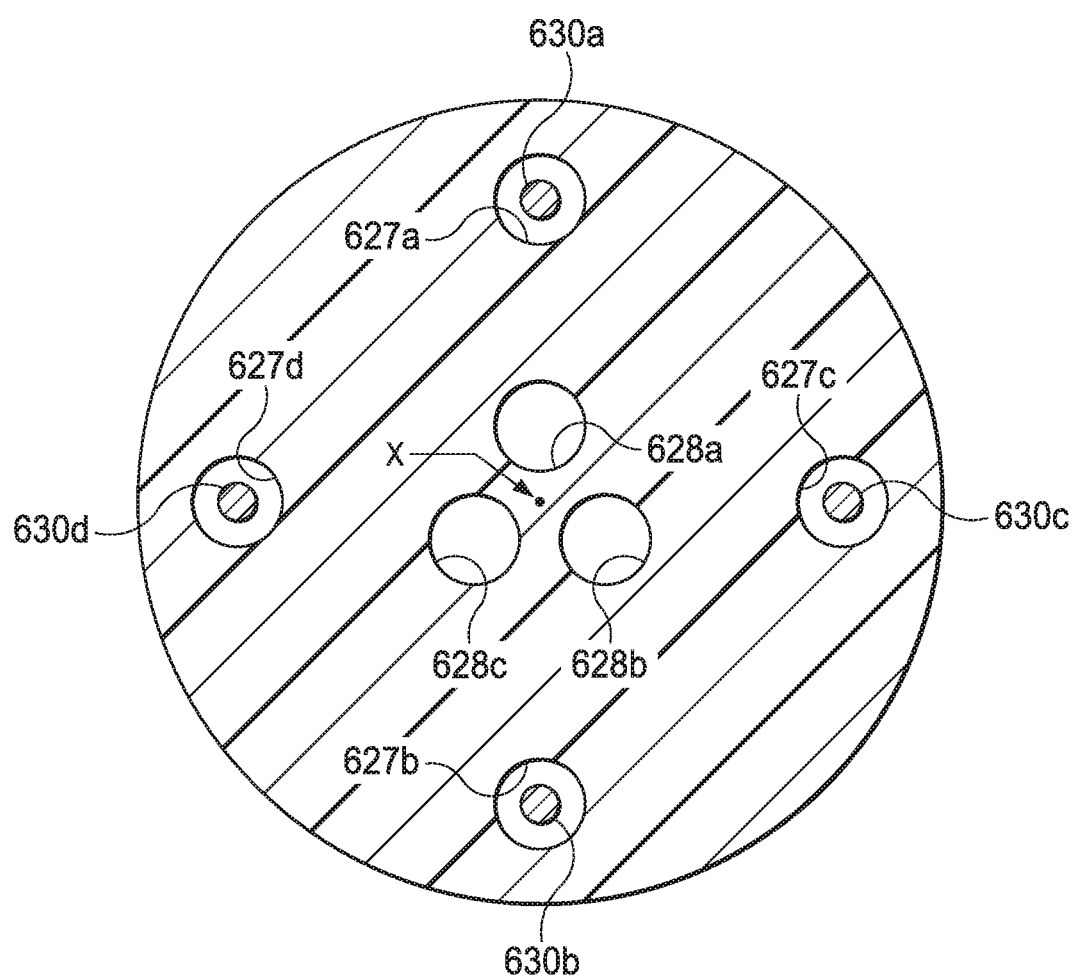
FIG. 6C is a cross-sectional view of an example embodiment of a main assembly of an endoscopic system.

The main assembly 620 may include a plurality of cavities or channels (hereinafter "cavities"). For example, as illustrated in at least FIG. 6C (which is a cross-sectional view of the main assembly 620, as depicted in FIG. 6A), FIG. 6D (which is a cross-sectional view of the main assembly 620, as depicted in FIG. 6A), FIG. 6E (which is a cross-sectional view of the main assembly 620, as depicted in FIG. 6A), and FIG. 6F (which is a cross-sectional view of the main assembly 620, as depicted in FIG. 6A), the main assembly 620 may include one or more pressure cavities 628*a*, one or more pressure cavities 628*b*, and/or one or more pressure cavities 628*c*.

Pressure Cavity 628*a*

As illustrated in at least the cross-sectional views of FIGS. 6C-F, the main assembly 620 may also include one or more pressure cavities 628*a* provided through the main assembly 620 between the proximal end 620*a* and distal end 620*b* of the main assembly 620. One or more of the pressure cavities 628*a* may be connected at its proximal end to one or more pressure sources 640*a* and connected at its distal end to one or more pressure openings 623*a*.

In an example embodiment, a pressure applied in each of the one or more pressure cavities 628*a* may be selectively controllable by a surgeon, operator, and/or controller (not shown) via the one or more pressure sources 640*a*, and such applied pressure may be selectively switched between an applied negative pressure, an applied positive pressure, or no applied pressure.

In another example embodiment, the pressure cavities 628*a* may include at least a first set and/or a second set of cavities. The first set of one or more pressure cavities 628*a* may be connected to a positive pressure source 640*a*, in which case such first set of pressure cavities 628*a* may be selectively controllable by a surgeon, operator, and/or controller (not shown) via the one or more positive pressure sources 640*a* to have an applied positive pressure or no applied pressure. Alternatively or in addition, the second set of one or more pressure cavities 628*a* may be connected to a negative pressure source 640*a*, in which case such second set of pressure cavities 628*a* may be selectively controllable by a surgeon, operator, and/or controller (not shown) via the one or more negative pressure sources 640*a* to have an applied negative pressure or no applied pressure. Although FIGS. 6C-F illustrate a single pressure cavity 628*a*, it is to be understood that more than one pressure cavity 628*a* may be provided in the main assembly 620 without departing from the teachings of the present disclosure.

Pressure Cavity 628*b*

Figure 6D:
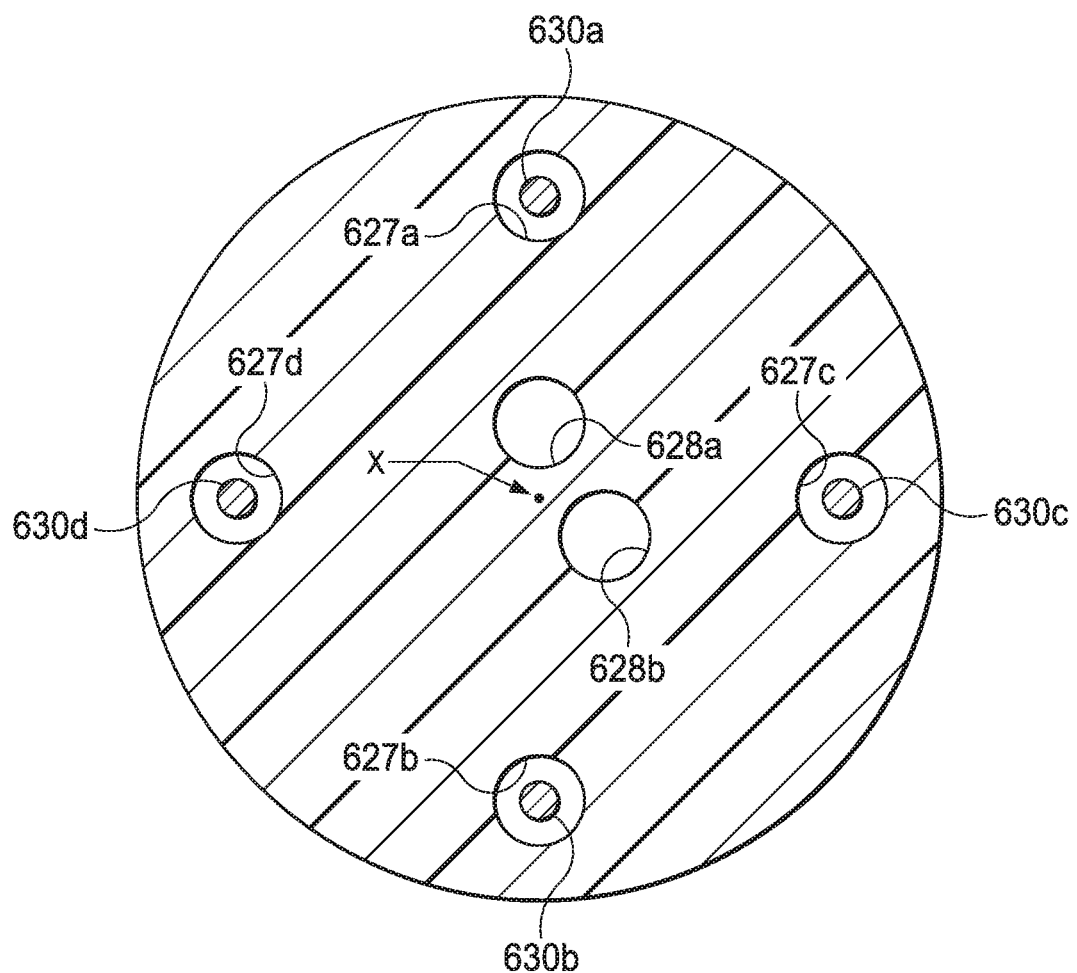
FIG. 6D is a cross-sectional view of an example embodiment of a main assembly of an endoscopic system.
Figure 6E:
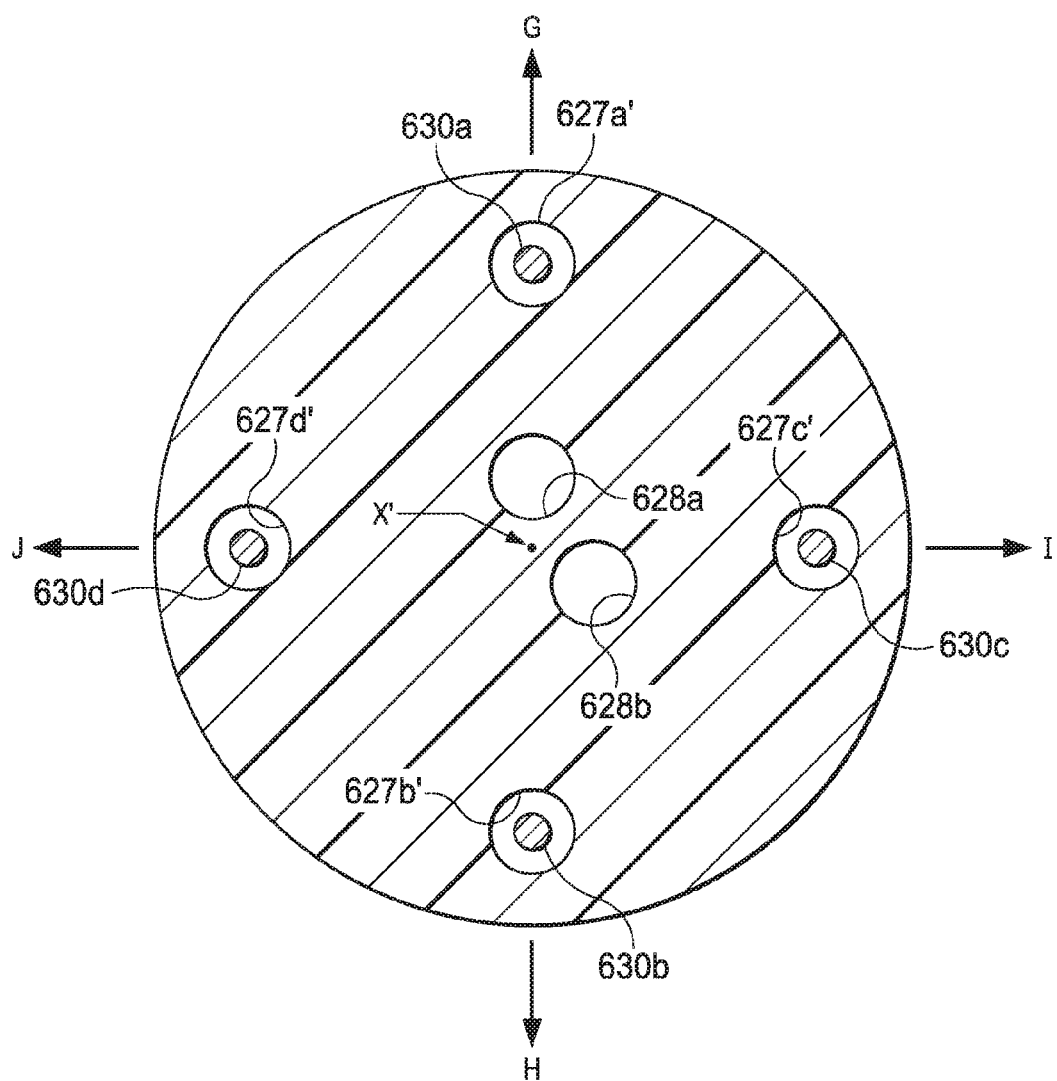
FIG. 6E is a cross-sectional view of an example embodiment of a main assembly of an endoscopic system.
Figure 6F:
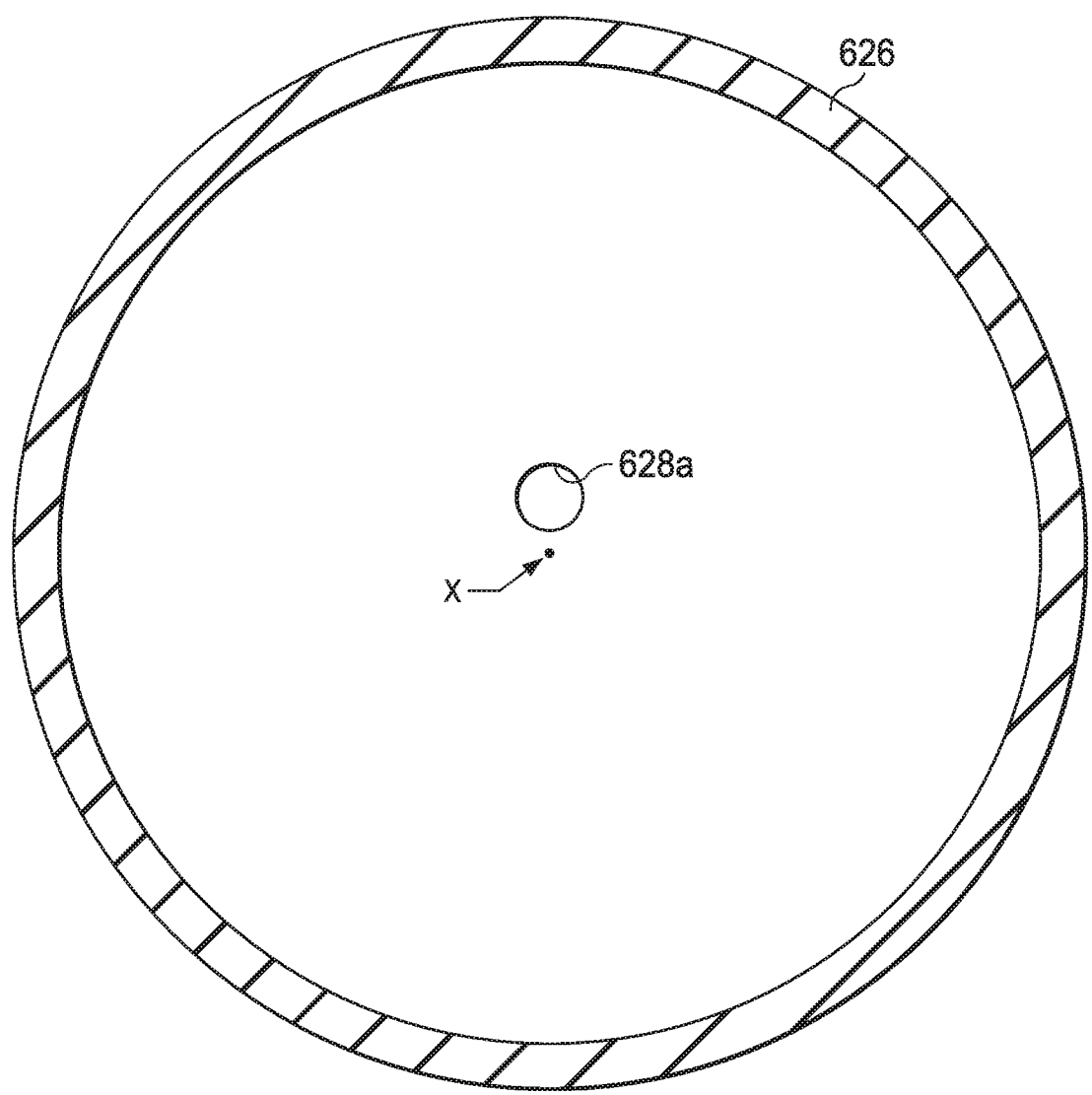
FIG. 6F is a cross-sectional view of an example embodiment of a main assembly of an endoscopic system.

As illustrated in at least the cross-sectional views of FIGS. 6C-E, the main assembly 620 may also include one or more pressure cavities 628*b* provided through the main assembly 620. One or more of the pressure cavities 628*b* may be connected at its proximal end to one or more pressure sources 640*b* and connected at its distal end to one or more expandable members 626. Although the figures may illustrate example embodiments of the main assembly 620 having an expandable member 626, it is to be understood that example embodiments of the main assembly 620 may include more than one expandable member 626 or not include any expandable members 626. In example embodiments where the main assembly 620 includes more than one expandable member 626, the main assembly 620 may also include more than one corresponding pressure cavities (e.g., pressure cavity 628*b*). In example embodiments where the main assembly 620 does not include any expandable members 626, the main assembly 620 may also not include corresponding pressure cavity or cavities (e.g., pressure cavity 628*b*).

In an example embodiment, a pressure applied in each of the one or more pressure cavities 628*b* may be selectively controllable by a surgeon, operator, and/or controller (not shown) via the one or more pressure sources 640*b*, and such applied pressure may be selectively switched between an applied negative pressure, an applied positive pressure, or no applied pressure.

In another example embodiment, the pressure cavities 628*b* may include at least a first set and/or a second set of cavities. The first set of one or more pressure cavities 628*b* may be connected to a positive pressure source 640*b*, in which case such first set of pressure cavities 628*b* may be selectively controllable by a surgeon, operator, and/or controller (not shown) via the one or more positive pressure sources 640*b* to have an applied positive pressure or no applied pressure. Alternatively or in addition, the second set of one or more pressure cavities 628*b* may be connected to a negative pressure source 640*b*, in which case such second set of pressure cavities 628*b* may be selectively controllable by a surgeon, operator, and/or controller (not shown) via the one or more negative pressure sources 640*b* to have an applied negative pressure or no applied pressure. Although FIGS. 6C-E illustrate a single pressure cavity 628*b*, it is to be understood that more than one pressure cavity 628*b* may be provided in the main assembly 620 without departing from the teachings of the present disclosure.

Pressure Cavity 628*c*

As illustrated in at least the cross-sectional view of FIG. 6C, the main assembly 620 may also include one or more pressure cavities 628*c* provided through the main assembly 620 in a similar manner as cavities 628*a* and 628*b*. The one or more pressure cavities 628*c* may be connected at its proximal end to one or more pressure sources 640*c* and connected at its distal end to one or more pressure openings 623*b*. A pressure applied in each of the one or more pressure cavities 628*c* may be selectively controllable by a surgeon, operator, and/or controller (not shown) via the one or more pressure sources 640*a*, and such applied pressure may be selectively switched between an applied negative pressure, an applied positive pressure, or no applied pressure.

In another example embodiment, the pressure cavities 628*c* may include at least a first set and/or a second set of cavities. The first set of one or more pressure cavities 628*c* may be connected to a positive pressure source 640*c*, in which case such first set of pressure cavities 628*c* may be selectively controllable by a surgeon, operator, and/or controller (not shown) via the one or more positive pressure sources 640*c* to have an applied positive pressure or no applied pressure. Alternatively or in addition, the second set of one or more pressure cavities 628*c* may be connected to a negative pressure source 640*c*, in which case such second set of pressure cavities 628*c* may be selectively controllable by a surgeon, operator, and/or controller (not shown) via the one or more negative pressure sources 640*c* to have an applied negative pressure or no applied pressure. Although FIG. 6C illustrates a single pressure cavity 628*c*, it is to be understood that more than one pressure cavity 628*c* may be provided in the main assembly 620 without departing from the teachings of the present disclosure.

(ii) Movement Cavities (e.g., Movement Cavities 627*a*, 627*b*, 627*c*, 627*d*)

In an example embodiment, the main assembly 620 may include a plurality of movement cavities provided through the main assembly 620 between the proximal end 620*a* and distal end 620*b* of the main assembly 620. For example, as illustrated in at least FIGS. 6C-E, the main assembly 620 may include one or more movement cavities 627*a*, one or more movement cavities 627*b* opposite to the one or more movement cavities 627*a* (e.g., on a opposite side of a center line axis X formed by the elongated body 620'), one or more movement cavities 627*c*, and one or more movement cavities 627*d* opposite to the one or more movement cavities 627*c*. As will be further described below and in the present disclosure, each movement cavity may be configurable to house at least a portion of one or more tendon members 630. In an example embodiment, the movement cavities may also include or be considered as including corresponding subsection openings 627*a'*, 627*b'*, 627*c'*, and/or 627*d'* of the bendable section 622 (as will be further described below and in the present disclosure).

Figure 6M:
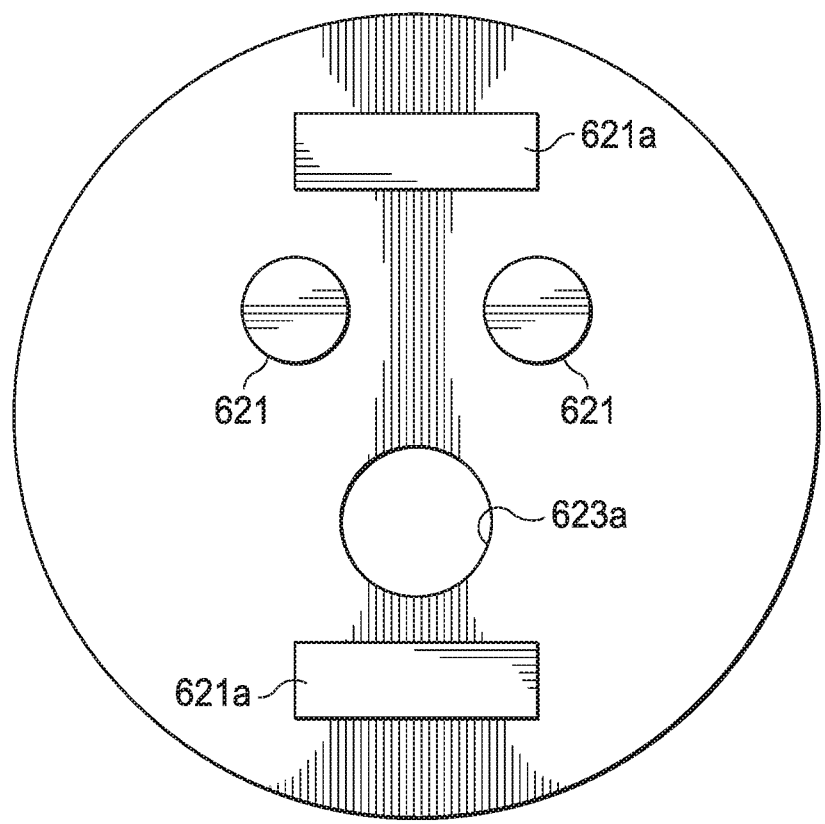
FIG. 6M is a front view of an example embodiment of an endoscopic system.

Although the figures illustrate example embodiments of the main assembly 620 having four movement cavities 627*a*, 627*b*, 627*c*, and 627*d*, it is to be understood that the main assembly 120 may have more or less movement cavities without departing from the teachings of the present disclosure. For example, as illustrated in FIG. 6Q, the main assembly 620 may include three movement cavities 627*a*, 627*b*, and 627*c* (e.g., such three movement cavities may be arranged in such a way that the 3 movement cavities are equally spaced apart relative to one another). As another example, the main assembly 620 may include 8 movement cavities (not shown).

The main assembly 620 may also include other cavities (not shown) provided through the main assembly 620 between the proximal end 620*a* and distal end 620*b* of the main assembly 620, such other cavities for use in housing, among other things, power and/or data cables (e.g., power and/or data cables for an image capturing assembly 621, such as a 3-D stereoscopic or autostereoscopic video camera). Such other cavities may also be for use in providing and/or removing liquid (e.g., water) for and/or from cleaning instruments 621 and/or cleaning an interior of the cavity of the patient. Such other cavities may also be for use in introducing and/or removing instruments 621, tissue, and/or other solids and/or liquids from the interior of the cavity of the patient.

Tendon Members (e.g., Tendon Members 630, 630a, 630b, 630c, 630d)

The main assembly 620 may also include a plurality of tendon members 630. Each tendon member 630 may be secured, attached, and/or connected to a section of the bendable section 624 (e.g., a most distal subsection 624b). One or more of the tendon members 630 may include, resemble, and/or be formed as a cable, twisted cables, etc. that enable a pulling force applied from a proximal end of the tendon member 630 to be translated to the bendable section 624. For example, when a distal end of such tendon member 630 is connected to location 627a' of the most distal subsection 624b (see FIG. 6E), a pulling force applied to a proximal end of the tendon member 630 enables a pulling of location 627a' of the most distal subsection 624b (i.e., the pull causes a tilt or pivot of the side of the most distal subsection 624b where the location 627a' is located) so as to enable the distal end of the bendable section 624 to bend, steer, or turn in the direction of location 627a' (i.e., in a direction depicted by arrow G in FIG. 6E). Alternatively or in addition, one or more of the tendon members 630 may include and/or be formed as a more stiffer and/or less flexible construction (or as a shape member alloy (or SMA) cable or wire) so as to enable an application of a pushing force from a proximal end of the tendon member 630 to be translated to the bendable section 624. For example, when a distal end of such tendon member 630 is connected to location 627c' of the most distal subsection 624b (see FIG. 6E), a pushing force applied to a proximal end of the tendon member 630 enables a pushing of location 627c' of the most distal subsection 624b (i.e., the push causes a tilt or pivot of the side of the most distal subsection 624b where the location 627a' is located) so as to enable the distal end of the bendable section 624 to bend, steer, or turn in the direction of location 627c' (i.e., in a direction depicted by arrow I in FIG. 6E).

Each tendon member 630 may have a length greater than a length of the outer assembly 610, and at least a portion of each tendon member 630 may be housed in a movement cavity 627a-d. For example, as illustrated in at least FIGS. 6C-E, movement cavity 627a may be operable to house one or more tendon members 630a. Alternatively or in addition, movement cavity 627b may be operable to house one or more tendon members 630b. Alternatively or in addition, movement cavity 627c may be operable to house one or more tendon members 630c. Alternatively or in addition, movement cavity 627d may be operable to house one or more tending members 630d.

Navigation Section (e.g., Navigation Section 622)

In an example embodiment, a navigation section 622 may be provided at or near the distal end 620b of the main assembly 620. The navigation section 622 may include an instrument 621 and/or illumination source 621a, as illustrated in at least FIG. 6M. The navigation section 622 may also include a bendable section 624. The navigation section 622 may also include an extendible section 625. The navigation section 622 may also include a main anchor assembly (which may include the one or more pressure openings 623a, one or more pressure openings 623b, and/or expandable member 626). The instrument 621, illumination source 621a, extendible section 625, one or more pressure openings 623a, one or more pressure openings 623b, and expandable member 626 may be arranged in one or more of a plurality of arrangements. For example, as illustrated in at least FIG. 6A, these elements may be arranged (starting from a distal most point of the main assembly 620) as follows: the instrument 621/illumination source 621a/one or more pressure openings 623a on the face of the main assembly 620 (as illustrated in FIG. 6M), followed by the expandable member 626, followed by the bendable section 624, followed by the extendible section 625, and followed by the one or more pressure openings 623b. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the one or more pressure openings 623b, followed by the bendable section 624, and followed by the extendible section 625. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the bendable section 624, followed by the one or more pressure openings 623b, and followed by the extendible section 625. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by one or more additional pressure openings 623a, followed by the expandable member, followed by the one or more pressure openings 623b, followed by the bendable section 624, followed by the extendible section 625, and followed by one or more additional pressure openings 623b. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the one or more pressure openings 623b, followed by the extendible section 625, and followed by the bendable section 624. Alternatively, the elements may be arranged (starting from a distal most point of the main assembly 620) as follows: the instrument 621/illumination source 621a/one or more pressure openings 623a on the face of the main assembly (as illustrated in FIG. 6M), followed by the expandable member 626, followed by the one or more pressure openings 623b, followed by the extendible section 625, followed by the bendable section 624, and followed by another expandable member 626. Other arrangements are also contemplated without departing from the teachings of the present disclosure. These elements of the navigation will now be further described below with reference to the figures.

(i) Instrument (e.g., Instrument 621)

The instrument 621 may include an image capturing assembly 621, such as a 2-D video camera and/or a 3-D stereoscopic or autostereoscopic video camera. Alternatively or in addition, the instrument 621 may include an illumination source 621a, such as one or more LED lights. Alternatively or in addition, the instrument 621 may include a gripper or grasper. Alternatively or in addition, the instrument 621 may include a cutter. Other forms and types of instruments for use in performing endoscopic surgical procedures are also contemplated without departing from the teachings of the present disclosure.

(ii) Bendable Section (e.g., Bendable Section 624)

In an example embodiment, the navigation section 622 may include a bendable section 624. As illustrated in at least FIG. 6B, the bendable section 624 may be provided between the expandable member 626 and extendible section 625. Other arrangements of the bendable section 624 are also contemplated without departing from the teachings of the present disclosure. For example, the extendible section 625 may be provided between the expandable member 626 and bendable section 624. As another example, the bendable section 624 may be provided between the expandable member 626 and pressure openings 623*b*. As another example, the bendable section 624 may be provided between the pressure openings 623*b* and extendible section 625.

The bendable section 624 may be for use in selectively controlling at least a distal end of the bendable section 624 and/or a most distal end portion of the main assembly 620, such as the instrument 621 and/or one or more pressure openings 623*a*. For example, the bendable section 624 may be configurable to selectively bend, turn, or steer in one or more directions (e.g., direct or move the distal end (and/or proximal end) of the bendable section 624 away from a center line axis X formed by the elongated body 620'), and such selective bending, turning, or steering may be based on the amount of pull applied to one or more of the tendon members 630, amount of push applied to one or more of the tendon members 630, and/or how many of the tendon members 630 are pulled and/or pushed. It is recognized in the present disclosure that such selective bending, turning, or steering of the distal end (and/or proximal end) of the bendable section 624 and/or most distal end portion of the main assembly 620 enables the main assembly 620 to advance around the flexural and/or looping/bending sections of a cavity of a patient, such as the colonic lumen of the patient, without forceful manual pushing against the interior wall forming the cavity of the patient.

The bendable section 624 may include a plurality of subsections, including a most proximal subsection 624*a* and a most distal subsection 624*b*. As illustrated in at least FIG. 6A and FIGS. 6I-L, the plurality of subsections may be connected in a linear arrangement via one or more elongated members 624*c* provided through and/or connected to a center of each of the subsections. Each of the one or more elongated members 624*c* may include one or more internal cavities or channels for housing, among other things, the one or more pressure cavities 628*a* and/or the one or more pressure cavities 628*b* (as illustrated in at least FIG. 6E). Each subsection may be pivotally moveable (or capable of being tilted) relative to an adjacent subsection and/or relative to one or more of the elongated members 624*c* (and/or relative to a center of the subsection and/or relative to axis X). As illustrated in the cross-sectional view of FIG. 6E, each subsection may include a plurality of openings provided around its center X'. For example, the most distal subsection 624*b* may include at least portion 627*a'* (which may be a subsection opening 627*a'*) aligned to the movement cavity 627*a* (as illustrated in at least FIGS. 6C-D). The most distal subsection 624*b* may also include a portion 627*b'* (which may be a subsection opening 627*b'*) aligned to the movement cavity 627*b* (as illustrated in at least FIGS. 6C-D). The most distal subsection 624*b* may also include portion 627*c'* (which may be a subsection opening 627*c'*) aligned to the movement cavity 627*c* (as illustrated in at least FIGS. 6C-D). The most distal subsection 624*b* may also include portion 627*d'* (which may be a subsection opening 627*d'*) aligned to the movement cavity 627*d* (as illustrated in at least FIGS. 6C-D). The most proximal subsection 624*a* may also include subsection opening 627*a'* aligned to the movement cavity 627*a* and portion 627*a'* of the most distal subsection 624*b*. The most proximal subsection 624*a* may also include subsection opening 627*b'* aligned to the movement cavity 627*b* and portion 627*b'* of the most distal subsection 624*b*. The most proximal subsection 624*a* may also include subsection opening 627*c'* aligned to the movement cavity 627*c* and portion 627*c'* of the most distal subsection 624*b*. The most proximal subsection 624*a* may also include subsection opening 627*d'* aligned to the movement cavity 627*d* and portion 627*d'* of the most distal subsection 624*b*. In an example embodiment, the movement cavities may also include or be considered as including corresponding subsection openings 627*a'*, 627*b'*, 627*c'*, and/or 627*d'* of the most proximal subsection 624*a* (and may also include portions 627*a'*, 627*b'*, 627*c'*, and/or 627*d'* of the most distal subsection 624*b* when such portions are subsection openings).

As described above and in the present disclosure, each tendon member 630 may be housed in one of the movement cavities. Each tendon member 630 may also extend through a corresponding subsection opening 627*a'*, 627*b'*, 627*c'*, or 627*d'* of the most proximal subsection 624*a* (i.e., a subsection opening that is aligned to the movement cavity that the tendon member is housed), and extend through or connect or secure to a corresponding portion 627*a'*, 627*b'*, 627*c'*, or 627*d'* of the most distal subsection 624*b*.

For example, as illustrated in at least FIGS. 6C-D, a portion of tendon member 630*a* may be housed in movement cavity 627*a*. Another portion of the tendon member 630*a* may be provided through subsection opening 627*a'* of the most proximal subsection 624*a* (and one or more other subsections between the most proximal subsection 624*a* and the most distal subsection 624*b*). A distal end of tendon member 630*a* may also be provided through subsection opening 627*a'* of the most distal subsection 624*a* and connect or terminate at a most distal end of the main assembly 620 (such as at or near the face of the main assembly 620 having the instrument 621). Alternatively or in addition, a distal end of tendon member 630*a* may secure or connect to a portion 627*a'* of the most distal subsection 624*b* that is aligned to the subsection opening 627*a'* of the most proximal subsection 624*a* (and one or more other subsections between the most proximal subsection 624*a* and the most distal subsection 624*b*) and the movement cavity 627*a*. Such portion 627*a'* of the most distal subsection 624*b* may be a subsection opening 627*a'* or a connector, termination, hook, etc. 627*a'* of the most distal subsection 624*b*. It is recognized in the present disclosure that at least a distal end of the bendable section 624 (and/or the most distal end of the main assembly 120) may be configurable to selectively bend, turn, or steer in a selected direction (e.g., direction depicted by arrow G or arrow H in FIG. 6E) when a force (e.g., pulling or pushing force, respectively) is applied to the tendon member 630*a*. An angle θ (as illustrated in FIG. 6N) of such bending, turning, or steering of the distal end of the bendable section 624 by the pulling or pushing force applied to tendon member 630*a* (and/or one or more other tendon members) may be between about 45 to 210 degrees in example embodiments. For example, at least a distal end of the bendable section 624 may be configurable to bend, turn, or steer in a direction depicted by arrow G (in FIG. 6E) when a pulling force is applied to the tendon member 630*a*. FIG. 6N illustrates an example of the bendable section 624 bending when a pulling force is applied to one or more tendon members. As another example, at least a distal end of the bendable section 624 may be configurable to bend, turn, or steer in a direction depicted by arrow H (in FIG. 6E) when a pushing force is applied to the tendon member 630*a*.

As illustrated in at least FIGS. 6C-D, a portion of tendon member 630*b* may be housed in movement cavity 627*b*. Another portion of tendon member 630*b* may be provided through subsection opening 627*b'* of the most proximal subsection 624*a* (and one or more other subsections between the most proximal subsection 624*a* and the most distal subsection 624*b*). A distal end of tendon member 630*b* may also be provided through subsection opening 627*b*' of the most distal subsection 624*a* and connect or terminate at a most distal end of the main assembly 620 (such as at or near the face of the main assembly 620 having the instrument 621). Alternatively or in addition, a distal end of tendon member 630*b* may secure or connect to a portion 627*b*' of the most distal subsection 624*b* that is aligned to the subsection opening 627*b*' of the most proximal subsection 624*a* (and one or more other subsections between the most proximal subsection 624*a* and the most distal subsection 624*b*) and the movement cavity 627*b*. Such portion 627*b*' of the most distal subsection 624*b* may be a subsection opening 627*b*' or a connector, termination, hook, etc. 627*b*' of the most distal subsection 624*b*. It is recognized in the present disclosure that at least a distal end of the bendable section 624 (and/or the most distal end of the main assembly 120) may be configurable to selectively bend, turn, or steer in a selected direction (e.g., direction depicted by arrow H or arrow G in FIG. 6E) when a force (e.g., pulling and/or pushing force, respectively) is applied to the tendon member 630*b*. An angle θ (as illustrated in FIG. 6N) of such bending, turning, or steering of the distal end of the bendable section 624 by the pulling or pushing force applied to tendon member 630*b* (and/or one or more other tendon members) may be between about 45 to 210 degrees in example embodiments. For example, at least a distal end of the bendable section 624 may be configurable to bend, turn, or steer in a direction depicted by arrow H (in FIG. 6E) when a pulling force is applied to the tendon member 630*b*. As another example, at least a distal end of the bendable section 624 may be configurable to bend, turn, or steer in a direction depicted by arrow G (in FIG. 6E) when a pushing force is applied to the tendon member 630*b*.

As another example, as illustrated in at least FIGS. 6C-D, a portion of tendon member 630*c* may be housed in movement cavity 627*c*. Another portion of tendon member 630*c* may be provided through subsection opening 627*c*' of the most proximal subsection 624*a* (and one or more other subsections between the most proximal subsection 624*a* and the most distal subsection 624*b*). A distal end of tendon member 630*c* may also be provided through subsection opening 627*c*' of the most distal subsection 624*a* and connect or terminate at a most distal end of the main assembly 620 (such as at or near the face of the main assembly 620 having the instrument 621). Alternatively or in addition, a distal end of tendon member 630*c* may secure or connect to a portion 627*c*' of the most distal subsection 624*b* that is aligned to the subsection opening 627*c*' of the most proximal subsection 624*a* (and one or more other subsections between the most proximal subsection 624*a* and the most distal subsection 624*b*) and the movement cavity 627*c*. Such portion 627*c*' of the most distal subsection 624*b* may be a subsection opening 627*c*' or a connector, termination, hook, etc. 627*c*' of the most distal subsection 624*b*. It is recognized in the present disclosure that at least a distal end of the bendable section 624 (and/or the most distal end of the main assembly 120) may be configurable to selectively bend in a particular direction when a force (e.g., pulling and/or pushing force) is applied to the tendon member 630*c*. An angle θ (as illustrated in FIG. 6N) of such bending, turning, or steering of the distal end of the bendable section 624 by the pulling or pushing force applied to tendon member 630*c* (and/or one or more other tendon members) may be between about 45 to 210 degrees in example embodiments. For example, at least a distal end of the bendable section 624 may be configurable to bend in a direction depicted by arrow I (in FIG. 6E) when a pulling force is applied to the tendon member 630*c*. As another example, at least a distal end of the bendable section 624 may be configurable to bend, turn, or steer in a direction depicted by arrow J (in FIG. 6E) when a pushing force is applied to the tendon member 630*c*.

In yet another example, as illustrated in at least FIGS. 6C-D, a portion of tendon member 630*d* may be housed in movement cavity 627*d*. Another portion of tendon member 630*d* may be provided through subsection opening 627*d*' of the most proximal subsection 624*a* (and one or more other subsections between the most proximal subsection 624*a* and the most distal subsection 624*b*). A distal end of tendon member 630*d* may also be provided through subsection opening 627*d*' of the most distal subsection 624*a* and connect or terminate at a most distal end of the main assembly 620 (such as at or near the face of the main assembly 620 having the instrument 621). Alternatively or in addition, a distal end of tendon member 630*d* may secure or connect to a portion 627*d*' of the most distal subsection 624*b* that is aligned to the subsection opening 627*d*' of the most proximal subsection 624*a* (and one or more other subsections between the most proximal subsection 624*a* and the most distal subsection 624*b*) and the movement cavity 627*d*. Such portion 627*d*' of the most distal subsection 624*b* may be a subsection opening 627*d*' or a connector, termination, hook, etc. 627*d*' of the most distal subsection 624*b*. It is recognized in the present disclosure that at least a distal end of the bendable section 624 (and/or the most distal end of the main assembly 120) may be configurable to selectively bend in a particular direction when a force (e.g., pulling and/or pushing force) is applied to the tendon member 630*d*. An angle θ (as illustrated in FIG. 6N) of such bending, turning, or steering of the distal end of the bendable section 624 by the pulling or pushing force applied to tendon member 630*d* (and/or one or more other tendon members) may be between about 45 to 210 degrees in example embodiments. For example, at least a distal end of the bendable section 624 may be configurable to bend in a direction depicted by arrow J (in FIG. 6E) when a pulling force is applied to the tendon member 630*d*. As another example, at least a distal end of the bendable section 624 may be configurable to bend, turn, or steer in a direction depicted by arrow I (in FIG. 6E) when a pushing force is applied to the tendon member 630*d*.

It is to be understood that a distal end of the bendable section 624 may be selectively controlled to bend in directions other than those depicted by arrows G, H, I, and J (in FIG. 6E) through a combination of the same or different forces (i.e., same or different amounts of force and/or same or different pulling and/or pushing) applied to two or more tendon members. For example, at least a distal end of the bendable section 624 may be configurable to bend in a direction between arrow G and arrow H (in FIG. 6E) when an equal pulling force is applied to the tendon members 630*a* and 630*b*.

(iii) Extendible Section (e.g., Extendible Section 625)

In an example embodiment, the navigation section 622 may include an extendible section 625. The extendible section 625 may include a proximal end (e.g., the end nearest to the pressure opening 623*b* illustrated in at least FIGS. 6O-P) and a distal end (e.g., the end nearest to the most proximal subsection 624*a* illustrated in at least FIGS. 6O-P). As illustrated in at least FIG. 6B, the extendible section 625 may be provided between the expandable member 626 and the one or more pressure openings 623*b*. Other arrangements/configurations of the extendible section 625 are also contemplated without departing from the teachings of the present disclosure. For example, the extendible section 625 may be provided between the expandable member 626 and bendable section 624. As another example, the extendible section 625 may be provided between the expandable member 626 and pressure openings 623b. As another example, the extendible section 625 may be provided between the pressure openings 623b and bendable section 624.

Figure 6O:
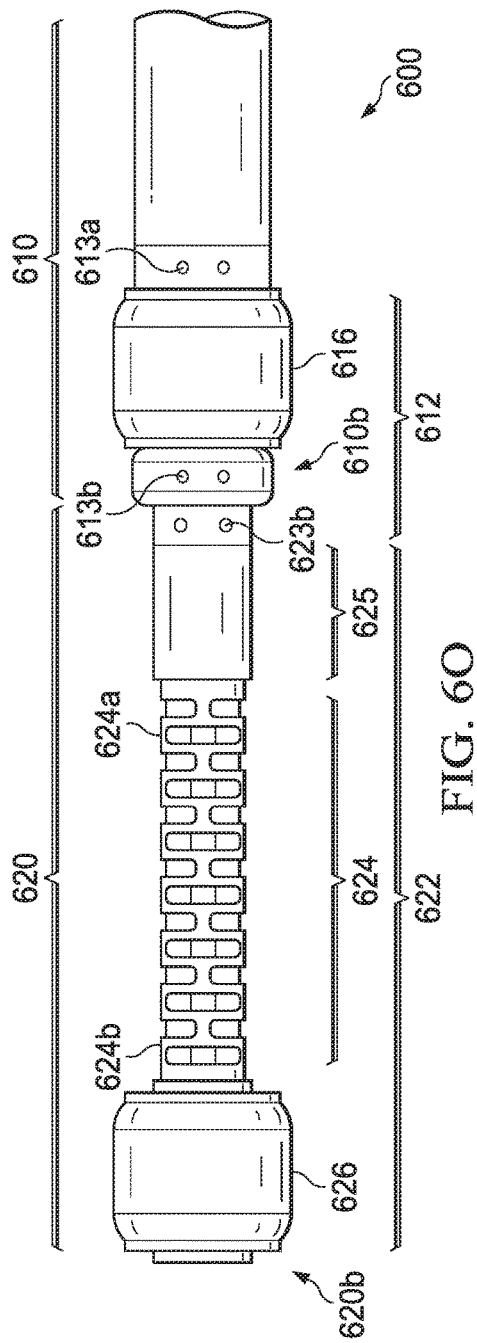
FIG. 6O is a side view of an example embodiment of an endoscopic system having its extendible section configured in the normal or un-extended configuration.
Figure 6P:
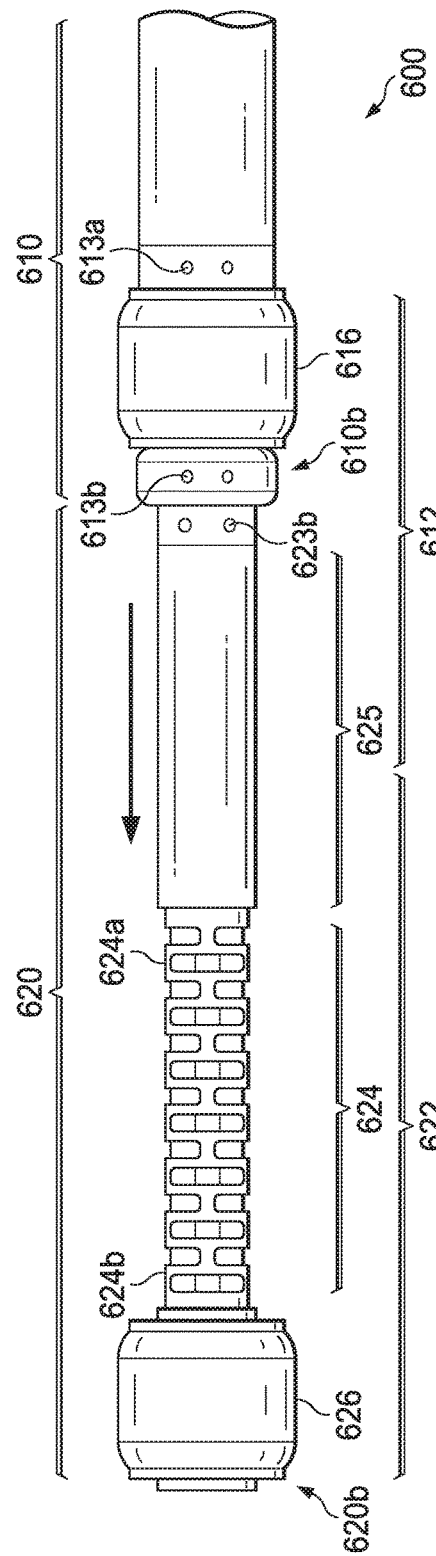
FIG. 6P is a side view of an example embodiment of an endoscopic system having its extendible section configured in an extended configuration.
Figure 6Q:
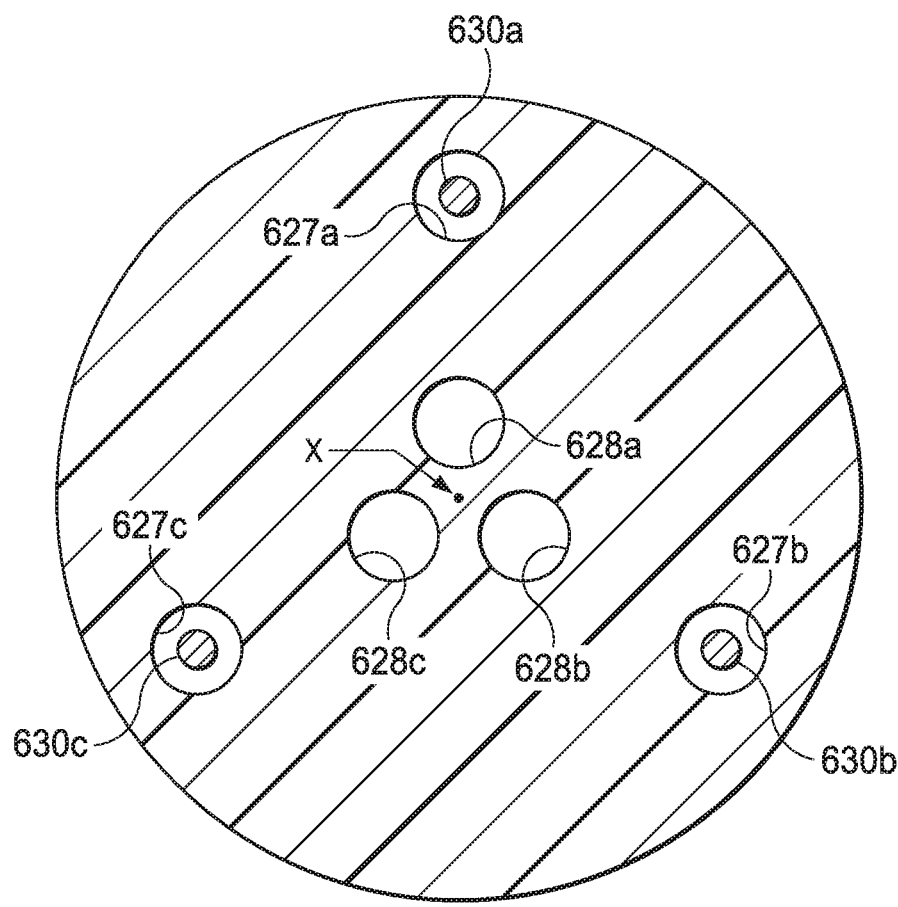
FIG. 6Q is a cross-sectional view of another example embodiment of a main assembly of an endoscopic system having 3 movement channels.

The extendible section 625 may be a section of the main assembly 620 that is configurable to extend and/or contract in length along axis X, as illustrated in at least FIG. 6O and FIG. 6P. Such extending and/or contracting in length of the extendible section 625 may be performed without sliding the outer assembly 610 and the main assembly 620 relative to one another. In an example embodiment, the extendible section 625 may be configurable or configured to extend in length by extending an overall length between the proximal end of the extendible section and the distal end of the extendible section. Similarly, the extendible section 625 may be configurable or configured to contract in length by contracting an overall length between the proximal end of the extendible section and the distal end of the extendible section. FIG. 6O depicts an extendible section 625 having a normal or non-extended configuration or length, and FIG. 6P depicts extendible section 625 having an extended configuration or length. In an example embodiment, the extendible section 625 may be configurable to extend from a normal or non-extended configuration or length of 50 mm to an extended configuration or length of 300 mm. Other dimensions are also contemplated without departing from the teachings of the present disclosure.

The extendible section 625 may be configurable to extend and/or contract in length along axis X in one or more ways. As illustrated in FIG. 6R and FIG. 6S, in an example embodiment, one or more extension cavities 625a may be provided in the main assembly 120 and one or more extension tendon members 625b may be housed in each of the one or more extension cavities 625a. FIG. 6R illustrates the extendible section 625 in a normal or non-extended configuration or length and FIG. 6S illustrates the extendible section 625 in an extended configuration or length. The one or more extension tendon members 625b may be elongated members having relatively stiffer or less bendable construction so as to enable a translation of a pushing force applied at its proximal end to its distal end (i.e., the distal end of the extendible section 625). In an example embodiment, the one or more extension tendon members 625b may be wires or shape memory alloy or SMA wires. In operation, the one or more extension tendon members 625b may be configurable to receive a pushing force applied at its proximal end and extend the extendible section 625 in a distal direction, as illustrated in FIG. 6S. In other example embodiments, the extendible section 625 may include a plurality of mechanical elements that enable the extending and/or contracting of the overall length of the extendible section 625, and such mechanical elements may be driven to cause such extending and/or contracting via an internal motor or the like within the extendible section 625 (or within the navigation section 622, or within the main assembly 620) and/or via an external motor or the like. For example, the mechanical elements may include a telescopic assembly, a spring-loaded or spring-assisted assembly, other memory-shape alloy-based assemblies, etc.

In an example embodiment, at least a portion of the distal end of the extendible section 625 may be configurable or configured to bend in a plurality of directions. Such bending of at least a portion of the extendible section 625 may be performed in one or more of a plurality of ways and using one or more of a plurality of structures, including those described above and in the present disclosure. For example, the bending of at least a portion of the extendible section 625 may be performed using the structures and/or methods described above and in the present disclosure for the bendable section 624. In an example embodiment, at least a portion of the proximal end of the extendible section 625 (and/or the bendable section 624) may be configurable or configured to bend in a plurality of directions. It is to be understood in the present disclosure that, whereas the bending of the distal end of the extendible section 625 (and/or bendable section 624) enables the main assembly 620 to navigate in a forward direction when advancing inwards into a body cavity (e.g., colon), the bending of the proximal end of the extendible section 625 (and/or bendable section 624) may enable the main assembly 620 to navigate in a backwards direction when withdrawing outwards from the body cavity (e.g., colon).

Alternatively or in addition, as illustrated in the embodiments of FIGS. 3B and 3C, the main assembly 130, 620 and outer assembly 150, 610 may be slidable relative to one another, in which case a proximal end of the main assembly 130, 620 may be pushed relative to the outer assembly 150, 610 (or a proximal end of the outer assembly 150, 610 may be pulled relative to the main assembly 130, 620) so that the portion of the main assembly 130, 620 that extends beyond the distal end 150a, 610b of the outer assembly 150, 610 may extend further away from the distal end 150a, 610b of the outer assembly 150, 610 in example embodiments.

(iv) Main Anchor Assembly

In an example embodiment, the navigation section 622 may also include a main anchor assembly. The main anchor assembly may include one or more expandable members 626, one or more pressure openings 623a, and/or one or more pressure openings 623b. In an example embodiment, the pressure opening(s) 623a may be selectively configurable to apply a negative pressure and/or positive pressure independently from the pressure opening(s) 623b (if provided) and/or any other pressure openings (if provided) of the main assembly 620 and/or outer assembly 610. Similarly, the pressure opening(s) 623b (if provided) may be selectively configurable to apply a negative pressure and/or positive pressure independently from the pressure opening(s) 623a and/or any other pressure openings (if provided) of the main assembly 620 and/or outer assembly 610.

Expandable Members 626

The expandable member 626 may be securable or secured to an exterior of the elongated body 620'. The expandable member 626 may include one or more openings for allowing passage of gas and/or liquid, and/or allowing a manipulation of pressure within the expandable member 626. Each such opening may be connected to one or more of the pressure cavities (e.g., pressure cavity 628b). Although the figures may illustrate example embodiments of the main assembly 620 having an expandable member 626, it is to be understood that example embodiments of the main assembly 620 may not include any expandable members 626. In such example embodiments where the main assembly 620 does not include any expandable members 626, the main assembly 620 may also not include corresponding pressure cavity or cavities (e.g., pressure cavity 628b).

In an example embodiment, one or more portions of the exterior surface of the expandable member 626 may include protrusions and/or texture so as to improve securing to the interior wall forming the cavity of the patient. Furthermore, a quantity of between about 1 to 3 expandable members 626 may be provided for the main anchor assembly. Other quantities are also contemplated without departing from the teachings of the present disclosure. The expandable member 626 may be provided at or near a most distal position of the main assembly 620. For example, the expandable member 626 may be provided before pressure openings 623a (pressure openings 623a may be provided at a face of the main assembly 620 (see FIG. 6M) and/or on a side wall of the elongated body 620'). The expandable member 626 may also be provided between pressure opening 623a and bendable section 624. The expandable member 626 may also be provided between bendable section 624 and extendible section 625. The expandable member 626 may also be provided between extendible section 625 and pressure openings 623b, between pressure openings 623a and 623b, and/or before pressure openings 623a. Other configurations and arrangements are also contemplated without departing from the teachings of the present disclosure.

In a normal or non-expanded state, which may be a state in which the pressure source 640b does not provide any positive pressure to the expandable member 626 via the pressure cavity 628b (or the pressure source 640b provides a negative pressure to the expandable member 626 via the pressure cavity 628b), the expandable member 626 may not (or may minimally) protrude outward as compared to the diameter of the elongated body 620'.

In an expanded state, which may be a state in which the pressure source 640b provides a positive pressure to the expandable member 626 via the pressure cavity 628b, the expandable member 626 may be configurable to expand radially outward (e.g., resembling a balloon, tire, or the like). An overall diameter of the expandable member 626, when expanded, may be between about 7 to 25 mm. In an example embodiment, a fully expanded expandable member 626 may have an overall diameter similar or equal to the overall diameter of the expandable member 616 of the outer assembly 610. Other dimensions are also contemplated without departing from the teachings of the present disclosure. During diagnostic and/or therapeutic/surgical procedures when a securing or anchoring of the main assembly 620 with respect to an interior wall forming a cavity of a patient (e.g., interior wall of a colon) is desired or required, the expandable member 626 may be expanded to its expanded state. It is recognized in the present disclosure that the securing or anchoring of the main assembly 620 with respect to the interior wall forming the cavity of the patient may be performed solely by the expandable member 626 (configured in the expanded state), solely by the pressure opening(s) 623a (via applying a negative pressure or suction), or solely by the pressure opening(s) 623c (via applying a negative pressure or suction). Alternatively, the securing or anchoring of the main assembly 620 may be performed cooperatively by the expandable member 626 (configured in the expanded state), pressure opening(s) 623a (via applying a negative pressure or suction), and/or pressure opening(s) 623c (via applying a negative pressure or suction), as further described below and in the present disclosure.

When transitioning from an expanded state to the normal or non-expanded state, the one or more pressure sources 640b do not provide a positive pressure to the expandable member 626 via the one or more pressure cavities 628b. In such transitioning, the pressure source 640b may provide a negative pressure to the expandable member 626 via the one or more pressure cavities 628b. During diagnostic and/or therapeutic/surgical procedures when an unsecuring or unanchoring of the main assembly 620 with respect to an interior wall forming a cavity of a patient is desired or required (e.g., when the expandable member 626 is in the expanded state), the expandable member 626 may be unexpanded (or deflated, shrunken, or collapsed) to its normal or non-expanded state. It is recognized in the present disclosure that the unsecuring or unanchoring of the main assembly 620 with respect to the interior wall forming the cavity of the patient may be performed solely by the expandable member 626 (configured in the non-expanded state), solely by the pressure opening(s) 623a (via applying a positive pressure), or solely by the pressure opening(s) 623c (via applying a positive pressure). Alternatively, the unsecuring or unanchoring of the main assembly 620 may be performed cooperatively by the expandable member 626 (configured in the non-expanded state), pressure opening(s) 623a (via applying a positive pressure), and/or pressure opening(s) 623c (via applying a positive pressure), as further described below and in the present disclosure.

Pressure Openings 623a

The main anchor assembly may also include one or more pressure openings 623a. As illustrated in at least FIG. 6A and FIG. 6M (which is a frontal view of the end of main assembly 620 in the direction depicted by arrow Y in FIG. 6A), the one or more pressure openings 623a may be provided at a most distal portion of the main assembly 620 (e.g., a face of the main assembly 620 illustrated in FIG. 6M). Alternatively or in addition, the one or more pressure openings 623a may be an opening on a side of the elongated body 620'. The one or more pressure openings 623a may be connected to the one or more pressure cavities 628a. In an example embodiment, each of the one or more pressure openings 623a may be formed in one or more of a plurality of shapes, such as a circle, oval, triangle, square, rectangle, slit, etc. Furthermore, each of the one or more pressure openings 623a may have a diameter of between about 200 to 8000 microns. Furthermore, a quantity of between about 1 to 10 pressure openings 623a may be provided. Other dimensions, shapes, and/or quantities are also contemplated without departing from the teachings of the present disclosure. Although the figures illustrate a single pressure opening 623a centered on axis X, it is to be understood that more than one pressure opening 623a (which may be spread around axis X) may be provided without departing from the teachings of the present disclosure.

In a normal state, which may be a state in which the pressure source 640a does not provide any negative or positive pressure to the pressure cavity 628a, the one or more pressure openings 623a may not provide any negative or positive pressure to an exterior of the one or more pressure openings 623a.

In a securing/anchoring state, which may be a state in which the one or more pressure sources 640a provide a negative pressure to the one or more pressure cavities 628a, the one or more pressure openings 623a may provide a negative pressure (e.g., suction force inwards) to an exterior of the main assembly 620 (e.g., an area outside of the one or more pressure openings 623a). During diagnostic and/or therapeutic/surgical procedures when a securing or anchoring of the main assembly 620 with respect to an interior wall forming a cavity of a patient is desired or required, the one or more pressure openings 623a may provide a negative pressure (e.g., suction force inwards) so as to secure/anchor or further improve the securing or anchoring of the main assembly 620 (e.g., in addition to the securing/anchoring provided by the expandable member 626 in its expanded state and/or pressure opening(s) 623b). For example, when a sufficient negative pressure is applied by the one or more pressure openings 623a, such applied negative pressure may be operable to bring inwards or collapse a surrounding portion of the interior wall forming the cavity of the patient nearby the one or more pressure openings 623a towards the main assembly 620 (e.g., see example illustrated in FIG. 8F). It is recognized in the present disclosure that the securing or anchoring of the main assembly 620 with respect to the interior wall forming the cavity of the patient may be performed solely by the one or more pressure openings 623a (via applying a negative pressure or suction), solely by the expandable member 626 (configured in the expanded state), or solely by the pressure opening(s) 623b (via applying a negative pressure or suction). Alternatively, the securing or anchoring of the main assembly 620 may be performed cooperatively by the one or more pressure openings 623a (via applying a negative pressure or suction), the expandable member 626 (configured in the expanded state), and/or pressure opening(s) 623b (via applying a negative pressure or suction), as described in the present disclosure. It is recognized in the present disclosure that the expanding and contacting of the expandable member 626 with the interior wall forming the cavity of the patient and the negative pressure applied by the one or more pressure openings 623a may provide for improved securing or anchoring of the main assembly 620. Similarly, the simultaneous application of negative pressure by the one or more pressure openings 623a and the one or more pressure openings 623b may provide for improved securing or anchoring of the main assembly 620.

In an un-securing/un-anchoring state, which may be a state in which the pressure source 640a provides a positive pressure to the pressure cavity 628a, the one or more pressure openings 623a may provide positive pressure to an exterior of the main assembly 620 (e.g., an area outside of the one or more pressure openings 623a). During diagnostic and/or therapeutic/surgical procedures when a securing or anchoring of the main assembly 620 with respect to an interior wall forming a cavity of a patient is no longer desired or required (e.g., a movement of the main assembly 620 is desired or required) and/or if a surrounding portion of an interior wall forming a cavity of a patient nearby the one or more pressure openings 623a needs to be urged or pushed outwards away from the endoscopic system 600, the one or more pressure openings 623a may provide a positive pressure so as to unsecure/unanchor or further improve the unsecuring or unanchoring of the main assembly 620 (e.g., in addition to the unsecuring/unanchoring provided by the expandable member 626 in its non-expanded state and/or pressure opening(s) 623b). For example, when a sufficient positive pressure is applied by the one or more pressure openings 623a, such applied positive pressure may be operable to urge/push outwards, expanded, or un-collapse a surrounding portion of the interior wall forming the cavity of the patient nearby the one or more pressure openings 623a away from the main assembly 620 (e.g., see example illustrated in FIGS. 8B and 8I). It is recognized in the present disclosure that the unsecuring or unanchoring of the main assembly 620 with respect to the interior wall forming the cavity of the patient may be performed solely by the one or more pressure openings 623a (via applying a positive pressure), solely by the expandable member 626 (configured in the non-expanded state), or solely by the pressure opening(s) 623b (via applying a positive pressure). Alternatively, the unsecuring or unanchoring of the main assembly 620 may be performed cooperatively by the one or more pressure openings 623a (via applying a positive pressure), the expandable member 626 (configured in the non-expanded state), and/or pressure opening(s) 623b (via applying a positive pressure), as described in the present disclosure. It is recognized in the present disclosure that the non-expanding of the expandable member 626 and the positive pressure applied by the one or more pressure openings 623a may provide for improved unsecuring or unanchoring of the main assembly 620. Similarly, the simultaneous application of positive pressure by the one or more pressure openings 623a and the one or more pressure openings 623b may provide for improved unsecuring or unanchoring of the main assembly 620.

In an example embodiment, the one or more pressure openings 623a may be oriented at an angle (not shown) relative to a central axis Y of the main assembly 620 so as to provide a more directional application of negative and/or positive pressure. For example, the one or more pressure openings 623a may be oriented in such a way that the applied negative and/or positive pressure is directed forward (or away from the distal end of the outer assembly 610).

Pressure Openings 623b

The main anchor assembly may also include one or more pressure openings 623b. As illustrated in at least FIG. 6A, the one or more pressure openings 623b may be provided adjacent to the extendible section 625. For example, the extendible section 625 may be provided between the one or more pressure openings 623b and the bendable section 624. The one or more pressure openings 623b may be an opening in the elongated body 620' connected to the one or more pressure cavities 628c. In an example embodiment, each of the one or more pressure openings 623b may be formed in one or more of a plurality of shapes, such as a circle, oval, triangle, square, rectangle, slit, etc. Furthermore, each of the one or more pressure openings 623b may have a diameter of between about 200 to 2000 microns. Furthermore, a quantity of between about 1 to 10 pressure openings 623b may be provided. Other dimensions, shapes, and/or quantities are also contemplated without departing from the teachings of the present disclosure. Although the figures illustrate a single row of pressure openings 623b aligned perpendicular to axis X, it is to be understood that more than one row of pressure openings 623b (which may be aligned perpendicular to axis X and/or at other angles relative to axis X) and/or one or more rows or pressure openings 623b aligned parallel to axis X may be provided in the main anchor assembly without departing from the teachings of the present disclosure. It is also to be understood that the one or more pressure openings 623b may be arranged in other configurations. For example, the one or more pressure openings 623b may be arranged between the expandable member 626 and bendable section 624. Alternatively or in addition, the one or more pressure openings 623b may be arranged between the bendable section 624 and extendible section 625. Other configurations/arrangements are contemplated without departing from the teachings of the present disclosure.

In a normal state, which may be a state in which the pressure source 640c does not provide any negative or positive pressure to the pressure cavity 628c, the one or more pressure openings 623b may not provide any negative or positive pressure to an exterior of the one or more pressure openings 623b.

In a securing/anchoring state, which may be a state in which the one or more pressure sources 640c provide a negative pressure to the one or more pressure cavities 628c, the one or more pressure openings 623b may provide a negative pressure (e.g., suction force inwards) to an exterior of the main assembly 620 (e.g., an area outside of the one or more pressure openings 623b). During diagnostic and/or therapeutic/surgical procedures when a securing or anchoring of the main assembly 620 with respect to an interior wall forming a cavity of a patient is desired or required, the one or more pressure openings 623b may provide a negative pressure (e.g., suction force inwards) so as to secure/anchor or further improve the securing or anchoring of the main assembly 620 (e.g., in addition to the securing/anchoring provided by the expandable member 626 in its expanded state and/or pressure opening(s) 623a). For example, when a sufficient negative pressure is applied by the one or more pressure openings 623b, such applied negative pressure may be operable to bring inwards or collapse a surrounding portion of the interior wall forming the cavity of the patient nearby the one or more pressure openings 623b towards the main assembly 620 (e.g., see example illustrated in FIG. 8F). It is recognized in the present disclosure that the securing or anchoring of the main assembly 620 with respect to the interior wall forming the cavity of the patient may be performed solely by the one or more pressure openings 623b (via applying a negative pressure or suction), solely by the expandable member 626 (configured in the expanded state), or solely by the pressure opening(s) 623a (via applying a negative pressure or suction). Alternatively, the securing or anchoring of the main assembly 620 may be performed cooperatively by the one or more pressure openings 623b (via applying a negative pressure or suction), the expandable member 626 (configured in the expanded state), and/or pressure opening(s) 623a (via applying a negative pressure or suction), as described in the present disclosure. It is recognized in the present disclosure that the expanding and contacting of the expandable member 626 with the interior wall forming the cavity of the patient and the negative pressure applied by the one or more pressure openings 623b may provide for improved securing or anchoring of the main assembly 620. Similarly, the simultaneous application of negative pressure by the one or more pressure openings 623b and the one or more pressure openings 623a may provide for improved securing or anchoring of the main assembly 620.

In an un-securing/un-anchoring state, which may be a state in which the pressure source 640c provides a positive pressure to the pressure cavity 628c, the one or more pressure openings 623b may provide positive pressure to an exterior of the main assembly 620 (e.g., an area outside of the one or more pressure openings 623b). During diagnostic and/or therapeutic/surgical procedures when a securing or anchoring of the main assembly 620 with respect to an interior wall forming a cavity of a patient is no longer desired or required (e.g., a movement of the main assembly 620 is desired or required) and/or if a surrounding portion of an interior wall forming a cavity of a patient nearby the one or more pressure openings 623b needs to be urged or pushed outwards away from the endoscopic system 600, the one or more pressure openings 623b may provide a positive pressure so as to unsecure/unanchor or further improve the unsecuring or unanchoring of the main assembly 620 (e.g., in addition to the unsecuring/unanchoring provided by the expandable member 626 in its non-expanded state and/or pressure opening(s) 623a). For example, when a sufficient positive pressure is applied by the one or more pressure openings 623b, such applied positive pressure may be operable to urge/push outwards, expanded, or un-collapse a surrounding portion of the interior wall forming the cavity of the patient nearby the one or more pressure openings 623b away from the main assembly 620 (e.g., see example illustrated in FIGS. 8B and 8I). It is recognized in the present disclosure that the unsecuring or unanchoring of the main assembly 620 with respect to the interior wall forming the cavity of the patient may be performed solely by the one or more pressure openings 623b (via applying a positive pressure), solely by the expandable member 626 (configured in the non-expanded state), or solely by the pressure opening(s) 623a (via applying a positive pressure). Alternatively, the unsecuring or unanchoring of the main assembly 620 may be performed cooperatively by the one or more pressure openings 623b (via applying a positive pressure), the expandable member 626 (configured in the non-expanded state), and/or pressure opening(s) 623a (via applying a positive pressure), as described in the present disclosure. It is recognized in the present disclosure that the non-expanding of the expandable member 626 and the positive pressure applied by the one or more pressure openings 623b may provide for improved unsecuring or unanchoring of the main assembly 620. Similarly, the simultaneous application of positive pressure by the one or more pressure openings 623b and the one or more pressure openings 623a may provide for improved unsecuring or unanchoring of the main assembly 620.

In an example embodiment, the one or more pressure openings 623b may be oriented at an angle (not shown) relative to a central axis Y of the main assembly 620 so as to provide a more directional application of negative and/or positive pressure. For example, the one or more pressure openings 623b may be oriented in such a way that the applied negative and/or positive pressure is directed forward (or away from the distal end of the outer assembly 610).

Although example embodiments provided above and in the present disclosure describe the main assembly 620 as including pressure cavities 628a, 628b, and 628c, it is recognized in the present disclosure (and described in the present disclosure and illustrated in at least FIGS. 7A-C) a portion of the pressure cavity 628a (which connects to pressure source 640a at one end and connects to pressure opening 623a of the main assembly 620 at another end) may be provided in the outer assembly 610. Alternatively or in addition, as described in the present disclosure and illustrated in at least FIGS. 7A-C, a portion of the pressure cavity 618b (which connects to pressure source 642b at one end and connects to expandable member 616 of the outer assembly 610 at another end) may be provided in the outer assembly 610. Alternatively or in addition, as described in the present disclosure and illustrated in at least FIGS. 7A-C, a portion of the pressure cavity 618c (which connects to pressure source 642c at one end and connects to pressure opening 613b of the outer assembly 610 at another end) may be provided in the outer assembly 610.

Controller

In an example embodiment, the endoscopic system 600 may include a controller (not shown). The controller may be configurable or configured to control and/or manage one or more elements of the endoscopic system 600.

In an example embodiment, the controller may be configurable to control the instrument 621. For example, when the instrument 621 is a video camera (e.g., a 2-D video camera or 3-D stereoscopic or autostereoscopic video camera), the controller may be configurable to capture still and/or moving images and provide such captured images to a console and/or display of the surgeon and/or operator. The controller may be further configurable to analyze the captured images so as to control, suggest, and/or assist in controlling one or more elements of the endoscopic system 600. For example, the analysis by the controller may be configurable to identify a bend or turn in an upcoming section of a cavity of a patient, and perform, among other things, a bending, turning, or steering the bendable section 624 accordingly (and/or a securing or anchoring of the main assembly 620 and/or outer assembly 610).

In example embodiments wherein one or more portions of the endoscopic system 600 includes sensors (e.g., haptic feedback, temperature sensors, humidity sensors, pressure sensors, etc.), such measurements may also be provided to a console, display, and/or control handle (e.g., joystick, etc.) of the surgeon and/or operator.

The controller may also be configurable to receive commands from a surgeon or operator via a console so as to perform one or more surgical actions. For example, the controller may be configurable to receive commands to expand one or more expandable members (e.g., expandable member 616 and/or 626), and upon receiving such commands, cause one or more pressure sources (e.g., pressure source 640*b* and/or 642*b*) to provide positive pressure to expandable members (e.g., expandable member 616 and/or 626) via one or more pressure cavities (e.g., pressure cavities 618*b* and/or 628*b*). As another example, the controller may be configurable to receive commands to cause a suction force by one or more pressure openings (e.g., pressure openings 613*a*, 613*b*, 623*a*, and/or 623*b*), and upon receiving such commands, cause one or more pressure sources (e.g., pressure source 640*a*, 640*c*, 642*a*, and/or 642*c*) to provide negative pressure to cause a suction force to pressure openings (e.g., pressure openings 613*a*, 613*b*, 623*a*, and/or 623*b*) via one or more pressure cavities (e.g., pressure cavities 618*a*, 618*c*, 628*a*, and/or 628*c*). As another example, the controller may be configurable to receive commands to cause a bending, turning, or steering of the distal end of the endoscopic system 600 (i.e., the bendable section 624), and upon receiving such commands, cause a pulling and/or pushing force or action to a proximal end of one or more tendon members (e.g., tendon members 630*a*, 630*b*, 630*c*, and/or 630*d*). Such pulling and/or pushing force or action in turn causes a pulling and/or pushing force to a most distal subsection 624*b* of the bending section 624 and/or a most distal section of the main assembly 620, as described above and in the present disclosure. The controller may be configured to actuate and/or control the pulling and/or pushing force or action performed to each tendon member via one or more motors, gears, pulleys, etc. (not shown). In yet another example, the controller may be configurable to receive commands to cause an extending of the distal end of the endoscopic system 600 (i.e., the extendible section 625), and upon receiving such commands, cause a pushing force or action to a proximal end of one or more extension tendon members (e.g., extension tendon members 625*b*). Such pushing force or action in turn causes a pushing force to a most distal end of the extendible section 625, as described above and in the present disclosure.

Method of Configuring the Endoscopic System

As illustrated in at least FIGS. 8A-I, an example embodiment of the endoscopic system 600 may be configurable to perform diagnostic and/or therapeutic/surgical actions and/or procedures in one of a plurality of ways. An example embodiment of the endoscopic system 600 may be configurable to perform diagnostic and/or therapeutic/surgical actions and/or procedures in a cavity of a patient in a manner similar, analogous, and/or comparable to one or more aspects of the locomotion of an earthworm, or the like. For example, once inserted into a patient's colonic cavity, movement of the endoscopic system 600 in the patient's cavity (e.g., advancement further into or reversing backward toward the orifice or entry point) may be similar to one or more aspects of the locomotion of an earthworm, or the like, by performing one or more of the following actions (in the same or similar order described below or in a different order): (1) anchoring or securing the outer assembly 610 relative to a section of the patient's cavity (e.g., mucosal wall) by expanding one or more expandable members 616 and/or applying negative pressure from one or more pressure openings 613*a* and/or 613*b* of the outer assembly 610; (2) advancing forward the main assembly 620 relative to the anchored outer assembly 610 by extending a length of the extendible section 625; (3) anchoring or securing the main assembly 620 relative to a section of the patient's cavity (e.g., mucosal wall) by expanding one or more expandable members 626 and/or applying negative pressure from one or more pressure openings 623*a* and/or 623*b* of the main assembly 620; (4) unanchoring or releasing the anchorage of the outer assembly 610 relative to the patient's cavity (as performed in action (1) above) by unexpanding/contracting the expandable member 616, not applying negative pressure from pressure openings 613*a* and/or 613*b*, and/or applying positive pressure from pressure openings 613*a* and/or 613*b*; (5) advancing forward the outer assembly 610 toward the anchored main assembly 620 by contracting the length of the extendible section 625 (i.e., configuring the extendible section 625 to contract in length so as to effectively pull the unanchored outer assembly 610 towards the distal end 620*b* of the anchored main assembly 620); (6) anchoring or securing the outer assembly 610 relative to a section of the patient's cavity (e.g., mucosal wall) in a manner similar to that described in action (1) above; (7) unanchoring or releasing the anchorage of the main assembly 620 relative to the patient's cavity by unexpanding/contracting the expandable member 626, not applying negative pressure from pressure openings 623*a* and/or 623*b*, and/or applying positive pressure from pressure openings 623*a* and/or 623*b*; (8) advancing forward the main assembly 620 relative to the anchored outer assembly 610 by extending a length of the extendible section 625 (i.e., configuring the extendible section 625 to extend in length so as to effectively push the unanchored main assembly 620 away from the distal end 610*b* of the anchored outer assembly 610); (9) when encountering a flexural and/or looping/bending section of the patient's cavity, unanchoring the main assembly 620 (if anchored), anchoring the outer assembly 610 (if unanchored), and cooperatively advancing forward (via the extendible section 625 in a similar manner to that described in action (8) above) and bending the main assembly 620 (by bending or actuating the bendable section 624 via the tendons members (e.g., 630*a*, 630*b*, 630*c*, and/or 630*d*)) to follow the flexural and/or looping/bending section of the cavity; and/or (10) repeating one or more of the above actions (1)-(9) to advance the endoscopic system 600 further into the patient's cavity. It is to be understood that one or more of the actions described above and in the present disclosure may be reversely performed so as to reverse the direction of travel of the endoscopic system 600 back towards the orifice or entry point of the patient's cavity.

In respect to the anchoring or securing actions described above and in the present disclosure, although the anchoring force(s) applied by either the expanding of an expandable member (e.g., 616, 626) or the applying of negative pressure from one or more pressure openings (e.g., 613*a*, 613*b*, 623*a*, 623*b*) may be sufficient to anchor or secure the main assembly 620 and/or the outer assembly 610 in the patient's cavity (e.g., to the mucosal wall), it is recognized in the present disclosure that a combination or cooperation of the expanding of an expandable member (e.g., 616, 626) and the applying of negative pressure by one or more pressure openings (e.g., 613*a*, 613*b*, 623*a*, 623*b*) may provide for increased or improved anchoring or securing in the patient's cavity (e.g., to the mucosal wall). Furthermore, by configuring example embodiments of the extendible section 625 to extend in length (e.g., when the outer assembly 610 is anchored and the main assembly 620 is to be advanced forward, or when the main assembly 620 is anchored and the outer assembly 610 is to be reversed backward) and/or contract in length (e.g., when the main assembly 620 is anchored and the outer assembly 610 is to be advanced forward, or when the outer assembly 610 is anchored and the main assembly 620 is to be reversed backward), such extending and/or contracting being drivable by a motor or the like, it is recognized in the present disclosure that example embodiments of the endoscopic system 600 may enable the operator to advance the outer assembly 610 and/or main assembly 620 further into the patient's cavity without the need to manually exert pushing forces at the proximal ends (e.g., 610*a*, 620*a*). Similarly, such extending and/or contracting in length may enable the operator to bring back the outer assembly 610 and/or main assembly 620 towards the orifice or entry point of the patient's cavity without the need to manually exert pulling forces at the proximal ends (e.g., 610*a*, 620*a*). It is also recognized in the present disclosure that driving the extendible section 625 to contract in length (e.g., when the main assembly 620 is anchored and the outer assembly 610 is to be advanced forward) and/or extend in length (e.g., when the outer assembly 610 is anchored and the main assembly 620 is to be advanced forward) instead of having an operator manually exert pushing forces at the proximal end (e.g., 610*a*, 620*a*) may provide for one or more advantages, including, but not limited to: (i) a reduction or elimination in the occurrence of the formation of loops, or the like, in one or more sections of the elongated body (e.g., 610', 620') of the outer assembly 610 and/or main assembly 620 between the proximal (e.g., 610*a*, 620*a*) and distal ends (e.g., 610*b*, 620*b*), (ii) a reduction or elimination in over-extending and/or perforating of the cavity walls (e.g., mucosal walls), (iii) a reduction or elimination in pain caused by looping and/or over-extending and/or perforating of the cavity walls (e.g., mucosal walls), (iv) a reduction in the time required to perform a surgical procedure, and/or (v) a lower threshold or level of expertise and/or skill required by the operator to perform the surgical procedure.

The above actions (1)-(10) are further described below.

In an example embodiment, a method of performing and/or configuring an endoscopic system 600 to perform a diagnostic and/or therapeutic/surgical action and/or procedure in a cavity of a patient may include providing an endoscopic system (e.g., endoscopic system 600). As described above and in the present disclosure, the method may include configuring the endoscopic system 600 to include an outer assembly (e.g., outer assembly 610) and a main assembly (e.g., main assembly 620). At least a portion of the main assembly 620 may be housed in a main cavity (e.g., main cavity 618*d*) of the main cavity.

In configuring the outer assembly, the outer assembly may be provided with an elongated body (e.g., elongated body 610'), a proximal end (e.g., proximal end 610*a*) and a distal end (e.g., distal end 610*b*). The outer assembly may be configured to include a plurality of cavities, including a main cavity (e.g., main cavity 618*d*), one or more first pressure cavities (e.g., pressure cavities 618*a*), one or more second pressure cavities (e.g., pressure cavities 618*b*), and one or more third pressure cavities (e.g., pressure cavities 618*c*). The outer assembly may also be configured to include an outer anchor assembly (e.g., outer anchor assembly 612). The outer anchor assembly may be for use in securing or anchoring the outer assembly relative to an interior wall forming a cavity of the patient. The outer anchor assembly may be configured to include an expandable member (e.g., expandable member 616). The expandable member may connect to the one or more second pressure cavities (e.g., pressure cavity 618*b*), which connect to one or more pressure sources (e.g., pressure source 642*b*). Although the figures may illustrate example embodiments of the outer assembly 610 having an expandable member 616, it is to be understood that example embodiments of the outer assembly 610 may include more than one expandable member 616 or not include any expandable members 616. In example embodiments where the outer assembly 610 includes more than one expandable member 616, the outer assembly 610 may also include more than one corresponding pressure cavities (e.g., pressure cavity 618*b*). In example embodiments where the outer assembly 610 does not include any expandable members 616, the outer assembly 610 may also not include corresponding pressure cavity or cavities (e.g., pressure cavity 618*b*). The outer anchor assembly may also be configured to include one or more distal pressure openings (e.g., pressure openings 613*a*). The one or more distal pressure openings may connect to the one or more first pressure cavities (e.g., pressure cavities 618*a*), which connect to one or more pressure sources 642*a*. The outer anchor assembly may also be configured to include one or more proximal pressure openings (e.g., pressure openings 613*b*). The one or more proximal pressure openings may connect to the one or more third pressure cavities (e.g., pressure cavities 618*c*), which connect to one or more pressure sources 642*c*.

In configuring the main assembly, the main assembly may be provided with an elongated body (e.g., elongated body 620'), a proximal end (e.g., proximal end 620*a*) and distal end (e.g., distal end 620*b*). The main assembly may be configured to include a navigation section (e.g., navigation section 622). As described above and in the present disclosure, the navigation section may be configured to include a bendable section (e.g., bendable section 624), an extendible section (e.g., extendible section 625), and a main anchoring section.

The main assembly may also be configured to include a plurality of cavities, including one or more proximal pressure cavities (e.g., pressure cavities 628*b*), one or more first pressure cavities (e.g., pressure cavities 628*a*), one or more second pressure cavities (e.g., pressure cavities 628*b*), and one or more third pressure cavities (e.g., pressure cavities 628*c*). The main assembly may also be configured to include one or more movement cavities (e.g., movement cavities 627*a*, 627*b*, 627*c*, and 627*d*). The main assembly may also be configured to include one or more tendon members (e.g., tendon member 630, 630*a*, 630*b*, 630*c*, 630*d*), each of which may be housed in a movement cavity. One or more of the tendon members may be configured to include, resemble, and/or be formed as a cable, twisted cables, etc. that enable a pulling force applied from a proximal end of the tendon member 630 to be translated to a bending of a bendable section (e.g., bendable section 624). For example, when a distal end of such tendon member is connected to location (e.g., location 627*a'*) of the most distal subsection (e.g., subsection 624*b*, see FIG. 6E), a pulling force applied to a proximal end of the tendon member enables a pulling of the connected location (e.g., location 627*a'*) of the most distal subsection (i.e., the pull causes a tilt or pivot of the side of the most distal subsection 624*b* where the location 627*a'* is located) so as to enable the distal end of the bendable section to bend, steer, or turn in the direction of the connected location 627a' (i.e., in a direction depicted by arrow G in FIG. 6E). Alternatively or in addition, one or more of the tendon members may be configured to include and/or be formed as a more stiffer and/or less flexible construction (or as a shape member alloy (or SMA) cable or wire) so as to enable an application of a pushing force from a proximal end of the tendon member to be translated to the bendable section. For example, when a distal end of such tendon member is connected to a location (e.g., location 627c') of the most distal subsection (e.g., subsection 624b, see FIG. 6E), a pushing force applied to a proximal end of the tendon member enables a pushing of the connected location (e.g., location 627c') of the most distal subsection (i.e., the push causes a tilt or pivot of the side of the most distal subsection 624b where the location 627a' is located) so as to enable the distal end of the bendable section 624 to bend, steer, or turn in the direction of the connected location 627c' (i.e., in a direction depicted by arrow I in FIG. 6E).

As illustrated in FIG. 8A, the method may include inserting the endoscopic system 600 into an orifice of a patient (e.g., insert, with the distal end 620b first, through a patient's anus and into the rectum). The method may further include providing, from a pressure source (e.g., pressure source 640a), a positive pressure through one or more pressure cavities (e.g., pressure cavity 628a and/or 628b), through one or more pressure openings (e.g., pressure openings 623a and/or 623b), and into the cavity of the patient, as illustrated in at least FIG. 8B. It is recognized that such positive pressure may provide for an expansion or pushing outward of an interior wall forming the cavity of the patient so as to increase a volume of the cavity of the patient and assist in advancing of the endoscopic system 600 further into the cavity of the patient and/or performing diagnostic or surgical actions.

The method may further include advancing the endoscopic system 600 into the cavity of the patient, as illustrated in FIG. 8B. During such advancing, the method may further include identifying, via a still and/or video image captured by the instrument 621 and with the aid of illumination source 621a, a direction of the cavity of the patient. For example, as illustrated in at least FIG. 8C, the image captured by the image capturing assembly 621 may identify that an upcoming section or region of the cavity of the patient that includes a bend or turn (such as a flexural and/or looping/bending section of a colon). The identifying of the direction of the cavity of the patient may be performed by the surgeon or operator (via a console) or the controller, as described above and in the present disclosure. Once a bend or turn in the cavity of the patient is identified, the bendable section (e.g., bendable section 624) may be configured to bend in the direction of the identified bend or turn in the cavity of the patient. Such configuring of the bendable section may be performed via a pulling or pushing of one or more tendon members (e.g., tendon members 630, 630a, 630b, 630c, and/or 630d), and such configuring may be performed by the surgeon or operator (via a console) or the controller, as described above and in the present disclosure.

Figure 8F:
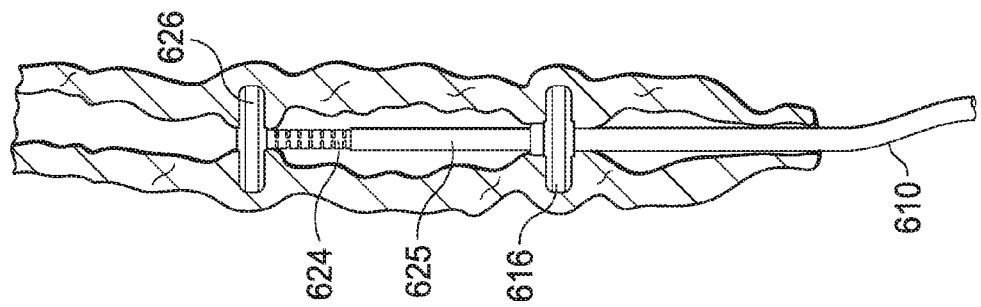
FIG. 8F is an illustration of an example embodiment of a surgical system inserted into the cavity of the patient, having the expandable member of its first (or inner) main body expanded, and applying a negative pressure by one or more pressure openings of its first (or inner) main body so as to provide a securing or anchoring with respect to an interior wall forming the cavity of the patient.
Figure 8E:
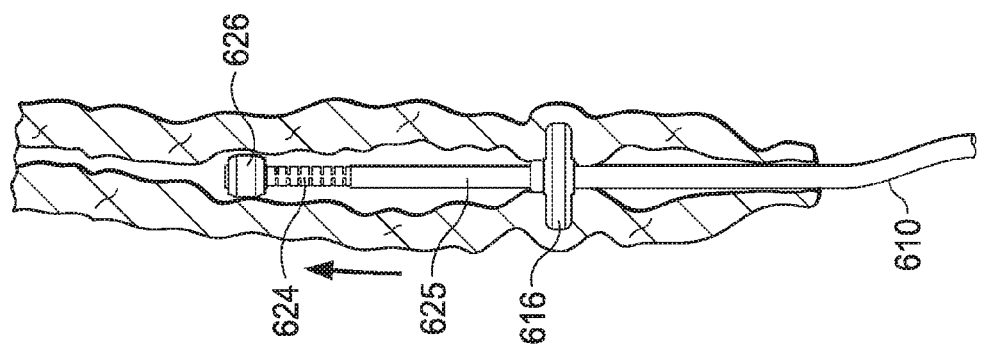
FIG. 8E is an illustration of an example embodiment of a surgical system inserted into the cavity of the patient and having its extendible section extended so as to further advance into the cavity of a patient.
Figure 8D:
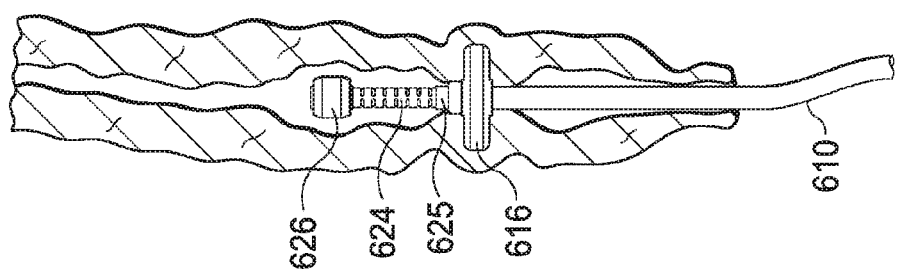
FIG. 8D is an illustration of an example embodiment of a surgical system inserted into the cavity of the patient, having the expandable member of its second (or outer) main body expanded, and applying a negative pressure by one or more pressure openings of its second (or outer) main body so as to collectively provide a securing or anchoring with respect to an interior wall forming the cavity of the patient.
Figure 8J:
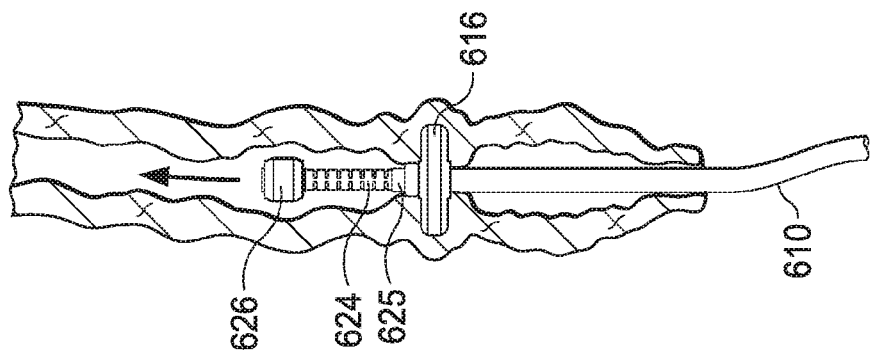
FIG. 8J is an illustration of an example embodiment of a surgical system inserted into the cavity of the patient and un-expanding of the expandable member of its first (or inner) main body.

As illustrated in at least FIG. 8D, the method may further include securing or anchoring the outer assembly 610 with respect to the interior wall forming the cavity of the patient. Such securing or anchoring may be performed by expanding the expandable member 616 of the outer anchor assembly 612 to expand radially outward from the elongated body 610' toward the interior wall forming the cavity of the patient. The pressure source 642b may provide the required positive pressure for the expandable member 616 to expand radially outward, and such positive pressure may be provided via the pressure cavity 618b. Alternatively or in addition, the pressure source 642a may provide a negative pressure to the one or more pressure openings 613a via the pressure cavity 618a. The one or more pressure openings 613a connected to the pressure cavity 618a may provide a suction force inwards from an exterior of the outer assembly 610 (e.g., an area outside of the one or more pressure openings 613a) towards the one or more pressure openings 613a so as to secure or anchor or further improve the securing or anchoring of the outer assembly 610 (i.e., in addition to the securing or anchoring provided by the expandable member 616 in its expanded state). Alternatively or in addition, the pressure source 642c may provide a negative pressure to the one or more pressure openings 613b via the pressure cavity 618c. The one or more pressure openings 613b connected to the pressure cavity 618c may provide a suction force inwards from an exterior of the outer assembly 610 (e.g., an area outside of the one or more pressure openings 613b) towards the one or more pressure openings 613b so as to secure or anchor or further improve the securing or anchoring of the outer assembly 610 (i.e., in addition to the securing or anchoring provided by the expandable member 616 in its expanded state and/or the one or more pressure openings 613a). Such securing of the outer anchor assembly 612 to the interior wall may be performed by the surgeon or operator (via a console) or the controller, as described above and in the present disclosure. It is to be understood in the present disclosure that, in example embodiments where the outer assembly 610 does not include any expandable members 616, the securing or anchoring of the outer assembly 610 may be performable via the negative pressure applied by the pressure opening(s) 613a and/or 613b.

As illustrated in at least FIG. 8E, the method may further include configuring the extendible section 625 to extend further towards the bend section of the cavity of the patient. Such configuring of the extendible section 625 may be performed via the extendible tendon members 625b, as described above and in the present disclosure.

The method may further include adjusting the bend section 624 either before, during, or after the extending of the extendible section 625 so as to further adapt to the bend of the cavity of the patient. Thereafter, as illustrated in at least FIG. 8F, the method may further include configuring the navigation section 622 to secure the main assembly 620 with respect to the interior wall forming the cavity of the patient. Such securing or anchoring may be performed by expanding the expandable member 626 of the main anchor assembly to expand radially outward from the elongated body 620' to at least contact with the interior wall forming the cavity of the patient. The pressure source 640b may provide the required positive pressure for the expandable member 626 to expand radially outward, and such positive pressure may be provided via the pressure cavity 628b. Alternatively or in addition, the pressure source 640a may provide a negative pressure to the one or more pressure openings 623a via the pressure cavity 628a. The one or more pressure openings 623a connected to the pressure cavity 628a may provide a suction force inwards from an exterior of the main assembly 620 (e.g., an area outside of the one or more pressure openings 623a) towards the one or more pressure openings 623a so as to secure or anchor or further improve the securing or anchoring of the main assembly 620 (i.e., in addition to the securing or anchoring provided by the expandable member 626 in its expanded state). Alternatively or in addition, the pressure source 640c may provide a negative pressure to the one or more pressure openings 623b via the pressure cavity 628c. The one or more pressure openings 623b connected to the pressure cavity 628c may provide a suction force inwards from an exterior of the main assembly 620 (e.g., an area outside of the one or more pressure openings 623b) towards the one or more pressure openings 623b so as to secure or anchor or further improve the securing or anchoring of the main assembly 620 (i.e., in addition to the securing or anchoring provided by the expandable member 626 in its expanded state and/or the one or more pressure openings 623a). Such securing of the main anchor assembly to the interior wall may be performed by the surgeon or operator (via a console) or the controller, as described above and in the present disclosure. It is to be understood in the present disclosure that, in example embodiments where the main assembly 620 does not include any expandable members 626, the securing or anchoring of the main assembly 620 may be performable via the negative pressure applied by the pressure opening(s) 623a and/or 623b.

Figure 8I:
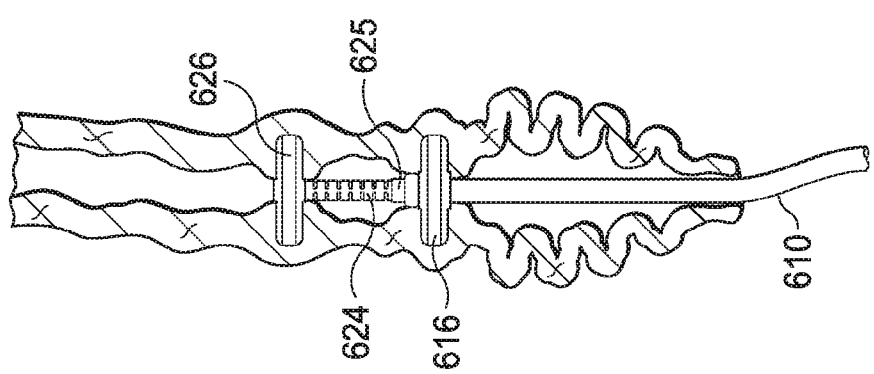
FIG. 8I is an illustration of an example embodiment of a surgical system inserted into the cavity of the patient, expanding of the expandable member of its second (outer) main body, and applying a negative pressure by one or more pressure openings of its second (or outer) main body.
Figure 8H:
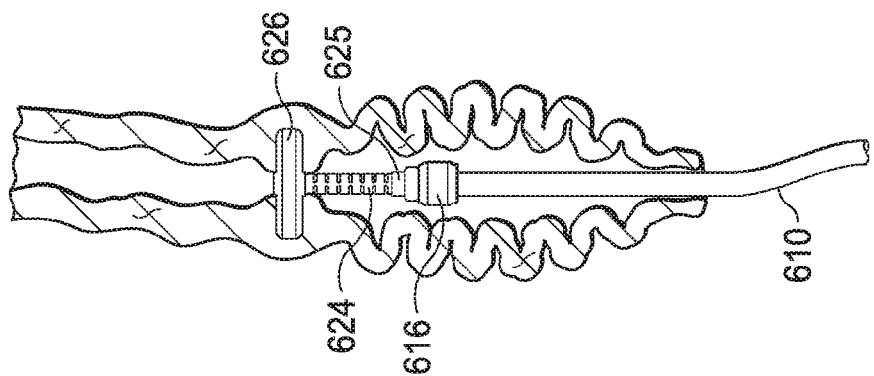
FIG. 8H is an illustration of an example embodiment of a surgical system inserted into the cavity of the patient and having its extendible section contract so as to pull the second (or outer) main body towards the distal end of the first (or inner) main body.
Figure 8G:
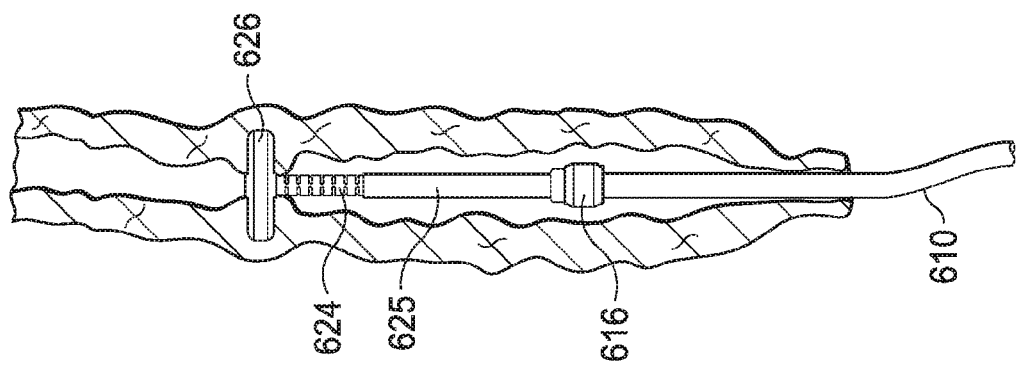
FIG. 8G is an illustration of an example embodiment of a surgical system inserted into the cavity of the patient and un-expanding of the expandable member of its second (or outer) main body.

As illustrated in at least FIG. 8G, the method may further include configuring the outer anchor assembly 612 to un-secure or un-anchor from the interior wall forming the cavity of the patient. This may be achieved by un-expanding (or contracting) the expandable member 616 (if provided and in the expanded configuration or state). Alternatively or in addition, the un-securing or un-anchoring may include not applying a negative pressure (and/or applying a positive pressure) by the one or more pressure openings 613a (if the one or more pressure openings 613a are providing a negative pressure). Alternatively or in addition, the un-securing or un-anchoring may include applying a positive pressure by the one or more pressure openings 613a, as illustrated in at least FIG. 8H, so as to push outwards the interior walls forming the cavity of the patient or expand a volume of the cavity of the patient around the one or more pressure openings 613a. Alternatively or in addition, the un-securing or un-anchoring may include not applying a negative pressure (and/or applying a positive pressure) by the one or more pressure openings 613b (if the one or more pressure openings 613b are providing a negative pressure). Alternatively or in addition, the un-securing or un-anchoring may include applying a positive pressure by the one or more pressure openings 613b, as illustrated in at least FIG. 8H, so as to push outwards the interior walls forming the cavity of the patient or expand a volume of the cavity of the patient around the one or more pressure openings 613b. Thereafter, the outer assembly 610 may be ready to be advanced through the bend section of the cavity of the patient. The advancing of the outer assembly 610 may be performed by un-extending or contracting the extendible section 625. Alternatively or in addition, the advancing of the outer assembly 610 may be performed by pushing a proximal end of the outer assembly 610 (i.e., the elongated member 610') inwards into the cavity of the patient. Either before, during, or after such advancing of the outer assembly 610, the bendable section 624 may be selectively adjusted (e.g., by pulling the surgical system 600 to be more straight), via use of the instrument 621 and aid of the illumination source 621a, so as to have less (or more) bend, turn, or steering in accordance with the bend of the cavity of the patient. The aforementioned un-securing/un-anchoring of the expandable member 616/ pressure openings 613a/pressure openings 613b, advancing of the outer assembly 610, un-extending/contracting of the extendible section 625, and bend adjusting (or straightening) of the bendable section 624 may be performed by the surgeon or operator (via a console) or the controller, as described above and in the present disclosure.

As illustrated in at least FIG. 8I, the method may further include configuring the main anchor assembly to un-secure or un-anchor from the interior wall forming the cavity of the patient. This may be achieved by un-expanding (or contracting) the expandable member 626 (if provided and in the expanded configuration or state). Alternatively or in addition, the un-securing or un-anchoring may include not applying a negative pressure (or applying a positive pressure) by the one or more pressure openings 623a (if the one or more pressure openings 623a are providing a negative pressure). Alternatively or in addition, the un-securing or un-anchoring may include applying a positive pressure by the one or more pressure openings 623a, as illustrated in at least FIG. 8I, so as to push outwards the interior walls forming the cavity of the patient or expand a volume of the cavity of the patient around the one or more pressure openings 623a. Alternatively or in addition, the un-securing or un-anchoring may include not applying a negative pressure (or applying a positive pressure) by the one or more pressure openings 623b (if the one or more pressure openings 623b are providing a negative pressure). Alternatively or in addition, the un-securing or un-anchoring may include applying a positive pressure by the one or more pressure openings 623b, as illustrated in at least FIG. 8I, so as to push outwards the interior walls forming the cavity of the patient or expand a volume of the cavity of the patient around the one or more pressure openings 623b. Thereafter, the main assembly 620 (and the outer assembly 610) may be ready to be advanced through the bend section of the cavity of the patient. The advancing of the main assembly 620 may be performed by extending the extendible section 625. Alternatively or in addition, the advancing of the main assembly 620 (and the outer assembly 610) may be performed by pushing a proximal end of the main assembly 620 (i.e., the elongated member 620') inwards into the cavity of the patient. Alternatively or in addition, the advancing can be performed for both the main assembly 620 and the outer assembly 610 together. Either before, during, or after such advancing, the bendable section 624 may be selectively adjusted (e.g., by pulling the surgical system 600 to be more straight), via use of the instrument 621 and aid of the illumination source 621a, so as to have less (or more) bend, turn, or steering in accordance with the bend of the cavity of the patient. The aforementioned un-securing/un-anchoring of the expandable member 626/pressure openings 623a/ pressure openings 623b, advancing of the main assembly 620 and/or outer assembly 610, un-extending/contracting of the extendible section 625, and bend adjusting of the bendable section 624 may be performed by or via the controller, as described above and in the present disclosure.

It is to be understood in the present disclosure that one or more of the aforementioned actions may be performed, either in whole or in part, manually by an operator/surgeon, assisted, either in whole or in part, by the controller and/or one or more motors (not shown), performed in whole or in part by the controller, and/or performed through the use of artificial intelligence (AI), in example embodiments. For example, the endoscopic system 600 may include, among other things, artificial intelligence to perform automatic and/or adaptive steering functionality based on, among other things, visual data collected by the instrument 621 and/or sensor data collected by one or more sensors.

It is also to be understood in the present disclosure that one or more elements of the endoscopic system (e.g., endoscopic system 600) may be detachable from (and/or attachable or re-attachable to) the endoscopic system 600. For example, one or more of the tendon members (e.g., tendon members 630, 630a, 630b, 630c, and/or 630d) may be removed and/or detached from the main assembly 620. As another example, the main assembly 620 may be removed and/or detached from the outer assembly 610 (e.g., by sliding the main assembly 620 out of the main cavity of the outer assembly 610). As another example, one or more elements of the navigation section 622, such as the bendable section 624, extendible section 625, and/or main anchoring section, may be removed and/or detached from the main assembly 620. In yet another example, the expandable members 616 and/or 626 (if provided) may be removed and/or detached from the outer assembly 610 and/or main assembly 620, respectively. It is recognized in the present disclosure that such detachability (and/or attachability or re-attachability) of one or more elements of the endoscopic system 600 advantageously enables the endoscopic system 600 to be better sterilized/cleaned. Alternatively or in addition, such detachability (and/or attachability or re-attachability) of one or more elements of the endoscopic system 600 advantageously enables such element(s) become single-use and/or disposable elements. Accordingly, example embodiments of the endoscopic system 600 may be configurable to address, reduce, and/or eliminate the problems typically encountered regarding the inability to completely sterilize endoscopic systems (which may pose significant transmission risks of infectious agents).

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An endoscopic system comprising:
an outer assembly, the outer assembly formed as an elongated body and having:
a proximal end;
a distal end;
a first outer pressure cavity provided through the outer assembly between the proximal and distal ends of the outer assembly;
a second outer pressure cavity provided through the outer assembly between the proximal and distal ends of the outer assembly;
a main cavity provided through the outer assembly between the proximal and distal ends of the outer assembly; and
an outer anchor assembly provided at the distal end of the outer assembly, the outer anchor assembly including:
a first expandable member connected to the first outer pressure cavity and configurable to expand radially outwards upon receiving a positive pressure from the first outer pressure cavity; and a first outer pressure opening connected to the second outer pressure cavity, the first outer pressure opening provided adjacent to the first expandable member, the first outer pressure opening selectively configurable to transition between applying a negative pressure and applying a positive pressure; and a main assembly, the main assembly formed as an elongated body and having at least a portion of its elongated body housed in the main cavity of the outer assembly, the main assembly having:
  a proximal end;
  a distal end;
  a first main pressure cavity provided through the main assembly between the proximal and distal ends of the main assembly;
  a second main pressure cavity provided through the main assembly between the proximal and distal ends of the main assembly;
  a plurality of movement cavities provided through the main assembly between the proximal and distal ends of the main assembly in such a way that the plurality of movement cavities are spaced around a center line axis formed by the elongated body of the main assembly;
  a navigation section formed at the distal end of the main assembly, the navigation section having:
    an instrument;
    a second expandable member connected to the first main pressure cavity and configurable to expand radially outwards upon receiving a positive pressure from the first main pressure cavity;
    a bendable section having a plurality of subsections, including a most distal subsection at a distal end of the bendable section and a most proximal subsection at a proximal end of the bendable section, the plurality of subsections connected in a linear arrangement, each subsection pivotally moveable relative to an adjacent subsection, each subsection having a plurality of openings provided around its center;
    an extendible section having a proximal end and a distal end;
    a first main pressure opening connected to the second main pressure cavity, the first main pressure opening selectively configurable to transition between applying a negative pressure and applying a positive pressure, the extendible section configured to extend and contract to change a distance between the proximal end and the distal end of the extendible section and to change a distance between the first main pressure opening and the distal end of the main assembly; and
    a plurality of tendon members, each tendon member housed in one of the movement cavities, each tendon member having a length greater than a length of the outer assembly;

wherein each tendon member extends through one of the subsection openings of the most proximal subsection, wherein a distal end of each tendon member is in communication with a location of the most distal subsection that is aligned to the subsection opening of the most proximal subsection that received the tendon member, and wherein at least a distal end of the bendable section is configurable to bend when a force is applied to one of the tendon members.

2. The endoscopic system of claim 1, wherein the outer assembly further includes a second outer pressure opening, the second outer pressure opening provided adjacent to the first expandable member in such a way that the first expandable member is provided between the first outer pressure opening and the second outer pressure opening, the second outer pressure opening selectively configurable independently from the first outer pressure opening to transition between applying a negative pressure and applying a positive pressure.

3. The endoscopic system of claim 1, wherein the main assembly further includes a second main pressure opening, the second main pressure opening selectively configurable independently from the first main pressure opening to transition between applying a negative pressure and applying a positive pressure.

4. The endoscopic system of claim 1, further comprising:
  a first pressure source for providing the positive pressure and/or the negative pressure to the first outer pressure opening via the second outer pressure cavity;
  a second pressure source for providing at least the positive pressure to the first expandable member via the first outer pressure cavity;
  a third pressure source for providing the positive pressure and/or the negative pressure to the first main pressure opening via the second main pressure cavity; and
  a fourth pressure source for providing at least the positive pressure to the second expandable member via the first main pressure cavity.

5. The endoscopic system of claim 1, wherein the instrument includes an image capturing assembly.

6. The endoscopic system of claim 1,
  wherein the outer assembly further includes a third expandable member configurable to expand radially outwards upon receiving a positive pressure; and
  wherein the third expandable member is provided in such a way that the first outer pressure opening is provided between the first expandable member and the third expandable member.

7. The endoscopic system of claim 3,
  wherein the navigation section further includes a fourth expandable member configurable to expand radially outwards upon receiving a positive pressure; and
  wherein the fourth expandable member is provided in such a way that the second main pressure opening is provided between the second expandable member and the fourth expandable member.

8. The endoscopic system of claim 1, wherein the plurality of tendon members includes a first tendon member, wherein the most distal subsection of the bendable section includes a first opening provided between a center and of the most distal subsection and a side of the most distal subsection, wherein the first tendon member is provided through the first opening of the most distal subsection, wherein the distal end of the bendable section is configurable to bend in a first direction when a pushing force is applied to the first tendon member, and wherein the distal end of the bendable section is configurable to bend in a second direction opposite to the first direction when a pulling force is applied to the first tendon member.

9. An endoscopic system comprising:
  an outer assembly, the outer assembly formed as an elongated body and having:
    a proximal end;
    a distal end;

a first outer pressure cavity provided through the outer assembly between the proximal and distal ends of the outer assembly;

a second outer pressure cavity provided through the outer assembly between the proximal and distal ends of the outer assembly;

a main cavity provided through the outer assembly between the proximal and distal ends of the outer assembly; and an outer anchor assembly provided at the distal end of the outer assembly, the outer anchor assembly including:
- a first expandable member connected to the first outer pressure cavity and configurable to expand radially outwards upon receiving a positive pressure from the first outer pressure cavity; and
- a first outer pressure opening connected to the second outer pressure cavity, the first outer pressure opening provided adjacent to the first expandable member, the first outer pressure opening selectively configurable to apply a negative pressure; and a main assembly, the main assembly formed as an elongated body and having at least a portion of its elongated body housed in the main cavity of the outer assembly, the main assembly having:
- a proximal end;
- a distal end;
- a first main pressure cavity provided through the main assembly between the proximal and distal ends of the main assembly;
- a second main pressure cavity provided through the main assembly between the proximal and distal ends of the main assembly;
- a plurality of movement cavities including at least a first movement cavity, a second movement cavity, and a third movement cavity, the plurality of movement cavities provided through the main assembly between the proximal and distal ends of the main assembly in such a way that the plurality of movement cavities are spaced around a center line axis formed by the elongated body of the main assembly;
- a navigation section formed at the distal end of the main assembly, the navigation section having a serial arrangement of:
  - an instrument;
  - a second expandable member connected to the first main pressure cavity and configurable to expand radially outwards upon receiving a positive pressure from the first main pressure cavity;
  - a bendable section having a plurality of subsections, including a most distal subsection at a distal end of the bendable section and a most proximal subsection at a proximal end of the bendable section, the plurality of subsections connected in a linear arrangement, each subsection pivotally moveable relative to an adjacent subsection, each subsection having a plurality of openings provided around its center, wherein each of the most distal subsection and most proximal subsection include at least a first subsection opening aligned to the first movement cavity, a second subsection opening aligned to the second movement cavity, and a third subsection opening aligned to the third movement cavity;
  - an extendible section having a proximal end and a distal end;
  - a first main pressure opening connected to the second main pressure cavity, the first main pressure opening selectively configurable to apply a negative pressure, the extendible section configured to extend and contract to change a distance between the proximal end and the distal end of the extendible section and to change a distance between the first main pressure opening and the distal end of the main assembly; and
  - a plurality of tendon members including a first tendon member, a second tendon member, and a third tendon member, at least a portion of each tendon member housed in one of the movement cavities, each tendon member having a length greater than a length of the outer assembly;

wherein the first tendon member is housed in the first movement cavity, wherein the first tendon member extends through the first subsection opening of the most proximal subsection, wherein a distal end of the first tendon member is in communication with a location of the most distal subsection that is aligned to the first subsection opening and the first movement cavity, and wherein at least a distal end of the bendable section is configurable to bend in a first direction when a force is applied to the first tendon member;

wherein the second tendon member is housed in the second movement cavity, wherein the second tendon member extends through the second subsection opening of the most proximal subsection, wherein a distal end of the second tendon member is in communication with a location of the most distal subsection that is aligned to the second subsection opening and the second movement cavity, and wherein at least a distal end of the bendable section is configurable to bend in a second direction when a force is applied to the second tendon member, the second direction different from the first direction; and wherein the third tendon member is housed in the third movement cavity, wherein the third tendon member extends through the third subsection opening of the most proximal subsection, wherein a distal end of the third tendon member is in communication with a location of the most distal subsection that is aligned to the third subsection opening and the third movement cavity, and wherein at least a distal end of the bendable section is configurable to bend in a third direction when a force is applied to the third tendon member, the third direction different from the first and second directions.

10. The endoscopic system of claim 9, wherein one or more of the following apply:
the first outer pressure opening is selectively configurable to transition between applying a negative pressure and a positive pressure; and/or
the outer assembly further includes a second outer pressure opening, the second outer pressure opening provided adjacent to the first expandable member in such a way that the first expandable member is provided between the first outer pressure opening and the second outer pressure opening, the second outer pressure opening selectively configurable independently from the first outer pressure opening to apply a negative pressure.

11. The endoscopic system of claim 9, wherein one or more of the following apply:
the first main pressure opening is selectively configurable to transition between applying a negative pressure and a positive pressure; and/or the main assembly further includes a second main pressure opening, the second main pressure opening selectively configurable independently from the first main pressure opening to apply a negative pressure.

12. The endoscopic system of claim 10, further comprising:
   a first pressure source for providing the positive pressure and/or the negative pressure to the first outer pressure opening via the second outer pressure cavity; and
   a second pressure source for providing at least the positive pressure to the first expandable member via the first outer pressure cavity.

13. The endoscopic system of claim 11, further comprising:
   a third pressure source for providing positive pressure and/or the negative pressure to the first main pressure opening via the second main pressure cavity; and
   a fourth pressure source for providing at least the positive pressure to the second expandable member via the first main pressure cavity.

14. The endoscopic system of claim 9,
   wherein the outer assembly further includes a third expandable member configurable to expand radially outwards upon receiving a positive pressure; and
   wherein the third expandable member is provided in such a way that the first outer pressure opening is provided between the first expendable member and the third expandable member.

15. The endoscopic system of claim 11,
   wherein the navigation section further includes a fourth expandable member configurable to expand radially outwards upon receiving a positive pressure; and
   wherein the fourth expandable member is provided in such a way that the second main pressure opening is provided between the second expandable member and the fourth expandable member.

* * * * *